(12) United States Patent
Ahong et al.

(10) Patent No.: US 10,874,559 B2
(45) Date of Patent: Dec. 29, 2020

(54) IMPEDANCE SENSORS FOR DETECTING AND MONITORING MOISTURE IN ABSORBENT ARTICLES

(71) Applicant: Essity Hygiene And Health Aktiebolag, Gothenburg (SE)

(72) Inventors: Timothy Ahong, Aurora (CA); Danny Porthiyas, Toronto (CA); Zachary Fejes, Toronto (CA); Sameer Dhar, Edmonton (CA); Jeremy Dabor, Brantford (CA); Joel Ironstone, Toronto (CA); Harry Qiu, Toronto (CA)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 575 days.

(21) Appl. No.: 15/534,007

(22) PCT Filed: Dec. 10, 2015

(86) PCT No.: PCT/CA2015/051305
§ 371 (c)(1),
(2) Date: Jun. 8, 2017

(87) PCT Pub. No.: WO2016/090492
PCT Pub. Date: Jun. 16, 2016

(65) Prior Publication Data
US 2018/0333306 A1    Nov. 22, 2018

Related U.S. Application Data

(60) Provisional application No. 62/158,481, filed on May 7, 2015, provisional application No. 62/090,478, filed on Dec. 11, 2014.

(51) Int. Cl.
*A61F 13/15* (2006.01)
*A61B 5/00* (2006.01)
(Continued)

(52) U.S. Cl.
CPC .............. *A61F 13/15* (2013.01); *A61B 5/202* (2013.01); *A61B 5/6808* (2013.01);
(Continued)

(58) Field of Classification Search
None
See application file for complete search history.

(56) References Cited

U.S. PATENT DOCUMENTS 5,469,145 A    11/1995  Johnson
5,903,222 A    5/1999   Kawarizadeh et al.
(Continued)

FOREIGN PATENT DOCUMENTS

CN    201775719 U    3/2011
JP    2002/022687 A  1/2002
(Continued)

OTHER PUBLICATIONS

Canadian Office Action dated Nov. 28, 2018 issued in corresponding Canadian patent application No. 2,969,780.
(Continued)

*Primary Examiner* — Douglas X Rodriguez
(74) *Attorney, Agent, or Firm* — Wood Herron & Evans LLP

(57) ABSTRACT

A system is disclosed for detecting moisture in an absorbent article worn by a wearer including an impedance sensing element and an attachment member for securing the impedance sensing element at a location on an exterior surface of the absorbent article. The impedance sensing element includes electrodes. The electrodes are positioned so as to be capacitively coupled to an interior region of the absorbent article and to measure an impedance of the absorbent article from the location on the exterior surface of the absorbent article. The system may also include an impedance measurement subsystem for measuring the impedance of the (Continued)

absorbent article, and extracting a real component of the impedance and an imaginary component of the impedance for determining a characteristic of the moisture in the absorbent article.

22 Claims, 45 Drawing Sheets

(51) Int. Cl.
  *A61B 5/20* (2006.01)
  *A61F 13/42* (2006.01)
  *G16H 40/63* (2018.01)
(52) U.S. Cl.
  CPC ............ *A61B 5/6843* (2013.01); *A61F 13/42* (2013.01); *G16H 40/63* (2018.01); *A61B 2562/029* (2013.01); *A61B 2562/066* (2013.01); *A61F 2013/424* (2013.01)

(56) References Cited

U.S. PATENT DOCUMENTS

| | | | |
|---|---|---|---|
| 6,373,395 B1 | 4/2002 | Kimsey | |
| 6,377,181 B1 | 4/2002 | Kroll et al. | |
| 6,774,800 B2 | 8/2004 | Friedman et al. | |
| 7,126,486 B2 | 10/2006 | Kroll et al. | |
| 7,221,279 B2 | 5/2007 | Nielsen | |
| 7,355,090 B2 | 4/2008 | Ales, III et al. | |
| 7,489,252 B2 | 2/2009 | Long et al. | |
| 7,492,270 B2 | 2/2009 | Veerasamy | |
| 7,551,094 B2 | 6/2009 | Veerasamy | |
| 7,806,882 B1 | 10/2010 | Larkin | |
| 7,945,302 B2 | 5/2011 | McAdams | |
| 7,977,529 B2 * | 7/2011 | Bergman | A61F 13/42 |
| | | | 604/361 |
| 8,274,393 B2 | 9/2012 | Ales et al. | |
| 8,299,317 B2 | 10/2012 | Tippey et al. | |
| 8,304,598 B2 | 11/2012 | Mosbacher et al. | |
| 8,395,014 B2 | 3/2013 | Helmer et al. | |
| 8,421,636 B2 | 4/2013 | Collette et al. | |
| 8,628,506 B2 | 1/2014 | Ales, III et al. | |
| 8,761,858 B1 | 6/2014 | Huttner | |
| 8,866,624 B2 | 10/2014 | Ales, III et al. | |
| 8,884,769 B2 | 11/2014 | Novak | |
| 8,933,292 B2 | 1/2015 | Abraham et al. | |
| 8,975,465 B2 | 3/2015 | Hong et al. | |
| 8,978,452 B2 | 3/2015 | Johnson et al. | |
| 9,131,893 B2 | 9/2015 | Faybishenko et al. | |
| 9,138,354 B2 | 9/2015 | Nhan et al. | |
| 9,160,054 B2 | 10/2015 | Yu et al. | |
| 9,241,839 B2 | 1/2016 | Abraham et al. | |
| 9,278,033 B2 | 3/2016 | Abraham et al. | |
| 9,291,589 B2 | 3/2016 | Wong et al. | |
| 9,314,381 B2 | 4/2016 | Curran et al. | |
| 2003/0216663 A1* | 11/2003 | Jersey-Willuhn | A61B 5/0536 |
| | | | 600/547 |
| 2004/0230172 A1 | 11/2004 | Shapira | |
| 2006/0052678 A1* | 3/2006 | Drinan | A61B 5/0531 |
| | | | 600/301 |
| 2008/0171957 A1 | 7/2008 | Connolly et al. | |
| 2012/0109087 A1* | 5/2012 | Abraham | A61F 13/42 |
| | | | 604/361 |
| 2012/0190956 A1* | 7/2012 | Connolly | A61B 5/0537 |
| | | | 600/372 |
| 2013/0018340 A1* | 1/2013 | Abraham | A61F 13/42 |
| | | | 604/361 |
| 2013/0041334 A1 | 2/2013 | Prioleau et al. | |
| 2013/0261409 A1 | 10/2013 | Pathak et al. | |
| 2014/0266735 A1 | 9/2014 | Riggio et al. | |
| 2014/0276504 A1 | 9/2014 | Heil et al. | |
| 2014/0333441 A1* | 11/2014 | Solazzo | A61F 13/42 |
| | | | 340/573.5 |
| 2014/0371702 A1 | 12/2014 | Bosaeus et al. | |
| 2015/0042489 A1 | 2/2015 | LaVon | |

FOREIGN PATENT DOCUMENTS

| | | |
|---|---|---|
| JP | 2002/022688 A | 1/2002 |
| JP | 2002/082080 A | 3/2002 |
| JP | 2002-224093 A | 8/2002 |
| JP | 2005-516657 A | 6/2005 |
| JP | 2006-504976 A | 2/2006 |
| JP | 2006-508734 A | 3/2006 |
| JP | 2007-532220 A | 11/2007 |
| JP | 2012-532642 A | 12/2012 |
| WO | WO-03/065890 A2 | 8/2003 |
| WO | WO-2004/049942 A1 | 6/2004 |
| WO | WO-2011/004165 A1 | 1/2011 |
| WO | WO-2014/102663 A1 | 7/2014 |

OTHER PUBLICATIONS

Extended European Search Report dated Apr. 18, 2018 issued in corresponding European patent application No. 15868447.2.
Canadian Office Action dated Apr. 29, 2019 issued in Canadian patent application No. 2,969,780.
Mexican Office Action No. 21470 dated Mar. 15, 2019 issued in Mexican patent application No. MX/a/2017/007517 (3 pages) and its English-language translation thereof (2 pages).
Colombian Office Action Oficio No. 8523 dated Aug. 8, 2018 issued in corresponding Colombian patent application No. NC2017/0006795 (21 pages) and its partial English-language translation thereof (6 pages).
Russian Office Action dated Jun. 28, 2018 issued in corresponding Russian patent application No. 2017124235 (6 pages) and its English-language translation thereof (4 pages).
Australian examination report No. 1 dated Sep. 3, 2019 issued in Australian patent application No. 2015361990.
Japanese Office Action dated Jul. 8, 2019 issued in Japanese patent application No. 2017-531259 (4 pages) and its English-language translation thereof (5 pages).
Japanese Office Action dated Jul. 13, 2018 issued in corresponding Japanese patent application No. 2017-531259 and its English-language translation thereof.
Canadian Office Action dated May 30, 2018 issued in Canadian patent application No. 2,969,780.
Korean Office Action (Notice of Grounds for Preliminary Rejection) dated May 31, 2019 issued in Korean patent application No. 10-2017-7019240 (6 pages) and its English-language translation thereof (7 pages).
Russian Decision to Grant dated Feb. 27, 2019 issued in Russian patent application No. 2017124235 (11 pages) and its English-language translation thereof (7 pages).
Japanese Office Action dated Jan. 4, 2019 in Japanese patent application No. 2017-531259 (5 pages) and its English-language translation thereof (6 pages).
European Patent Office communication under Rule 71(3) EPC (intention to grant) dated Mar. 13, 2019 issued in European patent application No. 15868447.2.
Notice of Allowance dated Jan. 27, 2020 issued in Japanese patent application No. 2017-531259 (3 pages) and its English-language translation thereof (3 pages).
Brazilian Written Opinion and Search Report dated Apr. 9, 2020 issued in Brazilian patent application No. BR112017011327-9.

* cited by examiner

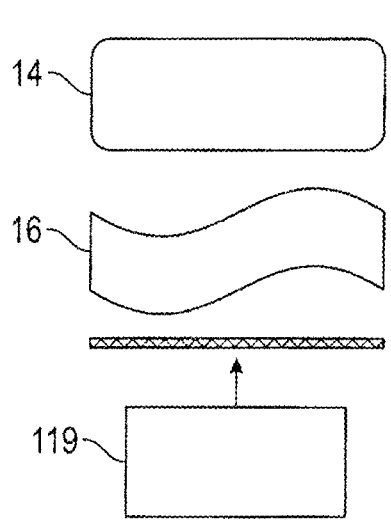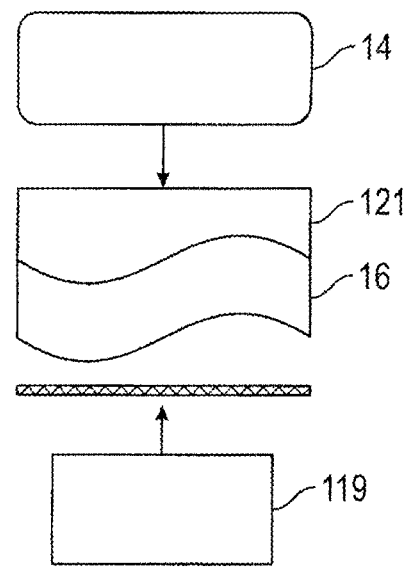
FIG. 10A  FIG. 10B
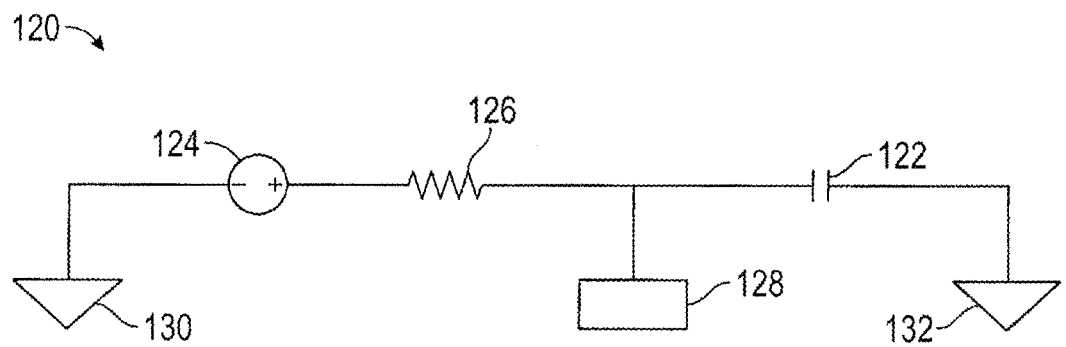
FIG. 11
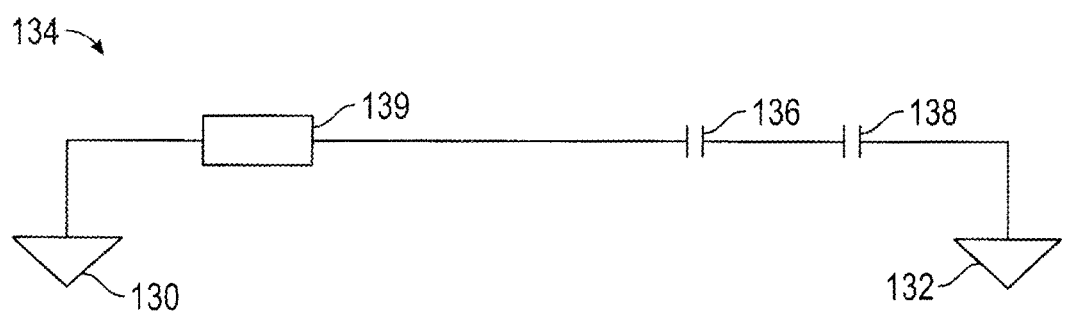
FIG. 12

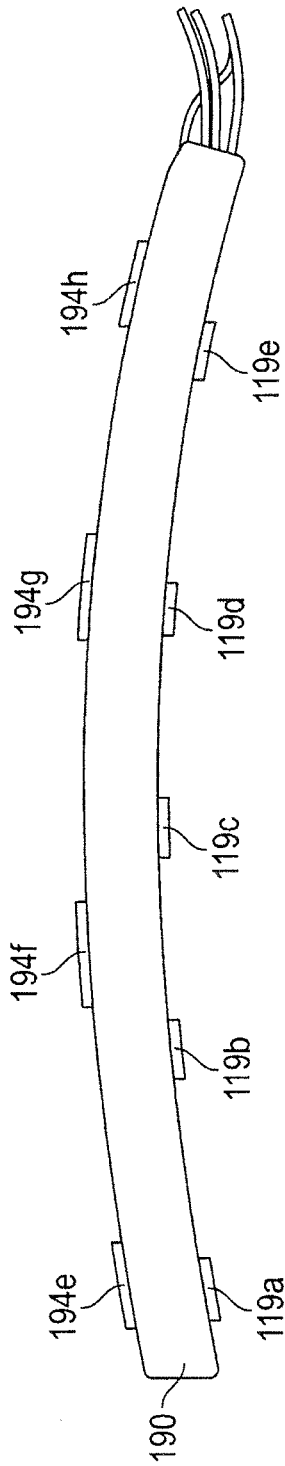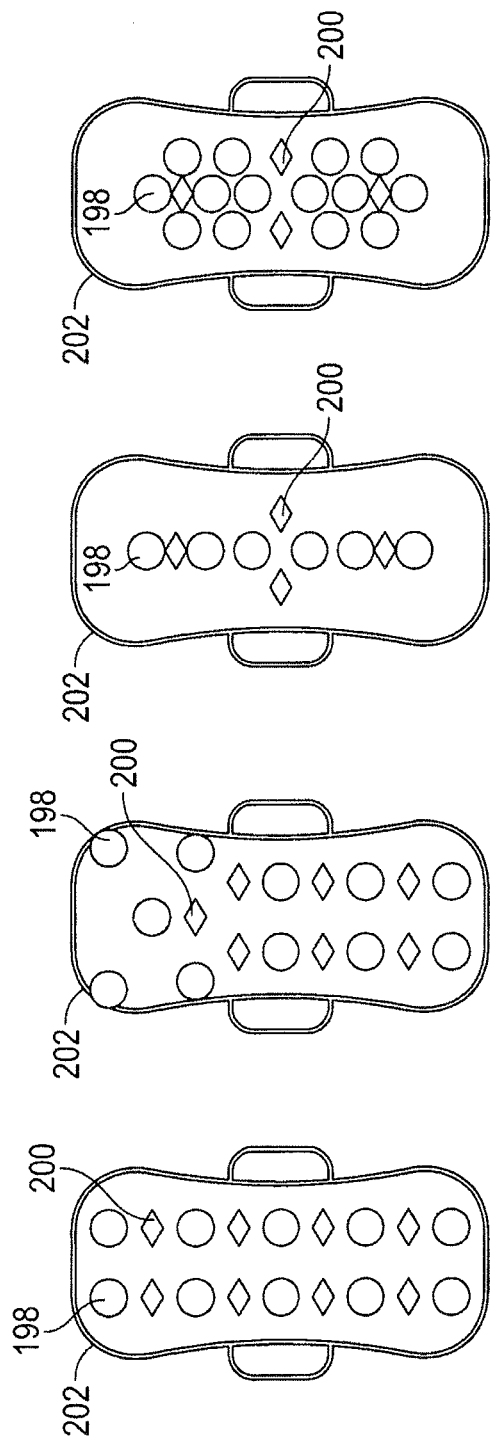

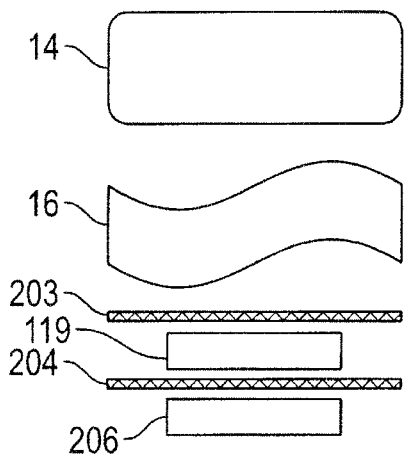
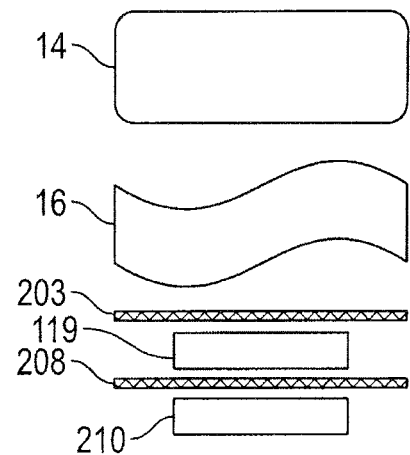
FIG. 24　　　　　　　　　FIG. 25
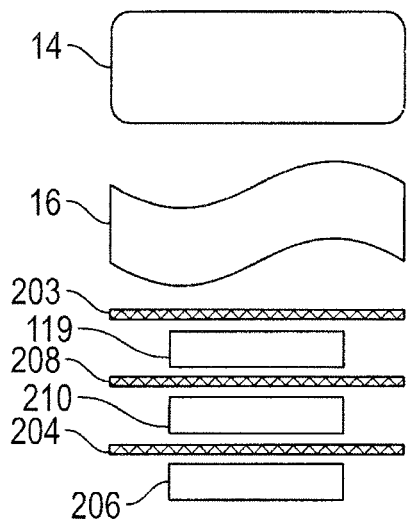
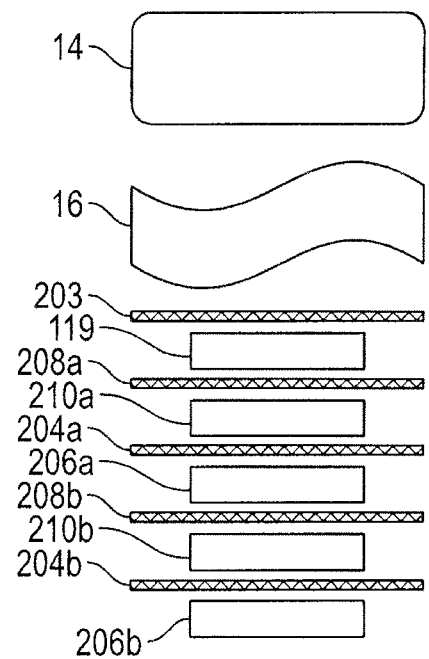
FIG. 26　　　　　　　　　FIG. 27

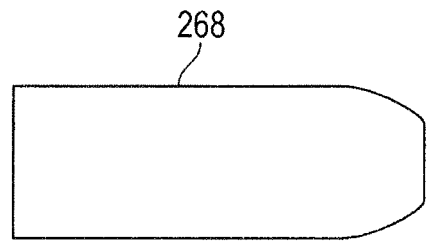
FIG. 34A
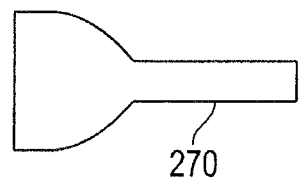
FIG. 34B
FIG. 34C
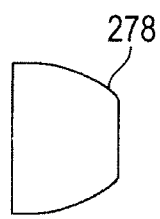
FIG. 34D
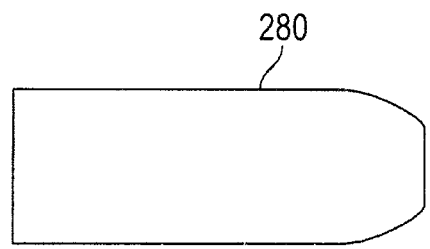
FIG. 34E

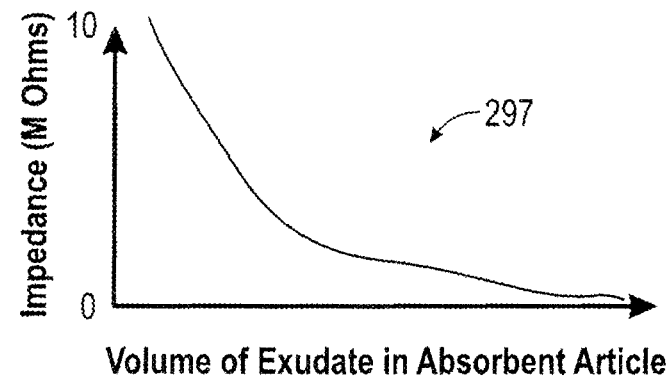
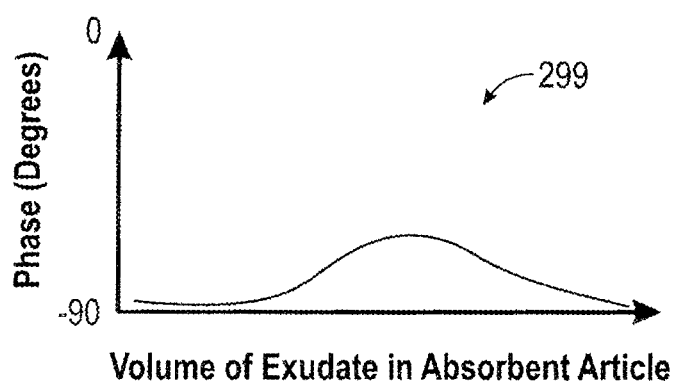
FIG. 61
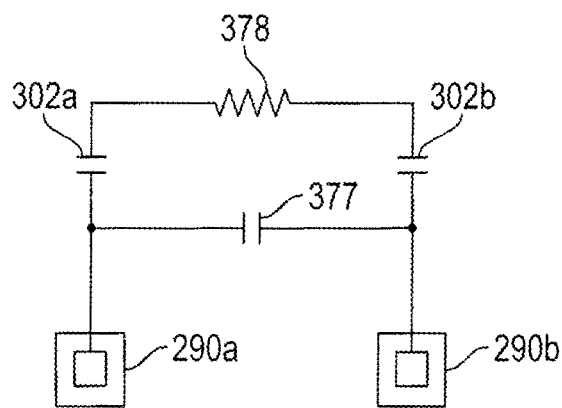
FIG. 62

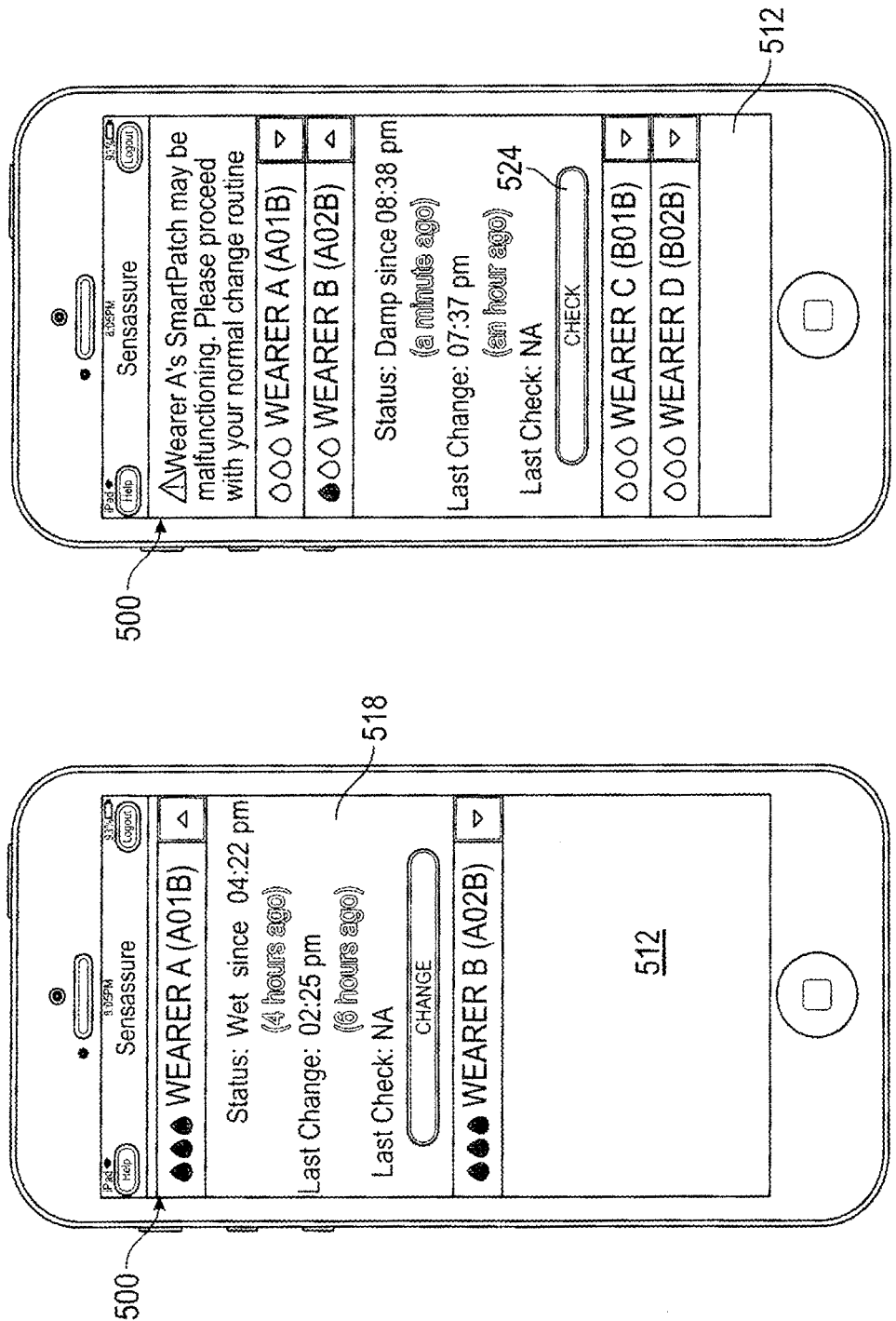

IMPEDANCE SENSORS FOR DETECTING AND MONITORING MOISTURE IN ABSORBENT ARTICLES

CROSS-REFERENCE TO RELATED APPLICATIONS

This application is a § 371 National Stage Application of PCT International Application No. PCT/CA2015/051305 which claims the benefit of U.S. Provisional Application No. 62/090,478, filed on Dec. 11, 2014, and U.S. Provisional Application No. 62/158,481, filed on May 7, 2015, all of which are incorporated by reference herein in their entireties.

TECHNICAL FIELD

The present disclosure generally relates to systems, devices, and related methods for incontinence management. The present disclosure relates more specifically, but not exclusively, to systems, devices and related methods for at least one of detecting and monitoring moisture in absorbent articles, such as diapers (for children and adults), incontinence garments, dressing, and pads, resulting from wetness events caused by, for example, urinary and/or faecal incontinence. Additionally or alternatively, the present disclosure relates to detecting and/or monitoring movement and/or deformation of absorbent articles, resulting from movement events caused by, for example, bed turning, sleep disturbances, standing, sitting, lying down, and/or walking. Additionally or alternatively, the present disclosure relates to detecting and/or monitoring location, position, and/or movements of wearers of absorbent articles.

BACKGROUND

Incontinence is the quality or state of being incontinent, that is, the quality or state of being unable to voluntarily retain urine or faeces. While some forms of incontinence are more widespread in the general population, the condition may usually affect women and the elderly more than others. With respect to the elderly in particular, the condition may affect those residing in long term care facilities commonly referred to as "nursing homes" and assisted living facilities. Urinary incontinence generally refers to an individual's inability to voluntarily retain urine. Faecal incontinence generally refers to an individual's inability to voluntarily retain faeces. A range of different urinary incontinence types are recognized. These different types of urinary incontinence include, for example, stress incontinence, urge incontinence, overflow incontinence, dribble incontinence, and functional incontinence. Oftentimes individuals with urinary incontinence will also have faecal incontinence, but this is not always the case individuals have one type of incontinence without the other. In the context of the present disclosure, the term "incontinence" may encompass one or more of the different types of urinary incontinence and/or faecal incontinence.

Management of incontinence may be useful for persons located in hospitals, long term care facilities or nursing homes, assisted living facilities, retirement homes, geriatric institutions, private homes and the like. These persons may also be located in the community. Persons suspected to suffer from incontinence may have a manual voiding assessment completed upon admission to a care facility. During this manual voiding assessment, caregivers may check wearers at defined time intervals, usually every hour, to assess and record whether an incontinence episode occurred. This voiding assessment, along with a detailed diary of the wearer's fluid intake over the assessment period, may be used to create a personalized care plan. The created personalized care plan may include, but is not limited to, a toileting schedule for the wearer that prescribes times the wearer is to be toileted by caregivers based on the wearer's incontinence patterns. Toileting schedules may be an effective way to promote continence, thereby reducing the number of incontinent events while the wearer is wearing an absorbent article, and the costs associated with using, cleaning, and/or replacing absorbent articles.

A caregiver's adherence to imposed toileting schedules may be low in view of the strain such schedules may place on the caregiver's time, as the caregiver may be asked to individually toilet each wearer according to his or her own toileting schedule. Low compliance to toileting schedules may also be explained by the caregiver understanding that the manual voiding assessment that such schedules are derived from may often times be inaccurate and/or incomplete. Research has also shown that not all wearers living in care facilities benefit from such toileting schedules. For example, toileting schedules may not be as beneficial to a wearer having a high incidence of cognitive impairment resulting from, for example, dementia or Alzheimer's disease, which may result in less predictable patterns of incontinence. In some instances, instead of adhering to toileting schedules for each wearer, the caregiver may adopt a system whereby all wearers' diapers may be checked at prescribed times throughout the day and changed if appropriate. For example in the case of an episode of urinary incontinence, if a wearer's diaper is ¾ full, changing may be appropriate. While this process of checking and changing wearers may lead to time savings for the caregiver, problems with this process still exist. If, for example, the wearer is checked too frequently, the wearer may be unnecessarily interrupted or roused from sleep, and the caregiver's time may be wasted changing dry diapers. On the other hand, if the wearer is checked too infrequently, the wearer may sit in a wet absorbent article for an extended period of time, which may have physical and/or psychological consequences.

Conventional solutions for detecting, monitoring, and/or managing incontinence may have issues in terms of logistics, cost, handling, and/or procedures. For example, conventional capacitive sensors may not be effective at accurately determining a saturation level of an absorbent article and/or accurately estimating the volume of moisture in an absorbent article. Rather, a conventional capacitive sensor may be geared more towards simple wet/dry detection. An absorbent article typically may be capable of holding a certain threshold of liquid, and thus, changing the absorbent article prematurely based on any detection of wetness may be wasteful. Difficulties with conventional capacitive sensors may stem from such sensors being highly prone to noise and environmental effects, changes in elevation, proximity to external conductors such as wheelchairs, mechanical beds, and/or other equipment, and/or differences in wearers' leg thicknesses and sizes. The presence of these factors may impact capacitive sensor readings and introduce inaccuracies.

Moreover, for a device having a conventional impedance sensing component on an interior of an absorbent article, reusing the device may not be possible because its exposure to urine and/or faeces may make reuse unhygienic, which may in turn increase costs associated with using the device due to the device having to be discarded with every absorbent article. Positioning an impedance sensing component on the exterior of the absorbent article may decrease the likelihood of exposing the impedance sensing component to urine and/or faeces, but may result in the impedance sensing component being less able, or even unable, to accurately characterize the degree of wetness in the absorbent article. Conventional external impedance sensing components may be particularly prone to missing enuresis events.

Systems, devices, and methods without one or more of the aforementioned drawbacks may help improve outcomes by, for example, enhancing performance with respect to at least one of detecting and/or monitoring moisture and/or movement, saving caregivers time, improving wearer care, and/or reducing costs.

SUMMARY

Aspects of the present disclosure relate to, among other things, systems, devices, and related methods for incontinence management. Each of the aspects disclosed herein may include one or more of the features described in connection with any of the other disclosed aspects.

In one aspect of the present disclosure, a system for detecting moisture in an absorbent article worn by a wearer includes an impedance sensing element. The impedance sensing element includes electrodes. The system also includes an attachment member for securing the impedance sensing element at a location on an exterior surface of the absorbent article. The electrodes are positioned so as to be capacitively coupled to an interior region of the absorbent article and to measure an impedance of the absorbent article from the location on the exterior surface of the absorbent article. The system may also include an impedance measurement subsystem for measuring the impedance of the absorbent article, and extracting a real component of the impedance and an imaginary component of the impedance for determining a characteristic of the moisture in the absorbent article.

Aspects of the system may also include one or more of the features below. The characteristic may include a presence of the moisture in the absorbent article. The characteristic may include an amount of the moisture in the absorbent article. The impedance measurement subsystem may be configured to measure the impedance between the electrodes. The impedance may be a complex impedance having a magnitude and a phase. The magnitude may be indicative of the characteristic of the moisture. The phase may be indicative of the characteristic of the moisture. A reduction in the phase and the magnitude may be indicative of a state where the absorbent article is wet but not filled to capacity. A reduction in the magnitude but not the phase may be indicative of a state where the absorbent article is filled to capacity. The real component may include a resistive component. The imaginary component may include a reactive component. The impedance measurement subsystem may be configured to perform an optimization technique using a linear regression, a neural network, and/or a support vector machine, to determine a relationship between the resistive and reactive components of the impedance and the characteristic of the moisture. The impedance measurement subsystem may be configured to perform a simulation to determine a relationship between the resistive and reactive components of the impedance and the characteristic of the moisture. The impedance measurement subsystem may be configured to acquire data from another system that is distinct from the system, to determine a relationship between the resistive and reactive components of the impedance and the characteristic of the moisture. The impedance measurement subsystem may be configured to measure the impedance with a sinusoid of a single frequency. The impedance measurement subsystem may be configured to measure the impedance by applying a voltage to one of the electrodes and measuring current at another of the electrodes. The impedance measurement subsystem may be configured to measure the impedance by applying a current to one of the electrodes and measuring a voltage between that electrode and another of the electrodes. The impedance measurement subsystem may be configured to determine the characteristic of the moisture using the real component. The characteristic of the moisture may include a degree of wetness of the absorbent article. The impedance measurement subsystem may be configured to measure the impedance at discrete frequencies. The impedance measurement subsystem may be configured to acquire the resistive and reactive components at discrete frequencies, to determine a relationship between the resistive and reactive components and the characteristic of the moisture. The impedance measurement subsystem may be configured to determine whether the impedance sensing element is attached to the absorbent article based on a characteristic of the reactive component.

In another aspect of the present disclosure, an incontinence management system includes an absorbent article for wearing by a wearer. The absorbent article includes an interior, an exterior, and a barrier layer between the interior and the exterior. The system also includes an impedance sensing element that includes electrodes. The system also includes an attachment member for securing the impedance sensing element to the exterior. The electrodes may be separated from the interior by the barrier layer. The electrodes may be capacitively coupled to the interior through the barrier layer. The electrodes may be positioned to measure an impedance of the absorbent article from the exterior. The system may also include an impedance measurement subsystem for measuring the impedance of the absorbent article, and extracting a real component of the impedance and an imaginary component of the impedance for determining a characteristic of the moisture in the absorbent article.

In another aspect of the present disclosure, a method for detecting moisture in an absorbent article worn by a wearer using an impedance sensing element includes securing the impedance sensing element to an exterior of the absorbent article such that electrodes of the impedance sensing element are capacitively coupled to an interior of the absorbent article. Securing the impedance sensing element includes positioning the electrodes to measure an impedance of the absorbent article from the exterior. The method also includes measuring the impedance of the absorbent article. The method may also include extracting a real component of the impedance and an imaginary component of the impedance for determining a characteristic of the moisture in the absorbent article.

In another aspect of the present disclosure, a monitoring system is used to monitor characteristics such as, for example wetness, in, on, or in the vicinity of one or more articles including, for example, absorbent articles (e.g., diapers), adult briefs, and/or bed linens. The system includes an input for receiving one or more sensing element signals indicative of the presence of a characteristic in, on, or in the vicinity of the article. The system also includes a processor. The system may also include a user interface for communicating with a user of the system. The processor may execute an algorithm to analyze the one or more sensing element signals by applying the one or more received sensing element signals to a mathematical model to characterize a characteristic in, on, or in the vicinity of the article.

In accordance with aspects of the disclosure, the mathematical model uses sensing element signal data and represents a relationship between one or more variables obtainable from the received sensing element signals and a characteristic used to characterize a wetness or other event. For example, other events may include, but are not limited, to wearer movement, position, location, heart rate, and/or other indicators of well-being and/or health status.

In accordance with aspects of the disclosure, the system also includes an input for receiving one or more environmental sensing element signals indicative of a condition of the surrounding environment. Examples of environmental sensing element signals are signals that indicate ambient temperature, humidity, properties of materials in the vicinity, other properties related to the absorbent article, and/or properties of an area surrounding the absorbent article.

According to aspects of the disclosure, the mathematical model combines sensing element signals indicative of a presence of moisture on and/or in the vicinity of the absorbent article with the environmental sensing element signals to monitor a characteristic on or in the vicinity of the absorbent article. The characteristic may include, for example, moisture on and/or in the vicinity of the absorbent article.

According to aspects of the disclosure, the mathematical model may take a number of forms, including a representation between signals and characteristics determined from data and sensing element signals collected from sources other than the system. Additionally or alternatively, the mathematical model may include a representation determined based on data and sensing element signals collected from the system itself. The mathematical model may be specific to a certain type, brand, or group of absorbent articles, where the group may include a set of articles segmented based on their characteristics. Groups of absorbent articles may include, but are not limited to, night briefs for adult females, night briefs for adult males, loose fitting briefs, tight fitting briefs, highly absorbent briefs, and mildly absorbent briefs. The mathematical model may take in this information, and/or information about the wearer, to characterize the wetness event. Information about the wearer that may be used in the mathematical model may include, for example, the wearer's age, weight, sex, core body temperature, body fat, skin integrity, skin pH, urinary pattern history, fecal pattern history, and skin surface moisture.

In accordance with aspects of the disclosure, data (e.g., signals) is generated by one or more sensing elements. Such sensing elements include, but are not limited to, a first conductive member and a second conductive member separated by one or more absorbent materials or articles. The conductive members include any electrically conductive material, including metals, or a biological material such as human skin. In certain embodiments, the first and second conductive members are used to measure or estimate characteristics of the absorbent materials or articles between the first and second conductive members, such as the dielectric constant, electrical capacitance, inductance, resistivity, impedance, or conductivity, and infer the characteristics of a wetness event in, on, or in the vicinity of the absorbent materials or articles. The characteristics of the wetness event may be inferred based on a change in electrical behavior of the absorbent materials or articles, and may be observed in the form of signals measured by at least one of the conductive members and generated at or by another conductive member. The composition of a wetness event, in, on, or in the vicinity of an absorbent material or article, may include the presence of blood, a biological marker, and/or a chemical marker in material exuded into the absorbent materials or articles.

According to aspects of the disclosure, an algorithm used to analyze one or more sensing element signals provides an indication of: a presence, volume, and/or mass of moisture or other material in articles, or in the case of biological materials such as skin being used to generate the sensing element signals, the presence, volume, and/or mass of moisture or other material on a biological material; characteristics relating to moisture in articles, such as temperature, pH, viscosity, odor, pressure, and/or the presence or quantity of biological or chemical molecules; the spatial distribution of moisture in articles; a clinical condition associated with wetness events, such as urinary incontinence suffered by an individual monitored by the system, where the form of incontinence could be selected from the group including urinary, fecal, dribble, stress, overflow, urge, mixed urinary incontinence (MUI), total and functional incontinence, or incontinence tied to a urinary tract infection (UTI) suffered by an individual monitored by the system, where the presence of a UTI may be predicted based on changes in the frequency of wetness events over time; and/or the likelihood, timing or characteristics of a future wetness event.

According to aspects of the disclosure, the characteristics used to characterize a wetness event by the mathematical model may include, for example: an area under a sensing element signal curve, the highest sensing element signal value in a predetermined time period, a maximum value of a leading edge of the sensing element signal, a rate of change of sensing element signal after a leading edge, a volume estimated in a previous wetness event, a time of onset of a wetness event, a time of termination of a wetness event, a duration of a wetness event, a time of day of a wetness event, a time elapsed since last wetness event, a measure of correlations between time series feature vectors determined from sensor signals and permutations of a series of predetermined template time series feature vectors (where permutations may include warping the time and/or amplitude of the template time series feature vectors), a function of present and/or past sensing element signals and or/time, and/or position of a wetness event.

According to aspects of the disclosure, a processor is configured to determine one or more of the following: a likelihood and/or the characteristics of an imminent wetness event; an estimate of when a wetness event is likely to occur; an estimate of a degree of fullness of an absorbent article; an estimate of when an absorbent article is likely to reach its absorbent capacity; the likelihood and/or characteristics of a leakage event of an absorbent article; the degree to which the wearer's skin is wet; the frequency of imminent wetness events; the type of imminent wetness events, for example, urinary incontinence, fecal incontinence, stress incontinence, or urge incontinence; the type of incontinence; the degree to which the subject is incontinent; and/or the severity of the subject's incontinence.

According to aspects of the disclosure, the user interface includes a wireless transmitter configured to transmit a signal or other notification to a user of the system to indicate a characteristic of a wetness event or potential future wetness event in an absorbent article.

Another aspect of the disclosure involves a method for analyzing characteristics of past wetness events to determine the likelihood and nature of future wetness events. Such a capability may be useful, for example, in determining the urinary voiding schedule for an individual over time. The voiding schedule may then be used by caregivers to create a toileting schedule and/or care plan for the individual.

This method may also include the use of an algorithm that takes in information related to the occurrence of wetness events and their characteristics to output a prediction of future wetness events. In accordance with aspects of this method, the algorithm also uses information related to factors such as an individual's fluid intake, health status, weight, and/or behavior to output a prediction of future wetness events.

According to aspects of the disclosure, the method includes the communication of information related to wetness events to a user based on the output of the algorithm.

According to aspects of the disclosure, the system is adapted to reconfigure the mathematical model for use with one or more of a particular individual being monitored, a different sensing element type, a different absorbent article type, and/or changes in the environment by, for example: continuously monitoring the particular individual, the different sensing element type, and/or the different absorbent article type; monitoring wetness at regular intervals by obtaining sensing element signals and obtaining observation data; and/or reconfiguring the mathematical model so that there is a satisfactory correlation between estimates produced using the sensing element signals and the reconfigured mathematical model, and observations from the observation data obtained.

According to aspects of the disclosure, the reconfiguration of a mathematical model includes application of a linear regression algorithm and/or machine learning algorithms.

According to aspects of the disclosure, the observation data includes measurements indicating an amount of wetness in the article, the weight of the article, and/or the time of measurement.

According to aspects of the disclosure, observation data includes one or more of demographic information, environmental information, and wearer information.

According to aspects of the disclosure, the system further includes one or more sensing elements for use with an article being monitored, the sensing elements including a plurality of sensing element elements arranged in a pattern which provide an improved ability to detect a given characteristic such as, for example, wetness.

According to aspects of the disclosure, the sensing element elements are arranged in a pattern in which there are more sensing element elements in regions having higher propensity for variable characteristics such as, for example, moisture and/or temperature.

According to aspects of the disclosure, one or more sensing element elements are arranged on the outside of the article, for example an absorbent article, in order to determine a characteristic on the inside of the article such as, for example, wetness of the article.

According to aspects of the disclosure, the system is configurable to adapt a mathematical model to characterize a wetness event in an absorbent article being monitored using one or more of a new sensing element type, a new sensing element, and a new type of absorbent article not previously used with the moisture monitoring system.

According to aspects of the disclosure, the processor may be is configured to automatically receive data pertaining to known features of an absorbent article selected from a group including, for example, volume capacity, type, brand, and location of sensing elements embedded therein.

It may be understood that both the foregoing general description and the following detailed description are exemplary and explanatory only, and are not necessarily restrictive of the features claimed. As used herein, the terms "comprises," "comprising," or any other variation thereof, are intended to cover a non-exclusive inclusion such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 10A and 10B are schematics describing use of capacitive sensing elements for detection, in accordance with aspects of the present disclosure.

FIGS. 11-16 show capacitive sensing circuits and/or elements, in accordance with aspects of the present disclosure.

FIGS. 22A-22C are alternative views of a device having multiple sensing elements, in accordance with aspects of the present disclosure.

FIGS. 23A-23D are diagrams showing sensing element layouts, in accordance with aspects of the present disclosure.

FIGS. 24-28 are schematics showing capacitive sensing elements in use, in accordance with aspects of the present disclosure.

FIGS. 34A-34E are top views of layers of a conductive sensing element, in accordance with aspects of the present disclosure.

FIG. 61 shows graphs of exudate volume versus impedance, and exudate volume versus phase, in accordance with aspects of the present disclosure.

FIG. 62 illustrates a schematic of an impedance measurement model, in accordance with aspects of the present disclosure.

FIGS. 65-78 are screenshots from a computing device showing a user interface, in accordance with aspects of the present disclosure.

DETAILED DESCRIPTION OF PARTICULAR EMBODIMENTS

The present disclosure is drawn to systems, devices, and related methods for incontinence management. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a wearer. By contrast, the term "proximal" refers to a portion closest to the user when placing the device into the wearer. The term "approximately," when used to describe a numerical value, may be anywhere in a range of ±5% from the numerical value.

The following description refers to terms that should be interpreted broadly to encompass known and future alternatives in the art. It will be apparent to those skilled in the art that various modifications and variations can be made in the disclosed systems, devices, and methods without departing from the scope of the disclosure. Other aspects of the disclosure will be apparent to those skilled in the art from consideration of the specification and practice of the features disclosed herein. It is intended that the specification and examples be considered as exemplary only.

System Overview

Figure 1:
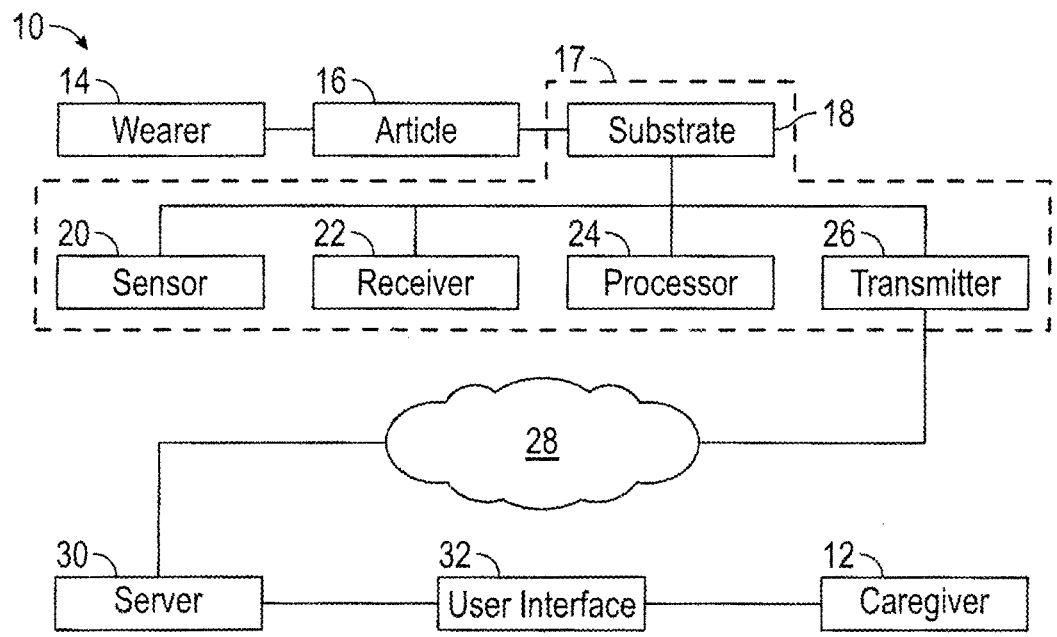
FIG. 1 is a schematic of a system for incontinence management, in accordance with aspects of the present disclosure.

FIG. 1 shows a schematic of an exemplary system 10 for incontinence management. System 10 links one or more caregivers 12 to one or more wearers 14 of one or more absorbent articles 16. System 10 includes one or more devices 17 that may be configured for coupling to absorbent articles 16. Devices 17 include one or more substrates 18 for supporting one or more sensing elements 20, receivers 22, processors 24, and transmitters 26. Sensing elements 20 are configured to sense one or more conditions associated with wearers 14, absorbent articles 16, and/or the surrounding environment. Receivers 22, processors 24, and/or transmitters 26 form part of a subsystem for gathering, processing, and/or otherwise using data from sensing elements 20. Receivers 22 are configured to receive data from sensing elements 20. The received data is then processed by processors 24. The processed data is transmitted by transmitters 26, via one or more communications links or networks 28, to one or more servers 30. Servers 30 provide the processed data to one or more user interfaces 32 for communicating the processed data to caregivers 12. Caregivers 12 perform one or more actions based thereon. Additional aspects of system 10, and methodologies that may be performed with system 10 and its constituent devices, are outlined below.

Absorbent Articles

Figure 2A:
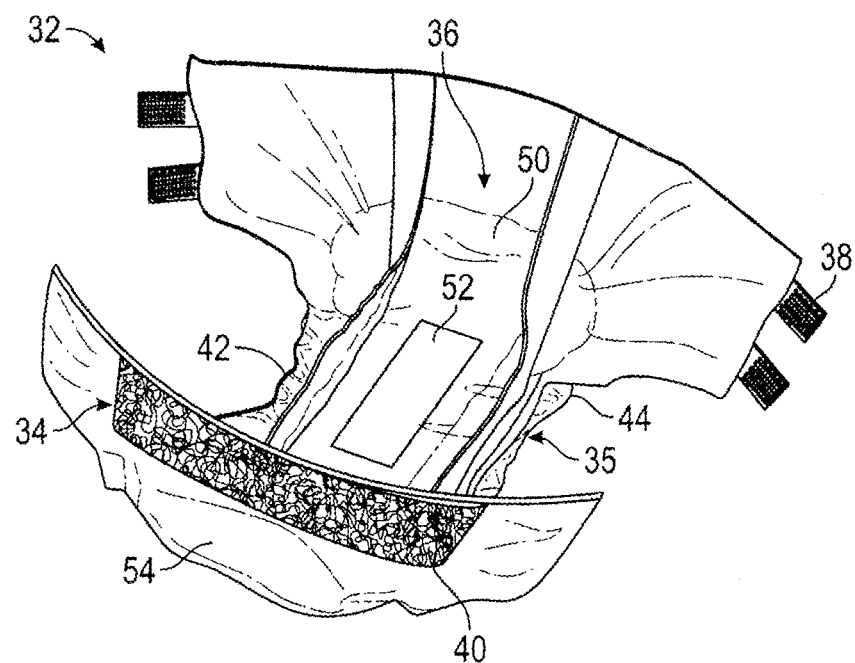
FIGS. 2A and 2B are perspective views of an absorbent article, in accordance with aspects of the present disclosure.
Figure 2B:
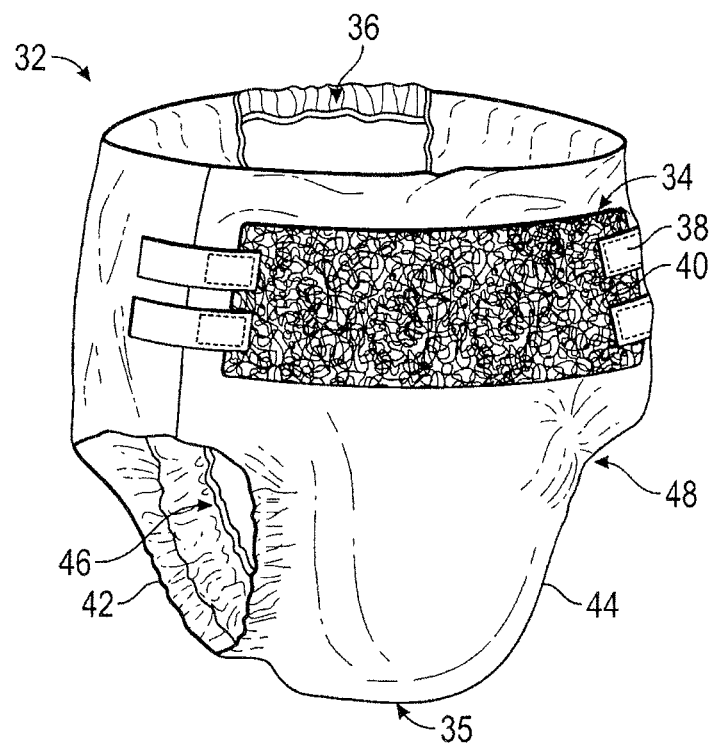

FIGS. 2A, 2B, and 3A-3C show examples of absorbent article 16 that may be worn by wearers 14. For example, FIGS. 2A and 2B show an absorbent article 32 in the form of an adult brief FIG. 2A shows absorbent article 32 in an unfolded state. FIG. 2B shows absorbent article 32 as it would look when worn by wearer 14. Absorbent article 32 includes an anterior portion 34, a posterior portion 36, and an intermediate portion 35 connecting anterior portion 34 to posterior portion 36. Anterior portion 34 and posterior portion 36 may be fastened to each other by one or more fasteners 38, 40, and when fastened, their edges 42, 44 define leg openings 46, 48 for the wearer's legs. Absorbent article 32 also includes an inner layer 50 that may come into contact with the wearer's skin when absorbent article 32 is worn, a core 52 separated from the user's skin by inner layer 50, and an outer layer 54 forming an exterior of absorbent article 32. Moisture from the wearer's urine and/or faeces are transferred to core 52 through inner layer 50, where the moisture is absorbed and stored by core 52. Outer layer 54 includes a non-woven fabric, and/or may be water resistant to prevent the moisture from leaking out of absorbent article 32.

Figure 3A:
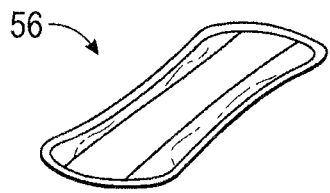
FIGS. 3A-3C are perspective views of absorbent articles, in accordance with aspects of the present disclosure.
Figure 3B:
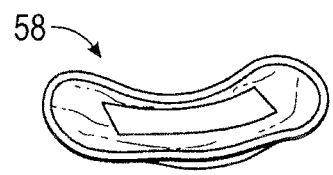
Figure 3C:
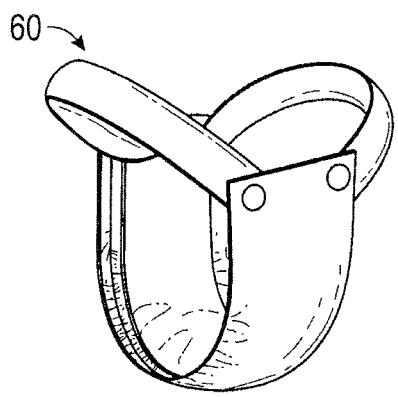

FIGS. 3A-3C show other exemplary absorbent articles. FIGS. 3A and 3B show absorbent articles 56, 58 in the form of liners or guards that may be fastened to, or otherwise supported by, a wearer's clothing for catching moisture. FIG. 3C shows an absorbent article 60 in the form of an undergarment that may be worn by a wearer. Absorbent articles 56, 58, 60 includes layers similar to those in absorbent article 32. This list of absorbent articles is not exhaustive, and it should be understood that the listed absorbent articles, and others not listed here, may be used in system 10.

Substrates

FIGS. 4A-4D show an example of one type of substrate 18 (i.e., a substrate 62 of a device 60) next to absorbent article 32. Substrate 62 may be formed, for example, of one or more layers of material, such as layers of fabric material, sewn or otherwise fastened together. Substrate 62 includes one or more surfaces and/or pockets for supporting and/or securing other components. For example, substrate 62 includes a pocket 64 for receiving transmitter 26 (FIG. 1) and/or a pocket 66 for receiving one or more sensing elements 20 (FIG. 1). Substrate 62 and/or components supported therein or thereon, may be reusable after being cleaned and sterilized.

Figure 4A:
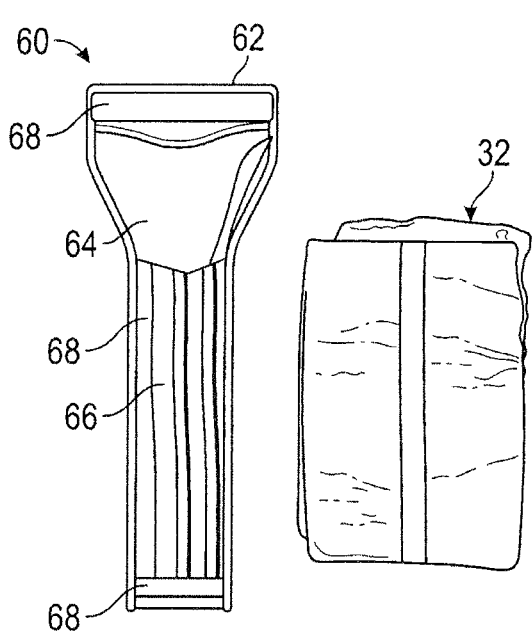
FIGS. 4A-4D are views showing steps for applying a substrate onto an absorbent article, in accordance with aspects of the present disclosure.
Figure 4B:
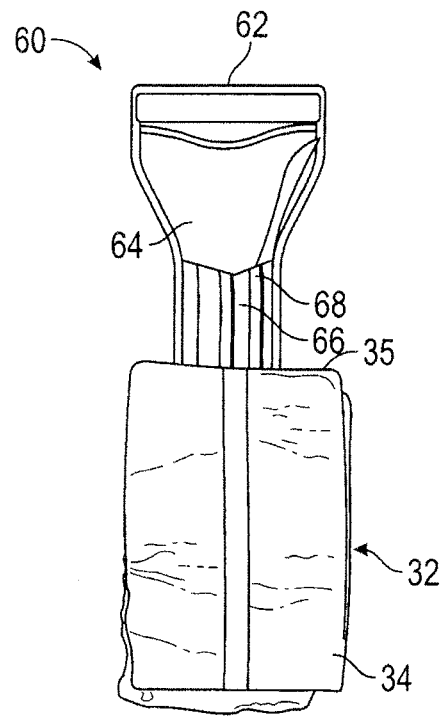
Figure 4C:
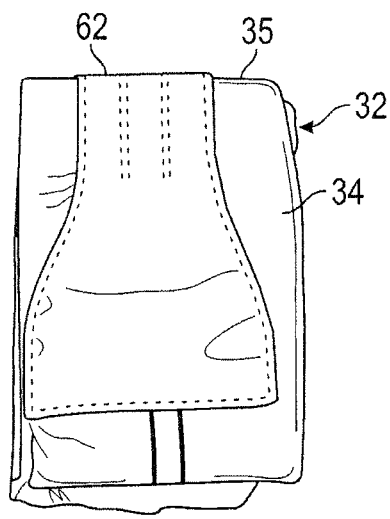

FIG. 4A shows absorbent article 32 in a folded state beside substrate 62, prior to coupling. Substrate 62 may be coupled to absorbent article 32 by being applied to the exterior of absorbent article 32 using the steps shown in FIGS. 4B and 4C. For example, as shown in FIG. 4B, a first portion of substrate 62 may be applied to the exterior of posterior portion 36 of absorbent article 32. As shown in FIG. 4C, a second portion of substrate 62 may be applied to the exterior of anterior portion 34 of absorbent article 32, such that substrate 62 wraps around intermediate portion 35 of absorbent article 32. An inner surface of substrate 62 may contact the exterior of absorbent article 32.

Figure 4D:
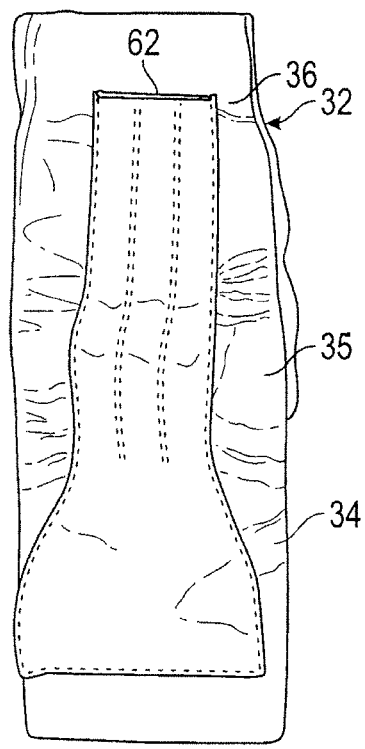

FIG. 4D shows absorbent article 32 in an unfolded state with substrate 62 applied to the underside thereof, ready for placement on a wearer. Substrate 62 may be configured for application to absorbent article 32 with absorbent article 32 in the folded state out of the view of the wearer, so the wearer does not need to be made aware of substrate 62 being put into use. Alternatively, substrate 62 may be applied to absorbent article 32 in an unfolded state prior to absorbent article 32 being placed on the wearer. Alternatively, substrate 62 may be applied to absorbent article 32 while absorbent article 32 is worn by the wearer. In any of these scenarios, the caregiver may be able to apply substrate 62 to absorbent article 32 without touching the inside of absorbent article 32 prior to placement of absorbent article 32 on the wearer.

Substrate 62 may be coupled to absorbent article 32 using any suitable fastening element or elements 68. Fastening elements 68 may be arranged in strips, or any other suitable pattern, on substrate 62. Additionally or alternatively, fastening elements 68 may be arranged along edges of substrate 62. Fastening elements 68 include, for example, one or more of hooks configured to hold onto a non-woven fabric forming outer layer 54, hook and loop fasteners, pressure adhesives, reusable adhesives, tape, pressure clips, spring-loaded clips, magnets, snap buttons, elastic straps, and/or any other suitable fastening element. It should be understood that in some of the above-listed examples, a complementary fastening element is provided on absorbent article 32. It is also contemplated that in some instances, fastening elements 68 may not puncture outer layer 54 to maintain the integrity of outer layer 54. Additionally or alternatively, substrate 62 may be removable from absorbent article 32 after use, and may be cleaned, sterilized, and then reused with another absorbent article. The positioning of substrate 62 on the exterior of absorbent article 32 may facilitate cleaning and sterilization of substrate 62 after use since substrate 62 may be isolated from a soiled interior of absorbent article 32. Substrate 62 may be cleaned and sterilized using any suitable cleaning/sterilization system, including those used for cleaning medical devices or instruments.

When removing substrate 62, the caregiver may remove absorbent article 32 from the wearer, remove the substrate 62 from absorbent article 32, and proceed with the application process described above with a replacement substrate and absorbent article. Alternatively, after removing absorbent article 32 from the wearer, substrate 62 and absorbent article 32 may be disposed of together. Alternatively, the caregiver may remove substrate 62 while absorbent article 32 is being worn by the wearer.

Figure 5:
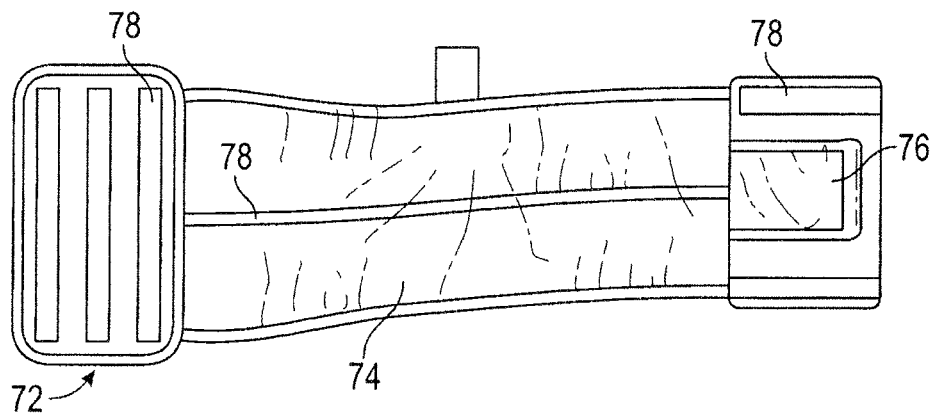
FIGS. 5-9 are various views of alternative substrates, in accordance with aspects of the present disclosure.

FIG. 5-9 show alternative examples of substrate 18. FIG. 5 shows a substrate 72. Substrate 72 is formed of one or more layers of material forming a pocket 74 and/or a pocket 76, similar to substrate 62. Substrate 72 includes one or fastening elements 78 similar to fastening element 68. Substrate 72 is differently sized and/or shaped from substrate 62. For example, portions of substrate 72 are longer and/or wider than corresponding portions of substrate 62, such that substrate 72 may be used on a larger absorbent article, or may be used on absorbent article 32 while covering more of the exterior of absorbent article 32 than substrate 62. Additionally or alternatively, substrate 72 is shaped so as to contact areas of absorbent articles that are not contacted by substrate 62.

Figure 6:
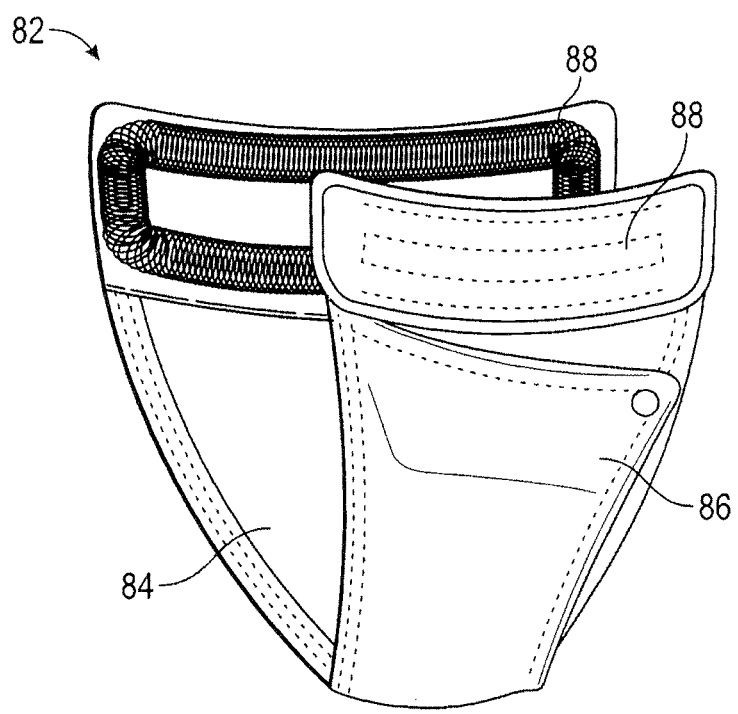

FIG. 6 shows another substrate 82. Substrate 82 is formed of one or more layers of material forming a pocket 84 and/or a pocket 86, similar to substrate 62. Pocket 86 may be opened from an exterior side of substrate 82. Substrate 82 includes one or fastening elements 88 similar to fastening element 68 (FIG. 4A). Fastening elements 88 are provided at ends of substrate 82, and are used to couple substrate 82 to the exterior of an absorbent article like absorbent article 32, such that the interior of substrate 82 contacts the exterior of the absorbent article.

Figure 7:
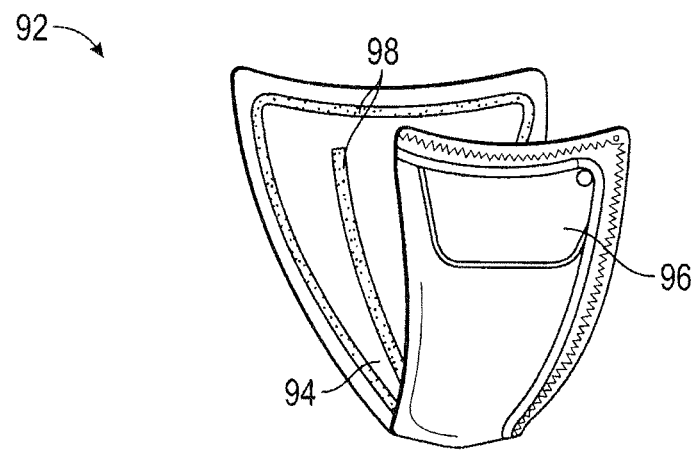

FIG. 7 shows another substrate 92. Substrate 92 is formed of one or more layers of material forming a pocket 94 and/or a pocket 96, similar to substrate 62. Pocket 96 may be opened from an exterior side of substrate 92. Substrate 92 includes one or fastening elements 98 similar to fastening element 68 (FIG. 4A). Fastening elements 98 extend around a perimeter of substrate 92 and/or along a central region of substrate 92, and are used to couple substrate 92 to the exterior of an absorbent article like absorbent article 32, such that the interior of substrate 92 contacts the exterior of the absorbent article.

Figure 8:
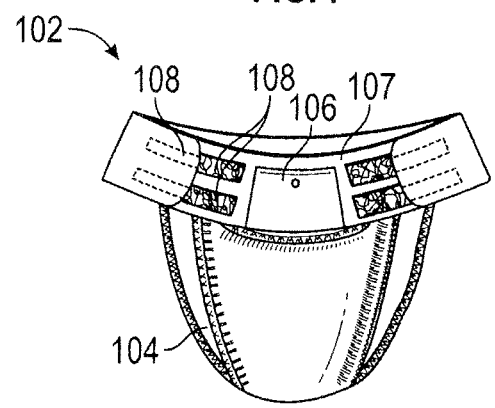

FIG. 8 shows another substrate 102. Substrate 102 is formed of one or more layers of material forming a pocket 104 and/or a pocket 106, similar to substrate 62. Pocket 106 may be opened from an exterior side of substrate 102. Substrate 102 includes a waistband 107 for securing around the waist of a wearer, and one or fastening elements 108 similar to fastening element 68 (FIG. 4A) for adjusting a circumference of waistband 107 to fit the wearer. Substrate 102 may be worn by the wearer outside of an absorbent article like absorbent article 32, such that the interior of substrate 102 contacts the exterior of the absorbent article.

Figure 9:
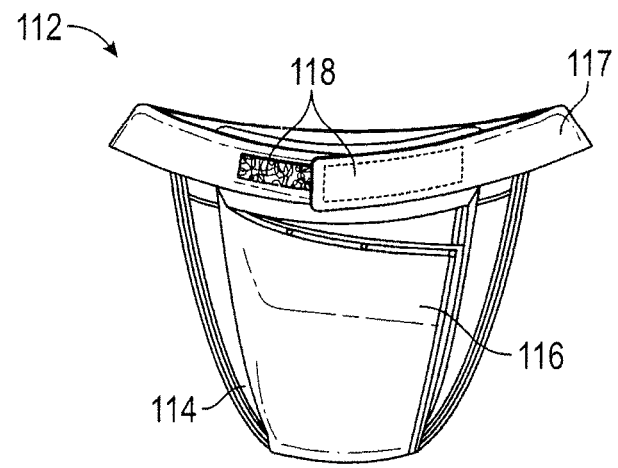

FIG. 9 shows another substrate 112 of a device 110. Substrate 112 is formed of one or more layers of material forming a pocket 114 and/or a pocket 116, similar to substrate 62. Pocket 116 may be opened from an exterior side of substrate 112. Substrate 112 includes a waistband 117 for securing around the waist of a wearer, and one or fastening elements 118 similar to fastening element 68 (FIG. 4A) for adjusting a circumference of waistband 117 to fit the wearer. Substrate 112 may be worn by the wearer outside of an absorbent article like absorbent article 32, such that the interior of substrate 112 contacts the exterior of the absorbent article.

Overview of Sensing Elements

Referring to FIG. 1, system 10 monitors one or more characteristics of absorbent article 16 and/or its wearer 14 using one or more sensing elements 20. Sensing elements 20 generate one or more signals indicative of the characteristics of absorbent article 16 and/or wearer 14. Sensing elements 20 are positioned on or within substrate 18, such that sensing elements 20 may be in contact with or in close proximity to the outside of absorbent article 16. This positioning allows system 10 to monitor absorbent article 16 and/or wearer 14 from outside absorbent article 16. For example, this positioning allows system 10 to monitor moisture levels within absorbent article 16 from outside article 16, and to infer wetness events from the sensing element signals generated by sensing elements 20. Further, by positioning sensing elements 20 external to absorbent article 16, sensing elements 20 may detect wetness events, wetness states, and/or other characteristics without making direct contact with the moisture contained in article 16. Exemplary sensing elements 20 for use external to absorbent article 16, as well as those used inside of absorbent article 16, will be described in more detail below.

Capacitive Sensing

One or more capacitive sensing elements are used in system 10. Capacitive sensing elements use capacitive sensing to characterize wetness events and/or other characteristics of absorbent articles and/or wearers. Capacitive sensing has many applications. For example, capacitive sensing may be used in touch screens to detect user touches. Capacitive sensing elements can sense the electrical capacitance of objects from a distance away from the objects, such that direct contact between the sensing elements and the objects is not required. Capacitive sensing elements may also be able to sense the electrical capacitance of objects through one or more layers of other material.

FIGS. 10A and 10B show an exemplary schematic of how one or more capacitive sensing elements 119 are used to detect characteristics of absorbent articles 16. As shown, capacitive sensing elements 119 are positioned outside of absorbent article 16, for example near, at, or on an exterior of absorbent article 16, such that capacitive sensing elements 119 are separated from the interior of absorbent article 16. The separation is provided by one or more layers of material including, for example, outer layer 54 of absorbent article 32, and/or the material forming pockets of the above-described substrates 18. Capacitive sensing elements 119 are able to detect a characteristic of absorbent article 16 through the layer(s) of material. The detected characteristic includes the capacitance of absorbent article 16. Moisture 121 from exudate (e.g., urine and/or faeces) of wearer 14 may be absorbed in the interior of absorbent article 16. This absorption changes the capacitance of absorbent article 16. Information on characteristics of the exudate 121 and/or absorbent article 16 may be gleaned from analyzing the signals from capacitive sensing elements 119.

An exemplary schematic of a capacitive sensing circuit 120, configured to detect a capacitance 122 of an object, such as absorbent article 16, wearer 14, exudate 121 from wearer 14, and/or combinations thereof is depicted in FIG. 11. Circuit 120 includes, for example, a signal generator 124, internal components for voltage division measurement (e.g., a resistor 126), and an input 128. A processor, such as processor 24 (FIG. 1), controls operation of signal generator 124. Input 128 includes an analog to digital conversion performed by a microcontroller (not shown). The processor monitors input 128, and estimates capacitance 122 based at least partially thereon. Circuit 120 also includes one or more electrical grounds 130, 132. The grounds 130, 132 include, for example, a human ground, a device ground, and/or an external ground. Grounds 130, 132 of circuit 120 also function as grounds of system 10. In circuit 120, the object whose capacitance 122 is detected is insulated from circuit 120.

Figure 13:
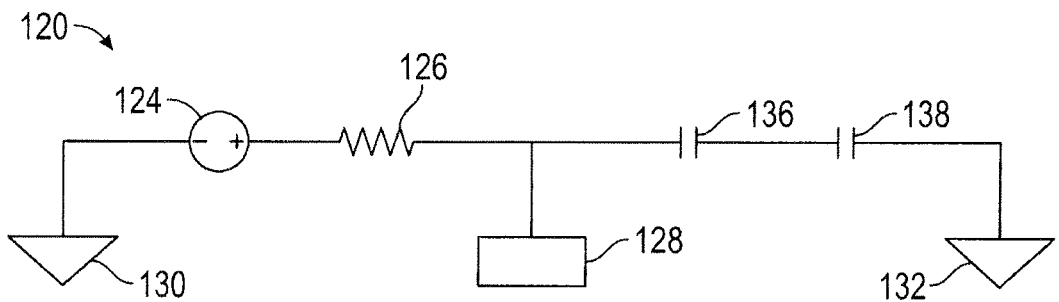
Figure 14:
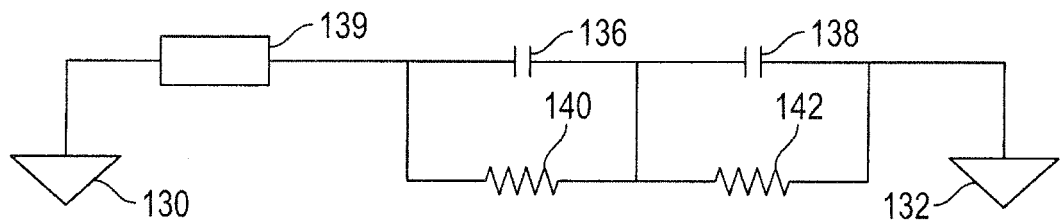

FIG. 12 shows another schematic of an exemplary capacitive sensing circuit 134, configured to detect a capacitance 136 of absorbent article 16 and/or exudate 121 from wearer 14, and a capacitance 138 of wearer 14. Capacitances 136, 138 impact the signal measured by an assembly 139. As shown in FIG. 13, assembly 139 includes signal generator 124, resistor 126, and input 128. A change in the signal voltage of signal generator 124, and the input signal, is used to infer capacitances 136, 138. In circuit 134, there is a degree of conductivity between absorbent article 16 and wearer 14. This scenario arises, for example, when exudate emitted by wearer 14 overflows or leaks over an edge of absorbent article 16. FIG. 14 shows the scenario of FIG. 12 with the addition of resistors or resistances 140, 142 in parallel with capacitances 136, 138. These resistances 140, 142 are typically high values (>1 megaohm, as an example) and may represent the parallel resistances of absorbent article 16 and wearer 14. Resistance 140 of absorbent article 16 may typically be high because of the resistance of a waterproof (non-conductive) layer of material of absorbent article 16. Resistance 142 of wearer 14 may typically be high because the resistance of unsaturated skin may typically be high, and wearer 14 only makes conductive contact with absorbent article 16 where wearer 14 physically touches absorbent article 16. The extent of physical contact between wearer 14 and absorbent article 16 may vary significantly, which may hinder the creation of a high conductivity connection.

Figure 15:
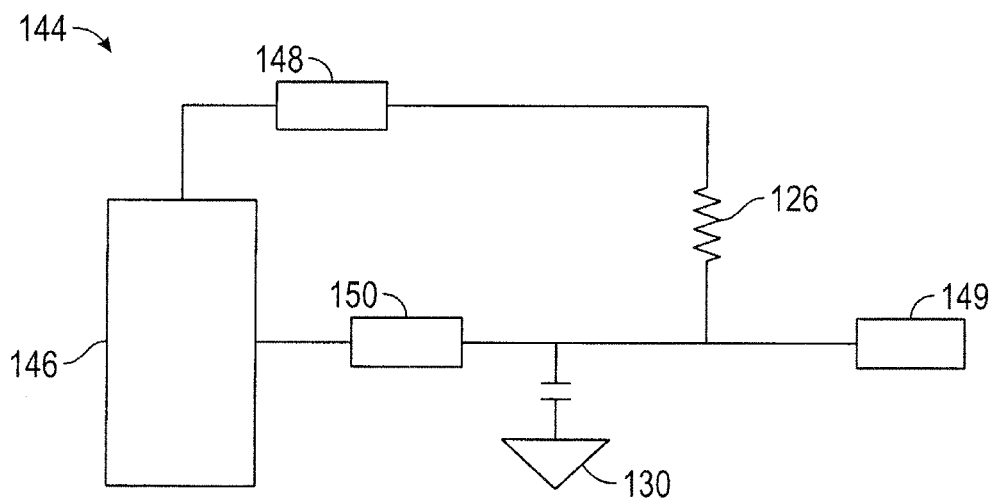

FIG. 15 shows a circuit diagram for an exemplary capacitive sensing element 144. Sensing element 144 includes a microcontroller 146. Microcontroller 146 includes, take the place of, or otherwise control signal generator 124 and/or input 128. Microcontroller 146 includes an output pin 148 and one or more input pins 150. One or more output signals from microcontroller 146 may be sent out via output pin 148 to the rest of sensing element 144, which includes resistor 126 and a capacitive sensing element plate 149. One or more signals from resistor 126 and capacitive sensing element plate 149 may be received by microcontroller 146 via input pin 150. For example, a time between initiation of a step function applied to output pin 148 and a time to rise of input pin 150 may be measured by microcontroller 146. Due to capacitive effects induced by capacitive sensing element plate 149, the rise time of input pin 150 increases when capacitive material is in the proximity of capacitive sensing element plate 149. The rise time of input pin 150 may be used to estimate the capacitance and/or presence of capacitive bodies. Exudate in absorbent article 16 is one such capacitive body.

Figure 16:
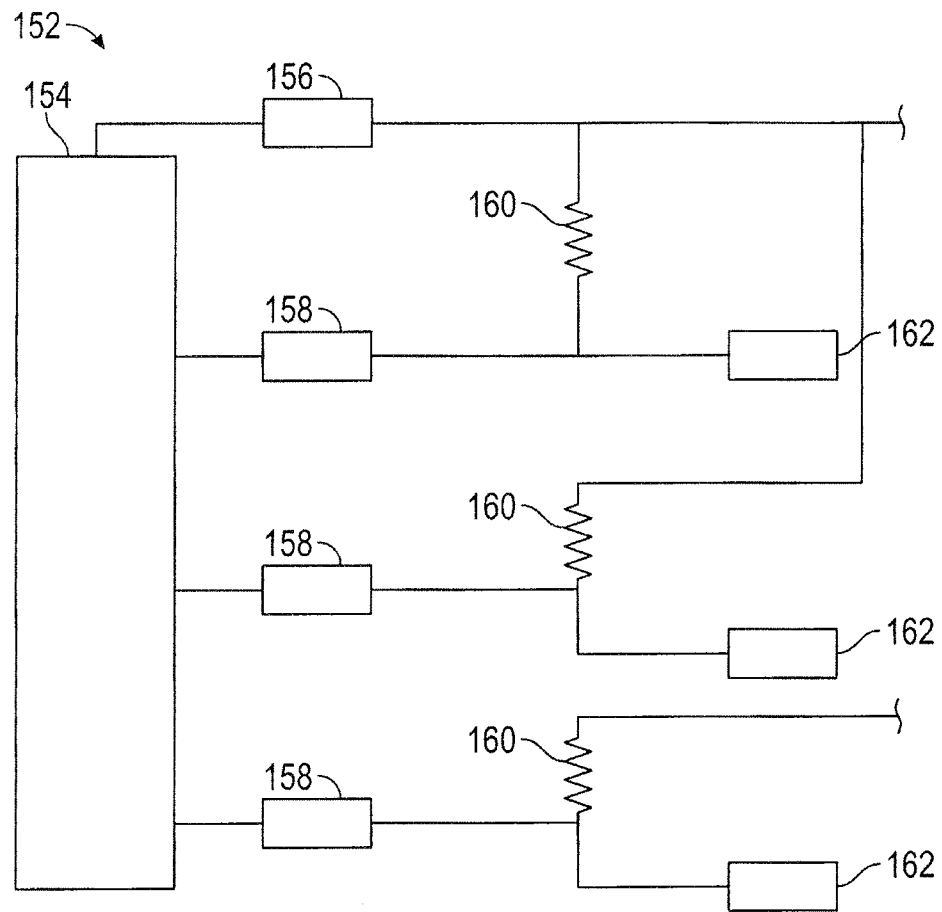

FIG. 16 shows another circuit diagram for an exemplary capacitive sensing element 152. Sensing element 152 includes a microcontroller 154 having an output pin 156 and one or more input pins 158, similar to microcontroller 146, output pin 148, and input pins 150. Microcontroller 154 may send signals to one or more resistors 160 and one or more capacitive sensing element plates 162 via output pin 148, and may receive signals therefrom via input pins 150. While three resistor-capacitive plate pairings are shown, it should be understood that any number of pairings may be provided depending on the number of readings desired. This circuit diagram allows for multiple capacitive sensing element plates 162 with a single output pin 156.

In the above-described circuits, changes in the capacitance of absorbent article 16 and/or wearer 14 may be monitored to obtain an estimate of one or more characteristics of wetness events on or in the vicinity of absorbent article 16. While a few circuits have been described above, it should be understood that any other suitable circuits may be used.

Additionally or alternatively, a capacitive sensing method using the above-described circuits includes feeding a multitude of frequencies to one or more of the capacitive plates. Capacitive measurements may be taken to characterize moisture in absorbent article 16. The response of absorbent article 16 and/or material absorbed therein changes with frequency, and measuring the capacitance on multiple frequencies provides additional information that may be used to characterize wetness events. One example of a frequency generating and/or monitoring component is a processor, in the form of a microcontroller or other analog circuitry.

Figure 17A:
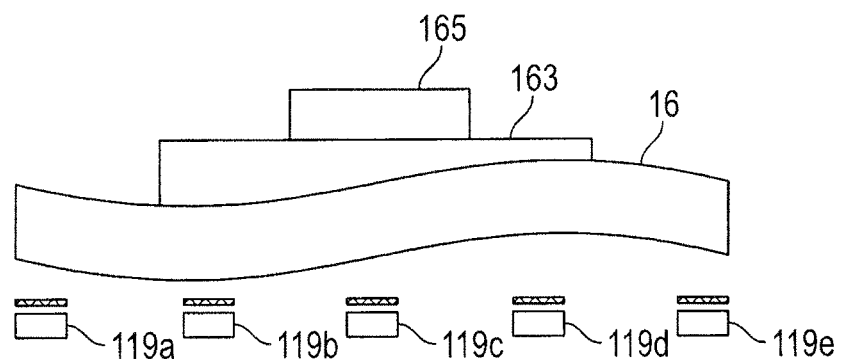
FIGS. 17A-17C illustrate aspects of volume estimation, in accordance with aspects of the present disclosure.

In addition to identifying the occurrence of wetness events in absorbent article 16, system 10 may perform one or more techniques that may be employed to estimate the volume of exudate in absorbent article 16. For example, the volume may be estimated by counting the number of capacitive sensing elements in system 10 having a saturation value above a certain threshold. FIG. 17A illustrates absorbent article 16 with a damp region 163. A volume estimation algorithm determines a saturation value for each of capacitive sensing elements 119a-119e, wherein each of the saturation values correspond to the saturation level of a region of absorbent article 16 at or above one of capacitive sensing elements 119a-119e after the region has been exposed to exudate and/or liquid. For each of capacitive sensing elements 119a-119e that is at saturation, the algorithm adds a volume to a volume estimate. The volumes added are specific to each of capacitive sensing elements 119a-119e, and correspond with the region of absorbent article 16 each of capacitive sensing elements 119a-119e is responsible for monitoring. The volume estimate generated by the algorithm is, for example, the sum of the individual volume contributions from each of capacitive sensing elements 119a-119e. In the example depicted in FIG. 17A, only capacitive sensing elements 119b-119d are at saturation. Thus, the volume is estimated by adding the volumes associated with capacitive sensing elements 119b-119d, and not adding the volumes associated with capacitive sensing elements 119a, 119e.

Additionally or alternatively, the volume estimation can be extended to look at surface moisture 165. The steps may include determining a surface moisture value for each of capacitive sensing elements 119a-119e. The surface moisture value of a capacitive sensing element may correspond to a degree of surface moisture in a region of absorbent article 16 monitored by the capacitive sensing element. Surface moisture can be differentiated from dampness because the capacitive values measured with surface moisture present may be much higher than for just dampness. A subsequent step may include determining the volume estimate using the above-described saturation volume method. Another subsequent step may include modifying the estimated volume by adding additional volumes as a result of surface moisture.

Figure 17B:
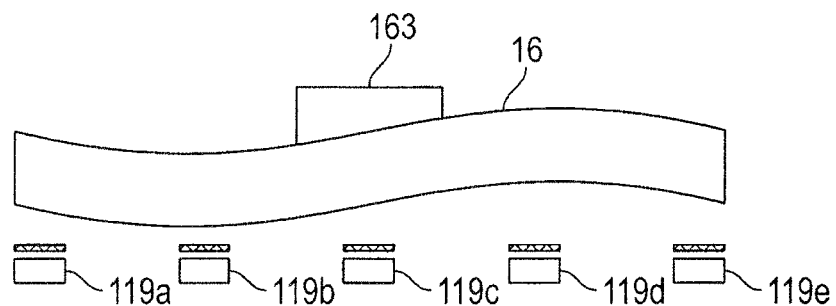
Figure 17C:
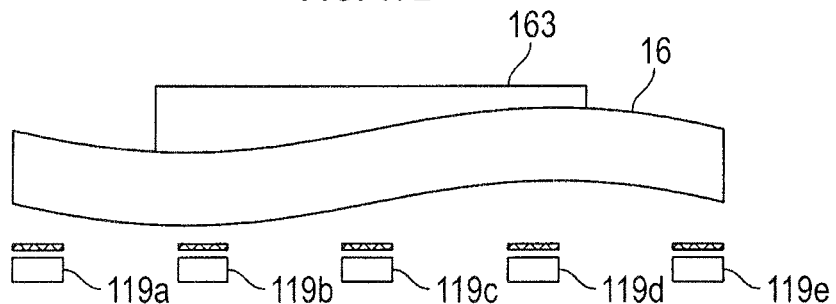

Additionally or alternatively, volume estimation can be performed by looking at the rate of dispersal of saturation and/or surface moisture through absorbent article 16. An example of this is illustrated in FIGS. 17B, 17C. At a time t1 (FIG. 17B) after the start of a wetness event, one capacitive sensing element 119c is saturated. At a time t2 (FIG. 17C) capacitive sensing elements 119b-119d are saturated. A volume estimation may be determined by estimating the volume using one of the methods described above or another method at the time t1, and at the later time t2, estimating the volume again. Then, the rate change of volume may be calculated. Using the rate of change of volume, the volume estimate at one or more later times, and potentially other inputs (for example surface dampness, demographic information, type of urinary incontinence, physical arrangement/locations of capacitive sensing elements 119a-119e), the volume estimate may be updated to account for fluids that have not yet spread across absorbent article 16 and saturated other capacitive sensing elements 119a, 119e.

Additionally or alternatively, a more general function may be applied, and neural networks may be used to determine the function. In that scenario, the neural network can be trained with the measured volume in as the target and the interference reduced capacitive sensing element values as the inputs.

Additionally or alternatively, a very general neural network may be used to determine a mapping between the volume and capacitive sensing elements 119a-119e and/or other sensing elements 120 (e.g., pressure sensing elements). In that scenario, the neural network may be trained with the measured volume as the target and one or more of the sensing element values as inputs.

It is also contemplated that system 10 may run an algorithm to analyze the sensing element signals by applying the sensing element signals to a predetermined mathematical model. The mathematical model may characterize wetness events in absorbent article 16 in terms of location of the exudate, remaining capacity of absorbent article 16, chance that a leak has occurred, chance of a leak occurring in the near future, and/or other wetness event characteristics. The mathematical model may take, as inputs, one or more characteristics, including wetness state of absorbent article 16, location of absorbent article 16, size/volume of recent wetness events, time of recent wetness events, duration of absorbent article 16 at a given wetness state, type of absorbent article 16, demographic information of wearer 14, change history of wearer 14, and/or activity history of wearer 14, to name just a few.

In one aspect, sensing elements 20 include a plurality of sensing elements supported on or in one of the above-described substrates 18, and also include transmitter 26 that is supported on or in the substrates 18 (e.g., placed within a pocket of any of the substrates 18). Substrate 18 may, for example, be applied to the underside of absorbent article 16, allowing wetness events inside absorbent article 16 to be monitored using sensing elements 20.

Interference

Figure 18:
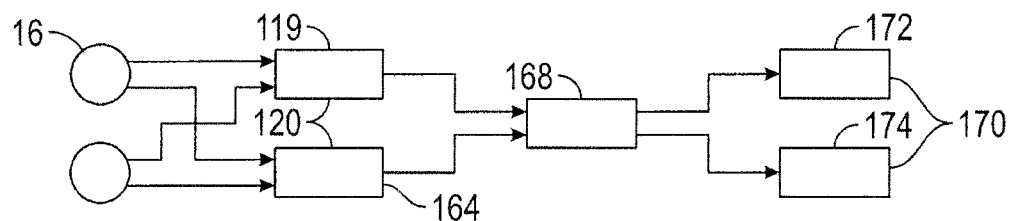
FIG. 18 is a system flowchart, in accordance with aspects of the present disclosure.

With reference to FIG. 1, system 10 may be subject to one or more forms of interference that may impact its ability to accurately detect, monitor, and/or characterize wetness events. As shown by the flowchart in FIG. 18, changes associated with absorbent article 16 affect signals associated with sensing elements 20, which include, in this example, capacitive sensing elements 119 (FIGS. 10A, 10B) and other sensing elements 164. The affected signals may be monitored by system 10, and characteristics associated with absorbent article 16 may be inferred therefrom. In some instances, interference 166 also affects the sensing element signals. The interference may, for example, stem from wearer positioning and/or movement, and/or external sources. By reducing the interference, the performance of system 10 is enhanced. System 10 may include aspects and/or steps for reducing interference 168. Such aspects and/or steps produce more accurate outputs 170, which include, in this example, an estimation 172 of the volume of moisture in absorbent article 16, and a characterization 174 of the wetness event in absorbent article 16.

Figure 19:
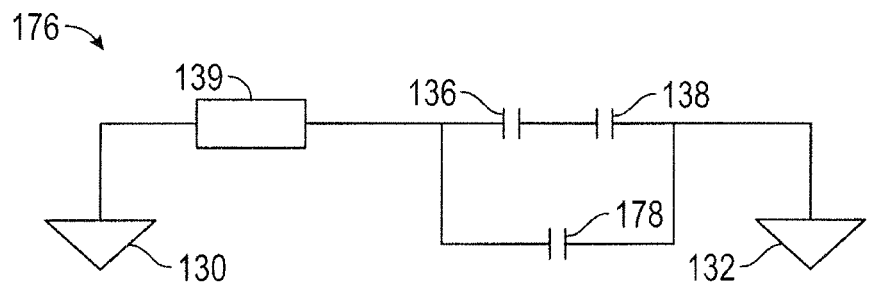
FIGS. 19 and 20 are schematics for capacitive sensing circuits, in accordance with aspects of the present disclosure.

One source of interference may result from the positioning and/or movement of wearer 14. A schematic of an exemplary capacitive sensing circuit 176 is shown in FIG. 19, which includes aspects similar to circuit 134 (FIG. 12). An additional source of capacitance 178 is shown in circuit 176, and is indicative of the presence of one or more body parts (e.g., legs, hands, and/or genitalia) of wearer 14. Capacitance 178 produces interference for system 10 as it attempts to characterize wetness events in absorbent article 16 based on capacitances 136, 138. Movement of the body parts, which may change capacitance 178, may present further difficulties.

Figure 20:
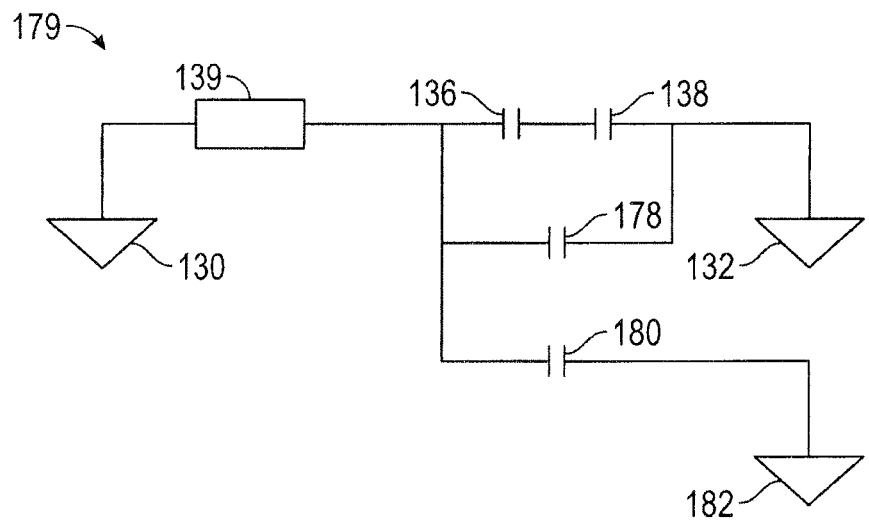

FIG. 20 shows a schematic of another exemplary capacitive sensing circuit 179 that includes aspects similar to circuit 176. Another additional source of capacitance 180 is shown in circuit 177. Capacitance 180 is indicative of the presence of one or more external conductors (e.g., a wheelchair, bed frame, metal chair, damp bed linens, and/or other electronic equipment) in the vicinity of wearer 14 and/or absorbent article 16, that may also impact the response of device 17. The external conductors are grounded by an external ground 182.

The interference caused by movement and/or positioning of wearer 14, and/or the presence of external conductors, are reduced by shielding one or more of sensing elements 20 from external influence. Additionally or alternatively, the interference may be monitored and/or reduced by physically or operationally combining one of sensing elements 20 with other sensing elements. The additional sensing elements may include, but are not limited to, capacitive sensing elements, pressure sensing elements, temperature sensing elements, accelerometers, gyroscopes, magnetometers, barometric pressure sensing elements, vibration sensing elements, magnetic sensing elements (e.g., a reed switch or reed relay), flex sensing elements, optical sensing elements (e.g., color sensing elements or photoresistors, infrared sensing elements, and/or any suitable optical sensing element for sensing a change in a strip of color-changing material on absorbent article 16 or device 17 that may change color when exposed to exudate), humidity sensing elements, chemical sensing elements, and/or heat flux sensing elements.

According to one aspect, the interference is reduced by using an algorithm that takes into account at least some of the information from sensing elements 20. For example, the algorithm may take into account information from one or more capacitive sensing elements 119, and one or more additional sensing elements. The algorithm may also take into account demographic and environment information, and historic state information. One exemplary algorithm uses the general function f below to generate a reduced interference capacitive sensing element value:

> reduced interference capacitive sensing element value=$f$(capacitive sensing element value(s), additional sensing element value(s), demographic information, environmental information, historic state information)

Additional or alternative algorithms will be described in the sections below.

Pressure Sensing

Figure 21A:
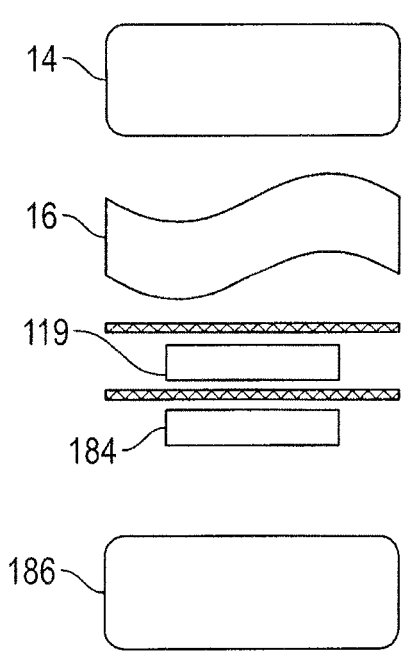
FIGS. 21A and 21B are diagrams showing a source of interference, in accordance with aspects of the present disclosure.
Figure 21B:
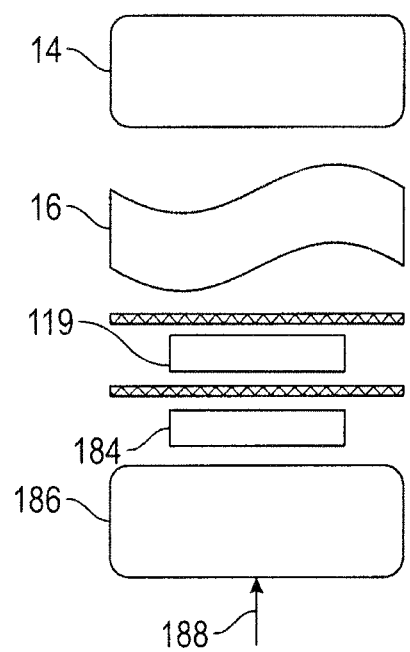

According to one aspect, external and/or human interference are reduced by using one or more pressure sensing elements 184 in conjunction with capacitive sensing elements 119. FIGS. 21A, 21B show diagrams indicative of how body parts of wearer 14 may produce interference. For example, capacitive sensing element 119 is positioned in or on article 16 to sense the capacitance of article 16 and/or wearer 14, and produces readings or values indicative of the sensed capacitance. When wearer 14 moves his or her leg 186 toward capacitive sensing element 119 (see directional arrow 188), leg 186 may change the capacitance sensed by capacitive sensing element 119, thus hindering the capacitive sensing element's ability to accurately sense the capacitance of article 16 and/or wearer 14 by affecting the capacitive sensing element's readings or values. While leg 186 is shown here, it should be understood that any conductive body part (e.g., a hand or arm) and/or any conductive external object (e.g., a piece of medical equipment) may cause similar interference. Pressure sensing elements 184 may, for example, produce readings or values indicative of the pressure applied by leg 186 on absorbent article 16 and/or device 17. The pressure readings or values may be used to identify one or more characteristics of the interference produced by leg 186, and/or may be used to adjust the readings or values from capacitive sensing element 119 to reduce, remove, or otherwise mitigate the interference.

According to one aspect, an algorithm reduces interference at capacitive sensing element 119, caused by the positioning and/or movement of a wearer's leg, using one or more readings from pressure sensing element 184. One exemplary algorithm for determining the reduced interference capacitive sensing element value is:

> reduced interference capacitive sensing element value=capacitive sensing element value+ $m$*pressure sensing element value In the algorithm above, m represents a constant determined through experimentation and/or by analyzing historical data and trends. Additionally or alternatively, any other suitable techniques may be employed to determine m, including regression analysis and/or machine learning.

According to one aspect, a plurality of pressure sensing elements 184 are used, and the algorithm reduces the interference on each capacitive sensing element 119 by the summation of each of the pressure sensing element values multiplied by its own individual slope.

Additionally or alternatively, capacitive sensing element values may be modified by a combination of one or more of a summation of each of the pressure sensing element values multiplied by its own constant, and summation of general functions of pressure sensing element values and capacitive sensing element values multiplied by their own constants, to reduce interference.

A multiple regression process may be employed to determine the constants (e.g., slopes) of the sensing element values and functions of the sensing element values. The multiple regression process may include one or more steps. An initial step may include, for various volumes of exudate, collecting pressure sensing element data and capacitive sensing element data (each volume amount, from 0 ml and up, may have its own set of data). A subsequent step may include, for each capacitive sensing element, running a regression to determine constants. Running the regression may include setting, as a Y input, capacitive sensing element values over a dataset, using the same volume of exudate for the entire dataset. Running the regression may also include creating multiple X input datasets. Exemplary X input datasets may include one X input per pressure sensing element input, and/or one X input per function of pressure sensing element input. Another subsequent step may include running multiple regression to determine the impact each pressure sensing element and the functions of the pressure sensing element values should have on each capacitive sensing element. In a linear regression method, these may be in the form of slopes m1, m2, etc. Modified capacitor values can be determined by taking original capacitor values c and adding all of the slopes multiplied by their associated pressure sensing element values or functions of pressure sensing element values.

Each capacitive sensing element 119 may have a set of slopes for each of the pressure sensing element values and the functions of pressure sensing element values. Another subsequent step may include, for each capacitive sensing element 119, removing a contribution of the pressure sensing element inputs and functions of the pressure sensing element inputs with small slopes as compared to other inputs. The small slopes may indicate that the inputs have little interfering influence on the capacitive sensing element. Another subsequent step may include re-running the regression with the limited set of the pressure sensing element inputs and functions of the pressure sensing element inputs.

Examples of functions of pressure sensing element inputs may include: a product of a pressure sensing element value and a logistic function of another sensing element value, polynomials of pressure sensing element values, products of two pressure sensing element values, exponentials of pressure sensing element values, a product of a sensing element value and multiple logistic functions of multiple pressure sensing element values, and/or a product of a sensing element value and the logistic function of any other function (this may also happen recursively). It is also contemplated that logistic functions may be replaced by step functions for simplicity. Constants associated with logistic functions may be determined through optimization methods.

The process for determining constants other than linear regression slopes may include selecting a set of constants for everything outside of the multiple regression. The process may also include determining an accuracy parameter. A suitable accuracy parameter may be an R2 difference produced by the linear regression, or a maximum deviation of an estimated volume using volume estimation techniques described below. The process may also include applying a function f(non-multiple regression constants), and various optimization techniques on the functions, including selecting constants, running regression, producing one or more accuracy parameters (e.g., R2 from multiple regression), and adjusting constants using a discrete multivariable optimization technique. Some examples of methods are simulated annealing or quasi-newton methods.

Additionally or alternatively, a more general function may be applied, and/or neural networks may be used to determine the function. In that scenario, the neural network may be trained with capacitive sensing element values as targets and pressure sensing element values as inputs.

According to one aspect, capacitive sensing element values (before and/or after modification from other methods) are modified to reduce interference optionally by the techniques described above, and/or by multiplying the sensing element values by a scaling factor determined from capacitive sensing element values and other sensing element values.

Constants used in algorithms for the summation techniques and for the general functions may be determined using various methods. These methods may include, but are not limited to, linear regression, multiple regression, minimizing error between the characterized wetness events and measured characteristics of the wetness events, and machine learning.

Figure 22A:
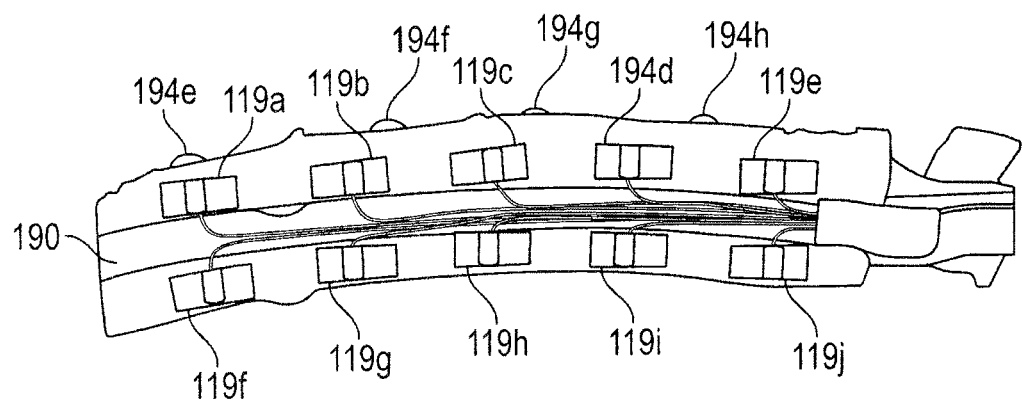

According to one aspect, as shown in FIG. 22A, device 17 includes a plurality of capacitive sensing elements 119*a*-119*j* for characterizing wetness events on or in the vicinity of absorbent article 16. Capacitive sensing elements 119*a*-119*j* are arranged in a predetermined pattern on a first side of a base 190. For example, capacitive sensing elements 119*a*-119*j* are arranged in rows and columns. Each row extends lengthwise along a lateral edge of base 190. Each column is formed by a pair of capacitive sensing elements 119*a*-119*j* that extend widthwise from one lateral edge of base 190 to the other. The rows and columns are linear, such that capacitive sensing elements 119*a*-119*j* form a grid. It should be understood, however, that any other suitable predetermined pattern or layout may be used. The first side of base 190 may be the side that faces the exterior of absorbent article 16 when device 17 is applied to absorbent article 16. While ten capacitive sensing elements 119*a*-119*j* are shown in FIG. 21A, it should be understood that fewer or more may be used.

Capacitive sensing elements 119*a*-119*j* may include capacitive sensing plates made, for example, of a conductive fabric and copper tape. Additional or alternative materials may also be used. One or more wires 192 may connect sensing elements 119*a*-119*j* to, for example, receiver 22, processor 24, and/or transmitter 26. Wires 192 may extend longitudinally along a centerline of base 190. In one example, each of sensing elements 119*a*-119*j* may be connected to receiver 22, processor 24, and/or transmitter 26 by its own individual wire(s) 192. Each of capacitive sensing elements 119*a*-119*j* may operate individually, such that if one or more of them ceases to operate, the remaining ones may remain operational.

Capacitive sensing elements 119*a*-119*j* may be adhered, sewn, embedded in, or otherwise attached to base 190. Base 190 may be adhered to, sewn, or otherwise secured in or to substrate 18, such that capacitive sensing elements 119*a*-119*j* may be positioned on the side of substrate 18 that may rest against the bottom outer surface of absorbent article 16 when substrate 18 is applied to absorbent article 16. Base 190 may be made of a flexible and/or lightweight foam material.

Figure 22B:
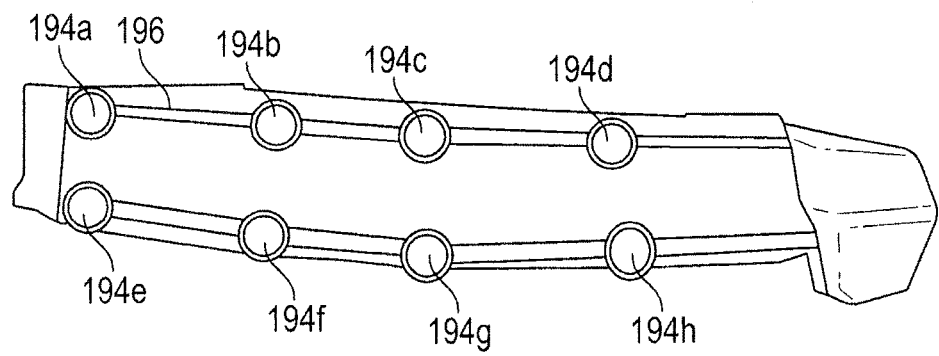

One or more pressure sensing elements 194a-194h may be positioned on a second side of base 190, the second side being opposite the first side. Pressure sensing elements 194a-194h may be arranged in a predetermined pattern on the second side of base 190. For example, pressure sensing elements 194a-194h may be arranged in rows and columns, similar to capacitive sensing elements 119a-119j. It should be understood, however, that any other suitable predetermined pattern or layout may be used. While eight pressure sensing elements 194a-194h are shown in FIG. 22B, it should be understood that fewer or more may be used. One or more wires 196, which may be similar to wires 192, may connect pressure sensing elements 194a-194h to, for example, receiver 22, processor 24, and/or transmitter 26. Each of pressure sensing elements 194a-194h may operate individually, such that if one or more of them ceases to operate, the remaining ones may remain operational. Pressure sensing elements 194a-194h may be adhered, sewn, embedded in, or otherwise attached to base 190. Pressure sensing elements 194a-194h may include, for example, conductive fabric pressure sensors that include layers of conductive fabric and anti-static plastic. Alternatively, any suitable pressure sensing elements may be used. In use, pressure sensing elements 194a-194h may be positioned at the side of substrate 18 that may face away from absorbent article 16.

As shown in FIG. 22C, base 190 acts as a spacer separating capacitive sensing elements 119a-119j from pressure sensing elements 194a-194h. Additionally or alternatively, base 190 may act as a spacer separating wires 192 from wires 196. Base 190 may maintain a relatively constant distance between the aforementioned sensing elements and/or wires.

FIGS. 23A-23D are schematic diagrams showing exemplary sensing element layouts. Capacitive sensing element positions 198 are identified with circles, and pressure sensing element positions 200 are identified with diamonds. The depicted layouts may be used on any suitable type of substrate 18, for use on any suitable type of article 16. In these diagrams, the substrate includes a pad 202. Capacitive sensing element positions 198 are one side of pad 202, while pressure sensing element positions 200 are on an opposite side of pad 202. While only four exemplary sensing element layouts are shown, it should be understood that other sensing element layouts are possible.

Capacitive sensing element positions 198 may alternate with pressure sensing element positions 200 along the length of pad 202. Additionally or alternatively, multiple columns of alternating capacitive sensing element positions 198 and pressure sensing element positions 200 may extend along the length of pad 202. Additionally or alternatively, capacitive sensing element positions 198 and/or pressure sensing element positions 200 may be grouped in regions of pad 202. Additionally or alternatively, the spacing between adjacent capacitive sensing element positions 198 and/or pressure sensing element positions 200 may be different in different regions of pad 202. Additionally or alternatively, one of capacitive sensing element positions 198 and pressure sensing element positions 200 may overlap with the other. Any other suitable arrangement or pattern of sensing element positions may be used.

The positioning of the sensing elements may be selected based on the type of substrate being used. For example, capacitive sensing element positions 198 may be positioned to ensure that the areas of pad 202 that are most likely to be affected by wetness events have at least one capacitive sensing element, or in some cases, a group of capacitive sensing elements. Pressure sensing element positions 200 may be positioned to ensure that the areas of pad 202 that are most likely to be affected by movements of wearer 14 have at least one pressure sensing element, or in some cases, a group of pressure sensing elements.

Acceleration Sensing

According to another aspect of the present disclosure, one or more accelerometers (not shown) may be part of system 10. An accelerometer may be positioned, for example, at or near any of the capacitive sensing element positions 198 and/or pressure sensing element positions 200, or at or in any of receiver 22, processor 24, and transmitter 26. In one example, the accelerometer may be secured within any suitable pocket on substrate 18. Additionally or alternatively, the accelerometer may be on or within base 190.

The accelerometer may be used to reduce interference. For example, the accelerometer can be used to detect if the resident is lying down or upright. Each of these states may have an impact on readings from other sensing elements 20. For example if a wearer urinates while lying down, the distribution of urine in absorbent article 16 may be different than the distribution when the wearer urinates while standing and/or sitting. Moreover, the chance of a leakage occurring is greater. These factors may have an impact on readings from sensing elements 20. Accelerometer readings can be used to reduce interference due to those factors.

The accelerometer data may be used to mitigate the effects of interference on capacitive sensing elements. The accelerometer data may be used in a manner similar to the way that the pressure sensing element data may be used. For example, the process of multiple linear regression utilized for the pressure and capacitive sensing elements, may also be utilized on the accelerometer, using the accelerometers x, y and z accelerations as inputs.

Additionally or alternatively, the accelerometer data may be used to determine a wearer's position, and the aforementioned pressure sensing element algorithm can be refined based on the determined position. For example regression may be run on data from: a wearer lying down to develop an interference reduction algorithm for a lying down mode, the wearer sitting to develop an interference reduction algorithm for a sitting mode, and/or the wearer standing to develop an interference reduction algorithm for a standing mode. The mode can then be detected using the accelerometer, so that the appropriate interference reduction algorithm is applied.

A wearer's position/orientation can be detected by comparing relative values of acceleration among the x, y, and z-axes, as produced by the accelerometer while the accelerometer data is constant and sums to a vector roughly equivalent to gravitational acceleration g. Constant accelerometer data may imply that the wearer is likely not accelerating (or is accelerating at a constant rate, which is unlikely to occur for a long period of time). The vector produced may be indicative of the direction of gravitational pull with respect to the accelerometer. The orientation of the portion of device 17 to which the accelerometer is mounted, with respect to gravity (which can be assumed to act downwardly), may be the negative of the vector. The orientation of the portion of device 17 with respect to the wearer may be relatively constant (since, for example, the portion may rest on absorbent article 16 applied on wearer 14), and thus, from this the wearer's orientation (position of the wearer in an upright, sitting, or lying position) may be determined. The mode, and corresponding interference reduction algorithm, may be selected based on such data.

Additionally or alternatively, interference reduction may be achieved in other ways. For example, temperature sensing elements for sensing body heat may be used to detect the presence, proximity, and/or movement of the wearer's body; one or more capacitive sensing elements may be replaced by a group of capacitive sensing elements positioned relative to each other such that they can distinguish between capacitive changes caused by the wearer's body or a wetness event; multiple layers of capacitive sensing elements, separated by spacers, may be used to distinguish between the wearer's body movement and a wetness event; optical sensing elements may be used to detect wearer movement, and capacitive sensing element readings/values may be adjusted to mitigate the effect of the movement; an eddy-current sensing element may be employed to monitor and/or reduce interference produced by proximity and/or contact of the wearer relative to one or more portions of absorbent article 16; and/or a Hall sensing element may be used to monitor and/or reduce interference from nearby magnetic or conductive bodies. Any of these additional sensing elements may be positioned, for example, at or near the sensing element positions shown in FIG. 4. Alternatively, one or more of the additional sensing elements may be positioned on the exterior surface of absorbent article 16, on the interior surface of absorbent article 16, and/or within absorbent article 16 between the interior and exterior surfaces thereof.

Interference Shielding

According to another aspect of the present disclosure, interference is reduced by shielding sensing elements 20 from outside influence. One or more techniques may be employed to shield sensing elements 20. One exemplary technique includes providing one or more spacers between sensing elements 20 and the exterior surface of substrate 18. Another technique includes arranging one or more layers to shield electrical signals and/or voltages associated with sensing elements 20. The spacers and/or layers reduce interference from conductors outside of absorbent article 16.

FIG. 24 shows an exemplary schematic of capacitive sensing element 119 being used to sense capacitance(s) of wearer 14 and/or absorbent article 16. Capacitive sensing element 119 includes one or more capacitor plates 203. Capacitive sensing element 119 are coupled to one or more device ground plates 204 of a device ground 206. FIGS. 25-28 show exemplary schematics similar to that of FIG. 23, but with one or more layers for shielding. For example, in the shielded arrangement of FIG. 25, a signal plate 208 of a shielding layer 210 is configured to carry any suitable shielding signal. A signal may be suitable for shielding if it results in a capacitance between capacitor plate 203 and signal plate 208 not being impacted by motion of objects external to absorbent article 16, or being impacted by a small enough of a degree that the effect on readings from capacitive sensing element 119 are negligible. One shielding signal includes the signal used to measure capacitance, e.g., the signal provided by signal generator 124 (FIGS. 11 and 13). The signal used to measure capacitance is a useful shielding signal because the capacitance between capacitor plate 203 and signal plate 208 is very small, since the voltage on both plates is similar. It is contemplated, however, that other shielding signals may be applied for reducing/mitigating the impacts of external objects. For example, a signal of similar shape to the signal generator signal, but with a different frequency, may be applied.

Figure 29:
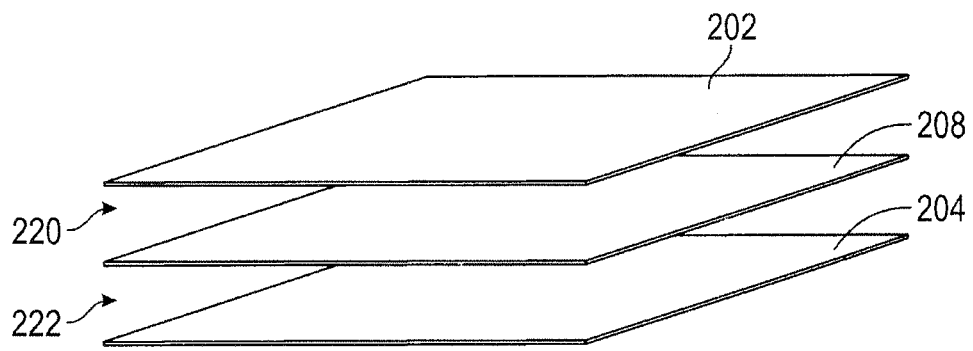
FIG. 29 is a perspective view of an arrangement of shielding plates, in accordance with aspects of the present disclosure.
Figure 30:
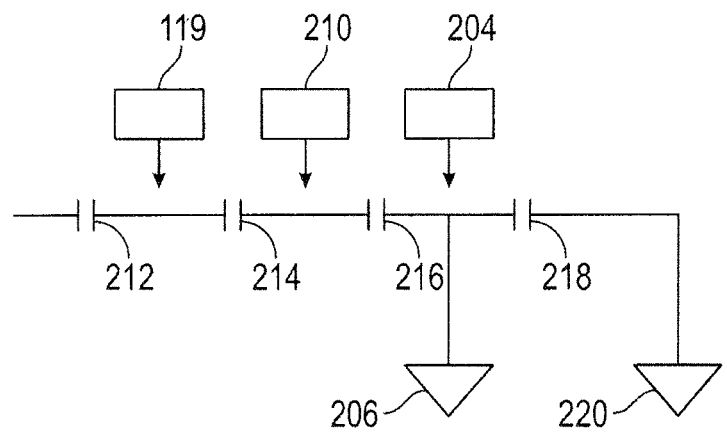
FIG. 30 is a circuit diagram, in accordance with aspects of the present disclosure.

FIG. 26 shows a schematic of a shielded arrangement similar to the one in FIG. 25, but with both signal plate 208 and ground plate 204. FIG. 30 shows an exemplary circuit diagram representing one implementation of the schematic of FIG. 26. A series of capacitances 212, 214, 216, 218 are monitored as a result of the arrangement. Capacitance 212 is indicative of the capacitance between absorbent article 16 and capacitive sensing element 119. Capacitance 214 is the capacitance between capacitive sensing element 119 and shielding layer 210. The signal in shielding layer 210 is chosen so that the value of capacitance 214 fluctuates minimally in the presence of external conductors. One exemplary signal is the one from signal generator 124. Capacitance 216 is the capacitance between shielding layer 210 and device ground 206. Capacitance 218 is the capacitance between the device ground 206 and an external conductor (external ground 220). FIG. 29 shows one example of how plates may be arranged in the shielded arrangement of FIG. 26, with capacitive plate 203, signal plate 208, and ground plate 204 separated by gaps 220, 222 filled by spacers (not shown).

Figure 28:
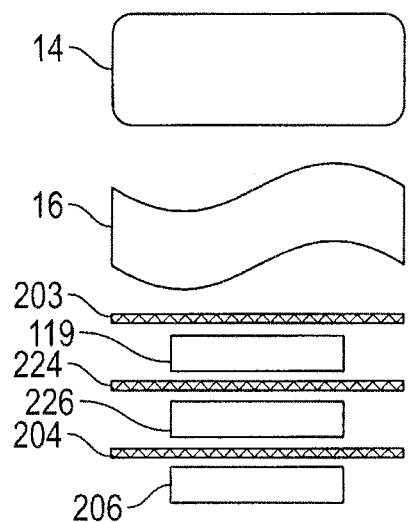

FIGS. 27 and 28 show schematics of other shielded arrangements that are similar to the arrangement of FIG. 26. The arrangement in FIG. 27, however, includes two signal plates 208a, 208b of two shielding layers 210a, 210b, and two ground plates 204a, 204b of two device grounds 206a, 206b. The arrangement of FIG. 28 includes a voltage plate 224 of a voltage layer 226 in place of a signal plate of a signal layer. The addition of multiple or redundant signals and ground plates improves the shield effect that may mitigate or cancel out exterior influences, such as the movement of the wearer's legs.

Wire Interference

Another source of interference may be wire interference associated with wires in device 17 (FIG. 1). Examples of wires include wires 192, 196 (FIGS. 22A-22C). Wires 192, 196 run the length of base 190, and in at least one example, wires 192, 196 may extend further beyond an end of base 190 for connecting with at least one of receiver 22, processor 24, and transmitter 26 (FIG. 1). Device 17 may also include one or more wires connected to the above-described shielding layers and grounds. There is the potential for interference to be produced between the wires 192 and these other wires.

Figure 31A:
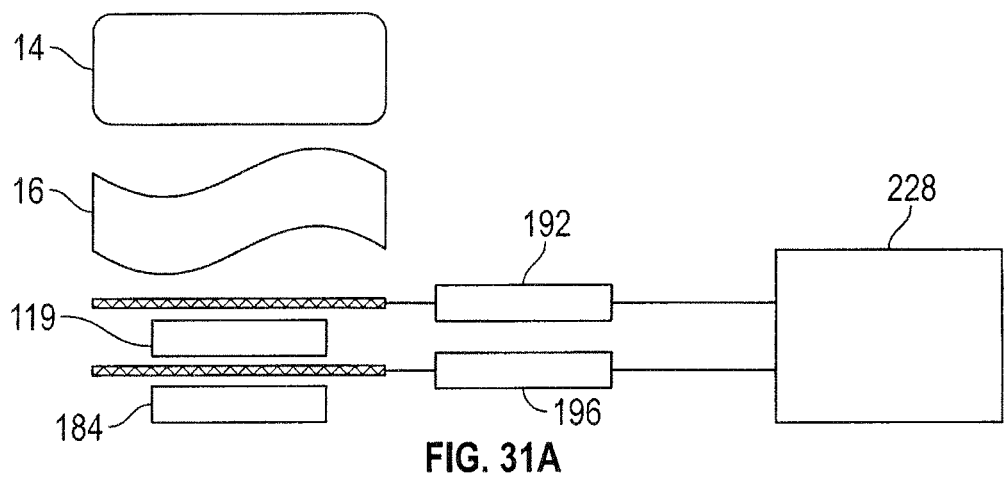
FIGS. 31A and 31B show schematics for capacitive sensing, in accordance with aspects of the present disclosure.
Figure 31B:
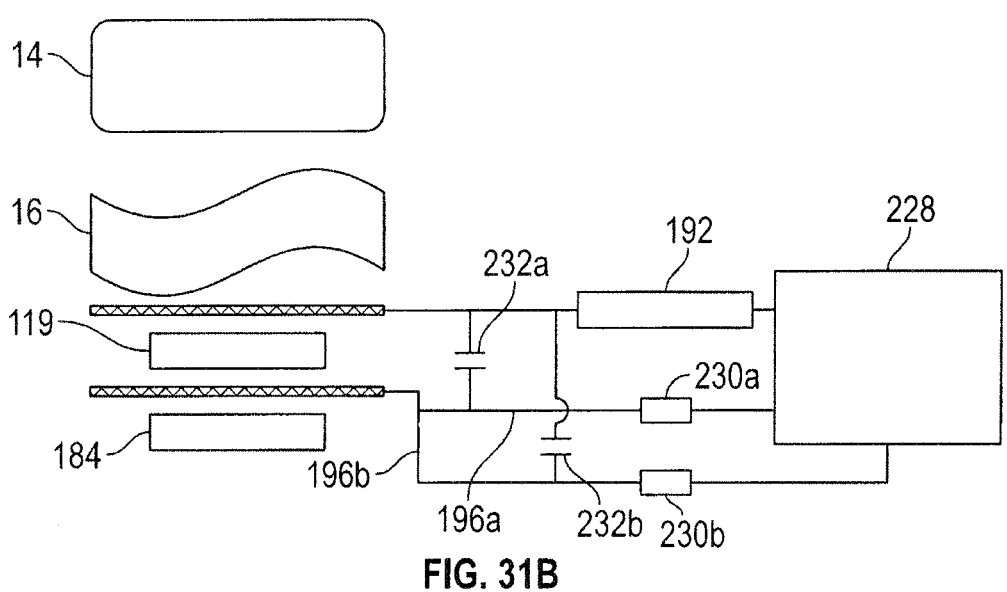

One scenario where wire interference may present an issue is when capacitive sensing element 119 is used in conjunction with pressure sensing element 184, as shown in the schematic of FIG. 31A. Wires 192, 196 connect capacitor 119 and pressure sensing element 184 to other components 228 of device 17. As shown in more detail in FIG. 31B, pressure sensing element 184 includes a variable resistor (not shown), and further includes two wires 196a, 196b, each with a different voltage 230a, 230b. The interference caused by coupling and/or capacitance between wires 192, 196a, 196b, represented by capacitances 232a, 232b, may be mitigated by maintaining a constant distance between the wires. It should be understood that generally, the wires of many types of sensing elements may cause interference, and any voltage or signal therein may have an impact on capacitive sensing element 119.

According to one aspect, one or more shielding plates/layers (not shown) may be incorporated into system 10 to mitigate interference on wires 192, caused by wires 196a, 196b and/or wires of other sensing elements. The shielding plates/layers may be similar to those shown in FIGS. 25-30. It is contemplated that the orientation and/or form of the shielding plates/layers may be modified to reduce wire interference. For example, the shielding plates/layers may be constructed to lie in between wire 192 and wires 196a, 196b.

This may reduce the impact of noise on capacitive sensing element 119 due to wires 196a, 196b. When shielding plates/layers are used, there is the potential for interference to be produced by relative movement between two or more of the shielding plates/layers; the wires 192, 196a, 196b; and any of the other plates (e.g., capacitive plates and ground plates). If any of the distances between these components changes due to the relative movement, the measured capacitances may be affected. To mitigate this type of interference, any shielding plates/layers, wires, and/or other plates may be maintained at relatively constant distances from capacitive sensing element 119 and wire 192.

Figure 32:
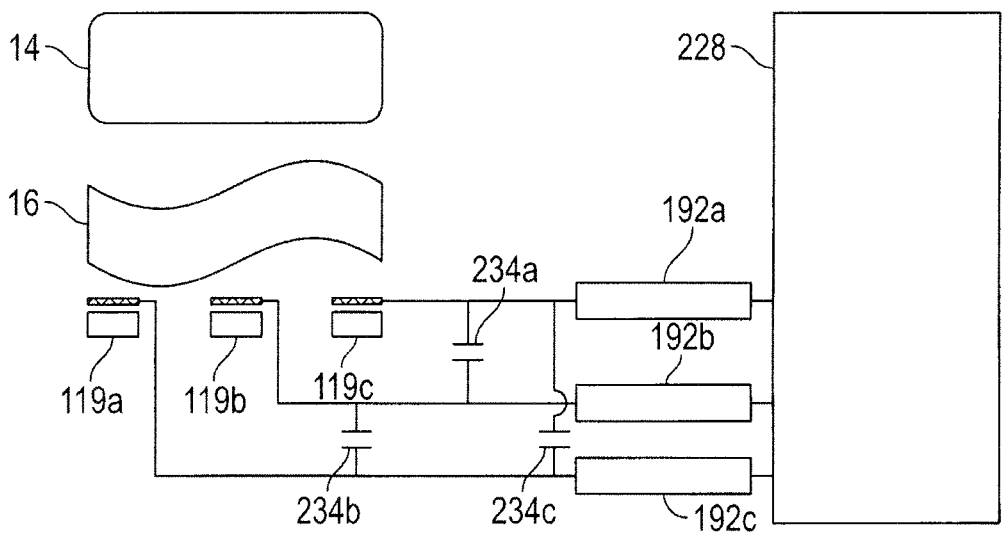
FIG. 32 is a circuit diagram with multiple capacitive sensing elements, in accordance with aspects of the present disclosure.

FIG. 32 shows an exemplary circuit in which multiple capacitive sensing elements 119a, 119b, 119c are used. Capacitive sensing elements 119a, 119b, 119c are connected to other electronic components 228 of device 17 by wires 192a, 192b, 192c that may be in the vicinity of each other. Due to this proximity, there is a potential for capacitive sensing elements 119a, 119b, 119c to interfere with each other. This interference is represented by interference capacitances 234a, 234b, 234c. Interference capacitances 234a, 234b, 234c may be mitigated by maintaining a relatively constant distance between wires 192a, 192b, 192c. This may produce a relatively constant capacitance between capacitive sensing elements 119a, 119b, 119c that may be easily identified and accounted for. Wires 192a, 192b, 192c may be kept at a constant distance by using any suitable connection mechanism that holds wires 192a, 192b, 192c in position. Additionally or alternatively, wires 192a, 192b, 192c may be joined together in fixed positions in the form of, for example, a parallel cable.

Additionally or alternatively, an algorithm may be applied to reduce the interference caused by capacitive sensing elements on other capacitive sensing elements. This algorithm may include, for each capacitive sensing element, reducing a sensing element value of the capacitive sensing element by a value that is a function of all of the other capacitive sensing elements. An example of a function may be a linear combination, such as:

modified value for capacitive sensing element$_1$=actual value for capacitive sensing element$_1$−sum($m_i$*capacitive sensing element$_j$) for each $i$ not equal to 1

In this function, m may be indicative of the slopes associated with each capacitive sensing element and its relative impact on capacitive sensing element1. This process may be repeated for each capacitive sensing element. The slopes m, can be determined by performing the following experiment: (a) collecting a dataset whereby the target sensing element (capacitive sensing element$_1$) is not touched or influenced directly (without interference the value for capacitive sensing element$_1$ would be 0) and where all of the other capacitive sensing elements are excited/activated; and (b) running a multiple regression on the dataset with Y equalling capacitive sensing element1's values and Xs equalling the other capacitive sensing elements' values.

Additionally or alternatively, a more generalized function may be applied, and neural networks may be used to determine the function. In that scenario, the neural network may be trained with capacitive sensing element$_1$ as the target and the other capacitive sensing element values as the inputs. This process may be repeated for each capacitive sensing element.

Conductive Sensing

In addition to capacitive sensing elements 119, or as an alternative to them, sensing elements 20 may include one or more conductive sensing elements. Conductive sensing elements may be applied to an interior surface of absorbent article 16, such that the conductive sensing elements may be directly exposed to exudate. Conductive sensing elements may be disposed after a single use. One type of conductive sensing element includes conductive fabric. Another type of conductive sensing element includes conductive ink. Both types will be described in more detail below. It should be understood, however, that any other suitable type of conductive sensing element may also be used. Also it should be understood that aspects of system 10 described above in connection with the use of capacitive sensing elements 119 may be applicable to the use of conductive sensing elements, and vice-versa. For example, the same type of receiver 22, processor 24, and/or transmitter 26 may be used with both kinds of sensing elements. Pressure sensing elements and/or an accelerometer may be used in combination with both kinds of sensing elements to provide additional data about wetness events, since characteristics of wetness events may be affected by the movements and/or positioning of wearer 14 when the wetness event occurs. Additionally or alternatively, capacitive sensing elements 119 may be used in combination with conductive sensing elements, wherein the combined data from both kinds of sensing elements may provide caregiver 12 with a more accurate understanding of characteristics of wetness events.

It is also contemplated that one or more of the above-described elements and steps used for reducing interference for capacitive sensing elements may be used to reduce interference with respect to conductive sensing elements. For example, reductions in interference may be achieved by using one or more pressure sensing elements in conjunction with one or more conductive sensing elements, using an accelerometer in conjunction with one or more conductive sensing elements, shielding one or more conductive sensing elements (and/or their wires) with interference shielding, and/or using shielding layers in the one or more conductive sensing elements (and/or their wires).

Figure 33A:
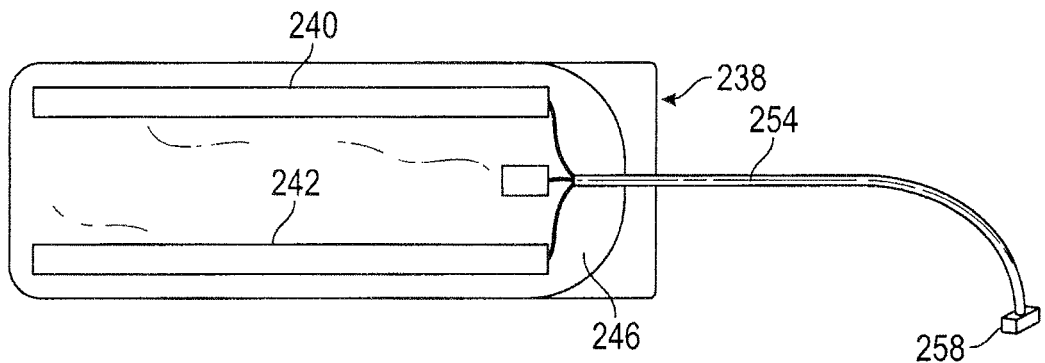
FIGS. 33A-33C are alternative views of a conductive sensing element, in accordance with aspects of the present disclosure.
Figure 33B:
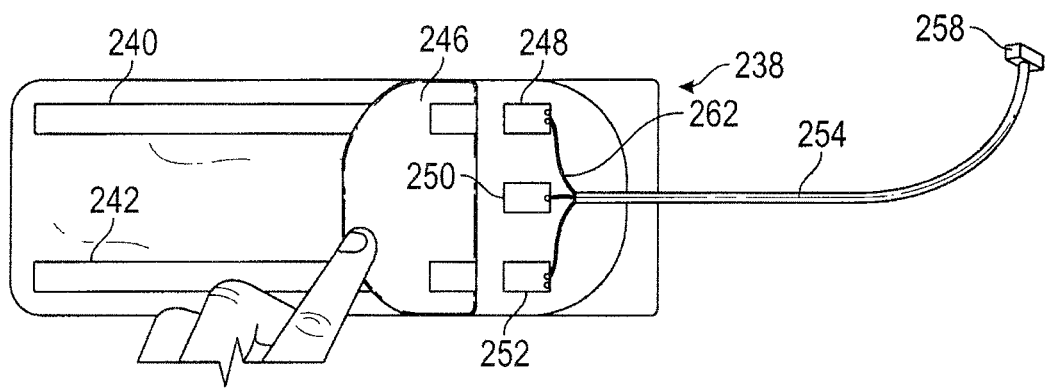
Figure 33C:
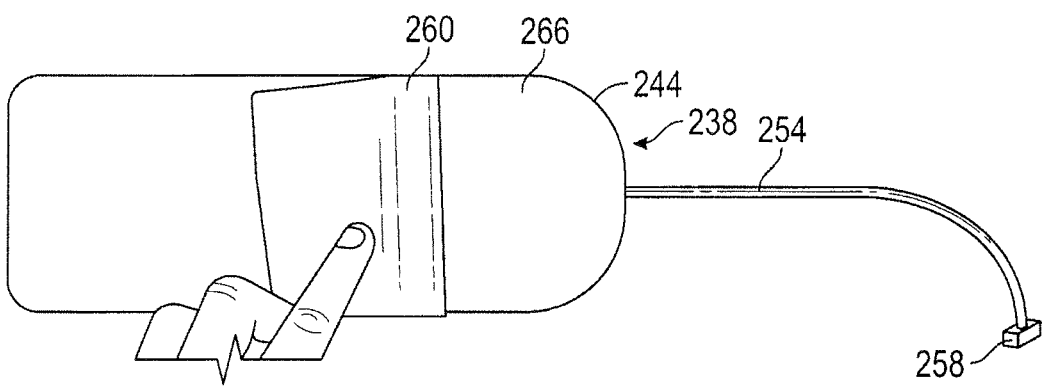

FIGS. 33A-33C show aspects of an exemplary conductive fabric sensing element 238. Conductive fabric sensing element 238 includes, for example, two strips of conductive fabric 240, 242 that are placed parallel to each other. In one example, conductive fabric 240, 242 are spaced approximately two inches apart from each other. Conductive fabric 240, 242 may include a metal-impregnated ripstop fabric, and/or may be made from a combination of synthetic polyester and metallic powder (e.g., silver powder). Conductive fabric 240, 242 are secured between and/or to a layer of super absorbent material 244 and a layer of porous fabric 246. Conductive fabric 240, 242 are connected at one end of conductive fabric sensing element 238 by leads 248, 250, 252. Leads 248, 250, 252 are coupled to a connector 254. Connector 254 includes, for example, one or more wires 256 having a fixed end coupled to leads 248, 250, 252. A free end of connector 254 includes a plug 258 that may be received in a port (not shown) of receiver 22, processor 24, and/or transmitter 26 (FIG. 1). Conductive fabric 240, 242, super absorbent material 244, porous fabric 246, leads 248, 250, 252, connector 254, and plug 258 provide a disposable assembly that, when in use, may be applied lengthwise to the interior surface of absorbent article 16 via adhesive or any other suitable fastening element. Where adhesive is used, a removable sheet 260 is used to cover the adhesive until conductive fabric sensing element 238 is ready to be applied to absorbent article 16, at which time sheet 260 may be peeled off to expose the adhesive. In use, conductive fabric sensing element 238 detects wetness events by detecting changes in resistance across strips of conductive fabric 240, 242.

FIG. 33A shows a top view of conductive fabric based sensing element 238. FIG. 33B shows the top view, but with super absorbent material 244 pulled back to expose leads 248, 250, 252 and the fixed end of connector 254. Conductive fabric 240, 242 may be secured to, or embedded in, porous fabric 246. Leads 248, 250, 252 may include strips of conductive tape. The conductive tape may be made of copper, or any other suitable conductive material. The conductive tape may form a connection between connector 254 and conductive fabric 240, 242. The conductive tape may be secured to a first side of super absorbent material 244. Each of the lengths of the conductive tape, in its middle section, may have two wires 262, 264 connected thereon. Wires 262, 264 may form a closed loop between two pins in connector 254 and/or on plug 258, which may allow receiver 22, processor 24, and/or transmitter 26 to detect when conductive fabric sensing element 238 is plugged in. Detecting when sensing element 238 is plugged in may allow system 10 to identify when absorbent article 16 has been changed.

An adhesive or other fastening element 266 may be provided on a second side of super absorbent material 244, the second side being opposite the first side, and the second side facing the interior surface of absorbent article 16. Adhesive 266 may be covered by sheet 260. FIG. 33C shows one end of sheet 260 pulled back to expose a portion of the second side of super absorbent material 244 and adhesive 266.

From a top down view, that is, moving from the surface of sensing element 238 that will be closest to wearer 14 toward the surface that will be closest to the interior surface of absorbent article 16, the sensing element 238 includes three layers: porous fabric 246, strips of conductive fabric 240, 242, and super absorbent material 244. Moisture from exudate may pass through porous fabric 246. Porous fabric 246 may help insulate the wearer's skin from moisture that has passed through porous fabric 246. Porous fabric 246 may also prevent direct contact between the wearer's skin and conductive fabric 240, 242, which may create noise in values/readings taken with sensing element 238. Super absorbent material 244 enables wetness to be detected at the interior surface of absorbent article 16. Absorbent article 16, like sensing element 238, may also include a top layer of porous material followed by a lower layer of superabsorbent material. Placing an additional layer of superabsorbent material 244 on top of the absorbent article's porous material allows some wetness to be retained in the vicinity of sensing element 238 before the wetness is absorbed through the porous material of absorbent article 16 and cannot be readily accessed or detected.

Top views of individual layers that form an exemplary sensing element are 238 shown in FIGS. 34A-34E. Layer 268 (FIG. 34A) may be composed of absorbent paper. Layer 270 may be composed of a flex cable that may be pre-assembled and pre-cut, for inclusion in the assembly process of the conductive fabric sensing element. The flex cable may include an off the shelf parallel cable with a 6-pin connector. Layer 272 may be composed of two strips 274, 276 of ripstop conductive fabric. Layer 278 may be composed of absorbent paper. Layer 280 may be composed of a porous non-woven fabric. The non-woven fabric may be made of plastic, rubber, or a combination of plastic and rubber. Other suitable materials are also contemplated. One or more of these layers may be cut from one or more sheets.

Assembly of the conductive fabric sensing element may include coupling the above-described layers. For example, an adhesive (not shown) may be applied to a portion of a bottom surface of layer 270, and layer 270 may be adhered to a top surface of layer 268. In one example, a left side portion of layer 270 may be adhered to a right side portion of layer 260. Then adhesive may applied to layer 272, and layer 272 may be adhered to layers 268, 270. It is contemplated that the adhesive may be applied to a bottom surface of layer 272, so that layer 272 may be adhered to top surfaces of layers 268, 270. Strips 274, 276 of layer 272 may extend along lateral edges of layer 268. Then adhesive may be applied to layer 278, and layer 278 may be adhered to a top surface of layer 270. For example, the adhesive may be applied to a bottom surface of layer 278, and layer 278 may be adhered to the left side portion of layer 270. Then layer 280 may be placed on top of the other layers, and may be melted to the other layers in one or more locations along its edges. The material for layer 280 may have a melting temperature less than 150 degrees Celsius. Layers 268 and 280 may closely overlap each other, such that the contours of layer 268 may follow the contours of layer 280. After the layers have been assembled, an adhesive (not shown) may be applied to a bottom surface of layer 268, and a plastic sheet or film (not shown) may be placed over the adhesive for protection. The plastic film may be able to be peeled off, to expose the adhesive, so that the conductive fabric sensing element can be adhered to the inside surface of absorbent article 16.

Figure 35A:
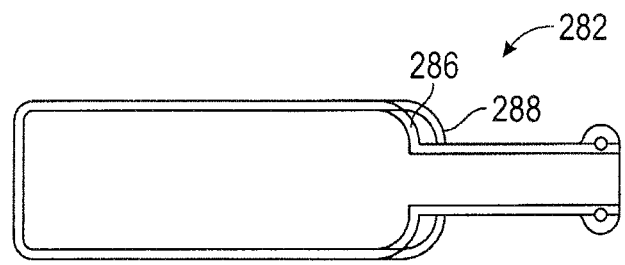
FIGS. 35A-35D are top views of layers of a conductive sensing element, in accordance with aspects of the present disclosure.
Figure 35B:
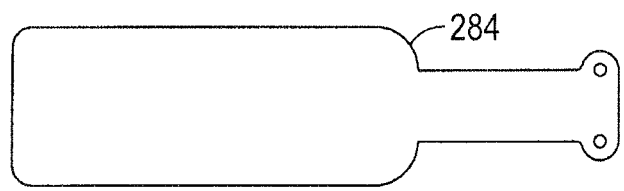
Figure 35C:
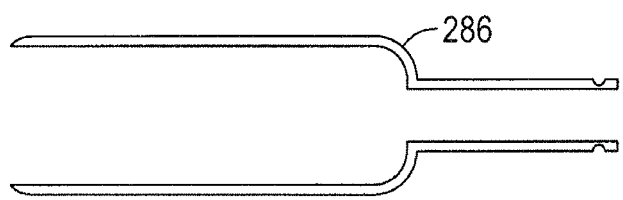
Figure 35D:
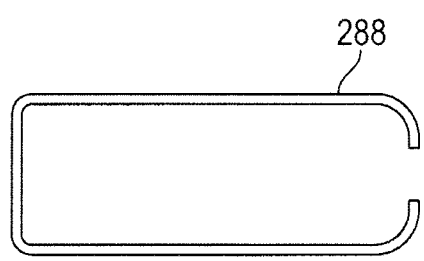

FIG. 35A shows a top view of a conductive ink based sensing element 282. FIGS. 35B-35D show top views of the individual layers that may be combined to form sensing element 282. Instead of having layer 270 (e.g., a flex cable) and layer 272 (e.g., ripstop conductive fabric) described above, sensing element 282 includes one or more layers with a conductive ink applied thereon. For example, instead of having layer 270 and/or layer 272, sensing element 282 has a layer 284 (non-woven fabric) and a layer 286 (conductive ink lines). Receiver 22, processor 24, and/or transmitter 26 may connect to layer 284, and may make contact with layer 286. The three layers of sensing element 282 are described in more detail below.

Layer 284 may be composed of a non-woven fabric. The non-woven fabric may be similar to the material found in diapers or on the inside of feminine pads. The non-woven fabric may be paper-like in texture and pliability. Layer 284 may be cut into shape using a rotary die cutter or similar technique.

Layer 286 may be composed of a conductive ink or paint. The conductive ink may include water and powdered silver. The conductive ink may be applied to a top surface of layer 284 using a rotary screen printer or a similar technique. Heat sealing may be performed, depending on the material selected. The edges of layer 286 may follow the contours of layer 284. Additionally or alternatively, multiple strips and/or patterns of conductive ink may be used to increase the amount of information gathered regarding the moisture in absorbent article 16. Potential patterns include multiple strips arranged horizontally and/or vertically, which may enable the detection of local and small urination events; and an array of dots or other shapes, such that the conductance between every two dots/shapes may be measured to build a more accurate moisture profile.

Layer 288 may be composed of a non-conductive adhesive. The adhesive may be applied to a bottom surface of layer 284, and a thin sheet of protective plastic (not shown) may be added on top of the adhesive. This may enable users to peel off the plastic to reveal the adhesive, so that conductive ink sensing element 282 can be applied to the interior surface of absorbent article 16. A technique similar to rotary screen printing may be used to apply the adhesive.

Impedance Sensing

As an alternative to a system that exclusively uses capacitive sensing, sensing elements 20 may include one or more complex impedance sensing elements for detecting and/or monitoring both the resistive and capacitive components of absorbent article 16 and/or wearer 14. Impedance (e.g., complex impedance) may be described as a complex ratio of voltage to current in an alternating current (AC) circuit. Impedance may be viewed as extending the concept of resistance to AC circuits. Impedance may possess both a magnitude and a phase, and/or may be expressed as both a real and imaginary component. The real component may represent a resistive component of the impedance, and the imaginary component may represent a reactive or capacitive component of the impedance.

Impedance measurement has many applications in medical devices. For example, bioimpedance measurements may be used to image lung volume, detect respiration, and body composition. Aspects of impedance sensing elements and/or impedance sensing techniques that may be used in addition to, or alternatively to, capacitive sensing elements/techniques and/or conductivity sensing elements/techniques, are described in greater detail below.

Figure 36A:
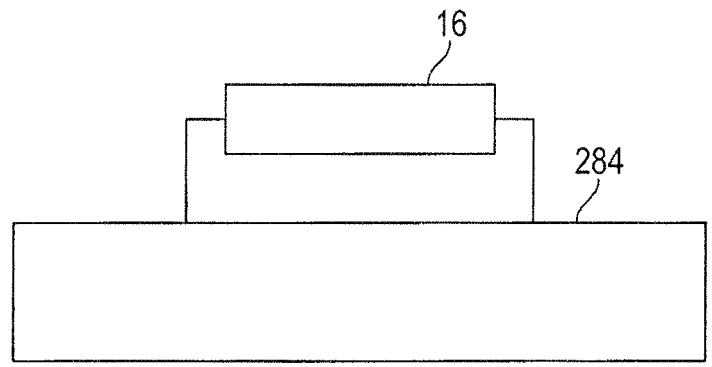
FIG. 36A is a general overview of impedance measurement sensing, in accordance with aspects of the present disclosure.
Figure 36B:
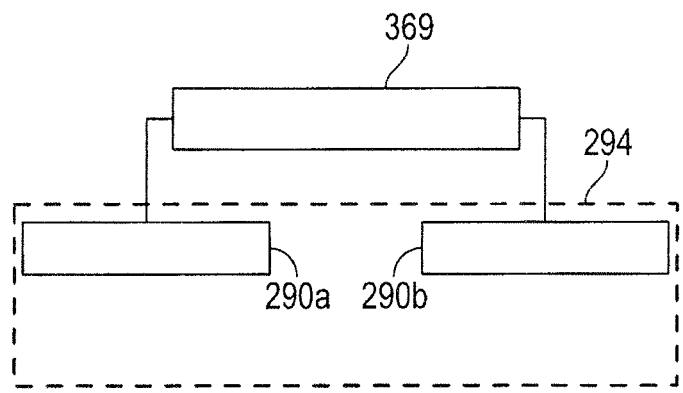
FIG. 36B is an exemplary configuration of an impedance measurement sensing element, in accordance with aspects of the present disclosure.

An exemplary impedance measurement sensing element may include, for example, two conductive plates, configured to measure the impedance of an article, such as absorbent article 16, and/or a wearer 14. FIG. 36A depicts a general overview of an impedance measurement sensing element 284 configured for measuring the impedance of absorbent article 16 and/or wearer 14, and/or capacitance between sensing electrodes. FIG. 36B depicts one exemplary configuration of sensing element 284, where sensing element 284 includes two conductive plates or electrodes 290a, 290b for measuring an impedance 369 of absorbent article 16. Sensing element 284 may include more than two, such as, for example, four, six, or any other number of conductive plates/electrodes.

Figure 38:
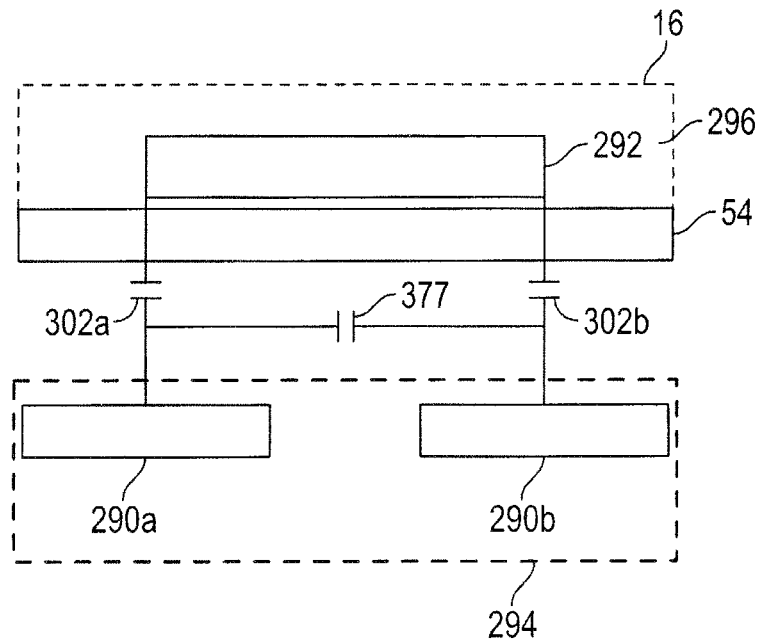
FIG. 38 is a schematic circuit diagram showing impedance sensing by capacitively coupling electrodes, in accordance with aspects of the present disclosure.

An impedance 292 of an interior region of absorbent article 16 is measured and/or determined by capacitively coupling electrodes 290a, 290b, at a region exterior to absorbent article 16, to the interior region of absorbent article 16. FIG. 38 shows one such arrangement. Electrodes 290a, 290b, which include impedance sensing members, may be located in the proximity of absorbent article 16, but in an exterior region 294. For example, electrodes 290a, 290b may be positioned near, at, or on an exterior surface of absorbent article 16. Electrodes 290a, 290b are used to measure impedance 369 of absorbent article 16, and a capacitance 377 between electrodes 290a, 290b. Those measurements are used to determine impedance 292 of an interior region 296 of absorbent article 16, without making galvanic contact with moisture in absorbent article 16. Capacitive coupling of electrodes 290a, 290b to absorbent article 16 through one or more nonconductive layers of absorbent article 16 (e.g., through water-resistant outer layer 54) is represented by capacitors 302a, 302b.

Receiver 22, processor 24, transmitter 26, and/or server 30 may form part of an impedance measuring subsystem of system 10. These parts of system 10 may run software modules to perform the steps described below. Sensing elements 20, for sensing impedance, may include electrodes 290a, 290b that may be secured to an exterior surface of absorbent article 16, and positioned so as to be capacitively coupled to interior region 296 of absorbent article 16. Electrodes 290a, 290b may be used to measure impedance of absorbent article 16. The impedance measuring subsystem may measure the impedance between, for example, electrodes 290a, 290b, and may extract a real component of the impedance and an imaginary component of the impedance using any suitable models, algorithms, and/or devices. Based on the extracted components, the impedance measurement subsystem may determine characteristics of the moisture in absorbent article 16. The characteristic may include, for example, a presence, amount, and/or location of the moisture in absorbent article 16. Additionally or alternatively, the characteristic may include a degree of wetness of the absorbent article, in terms of level of saturation, capacity left for additional moisture, and the like.

Impedance measuring subsystem may measure the complex impedance between electrodes 290a, 290b. The complex impedance may have a magnitude and a phase. The magnitude and/or the phase may be indicative of characteristics of the moisture. For example, a reduction in the phase and the magnitude may be indicative of a state where absorbent article 16 is wet but not filled to capacity. Absorbent article 16 may be filled to capacity when its ability to absorb additional moisture falls below a predetermined level (established, for example, by a manufacturer, facility where wearer 14 resides, or best practices followed by caregivers 12); when it physically cannot absorb additional moisture; and/or when it cannot absorb additional moisture without leaking. A reduction in the magnitude but not the phase may be indicative of a state where absorbent article 16 may be filled to capacity.

The complex impedance may have a resistive component and a reactive component. The impedance measurement subsystem may be configured to perform an optimization technique using a linear regression, a neural network, and/or a support vector machine, to determine a relationship between the resistive and reactive components of the impedance and the characteristics of the moisture. Additionally or alternatively, the impedance measurement subsystem may be configured to perform a simulation to determine a relationship between the resistive and reactive components of the impedance and the characteristic of the moisture. Additionally or alternatively, the impedance measurement subsystem may be configured to acquire data from another system that is distinct from system 10, to determine a relationship between the resistive and reactive components of the impedance and the characteristic of the moisture. The systems may be distinct in that one is not configured to directly communicate with the other. It is also contemplated that the impedance measurement subsystem may be configured to determine whether device 17, and/or individual impedance sensing elements 20, are attached to absorbent article 16 based on characteristics of the reactive component. For example, if a characteristic of the reactive component falls outside of a predetermined range, it may indicative that device 17, and/or one or more of sensing elements 20, is not attached.

The impedance measurement subsystem may measure the impedance by applying a voltage to one of electrodes 290a, 290b and measuring current at the other of the electrodes 290a, 290b. Additionally or alternatively, the impedance measurement subsystem may be configured to measure the impedance by applying a current to one of electrodes 290a, 290b and measuring a voltage between that electrode and the other electrode. It is also contemplated that the impedance measurement subsystem may determine characteristics of the moisture in absorbent article 16 using the real component of the impedance.

According to one aspect, impedance 292 of interior region 296 of absorbent article 16 is assumed to be entirely resistive, as shown in FIG. 62. A resistance 378 can be determined by taking only the real component of the measured impedance 369 of absorbent article 16. This technique is valuable because it is capable of measuring resistance 378 of interior region 296 of absorbent article 16 even if capacitances 302*a*, 302*b* between electrodes 290*a*, 290*b* and interior region 296 change. Capacitances 302*a*, 302*b* may be expected to change as a result of electrodes 290*a*, 290*b* being slightly displaced from, for example, the underside of the exterior of absorbent article 16, deformed, and/or repositioned.

This technique has been verified by empirical data, as shown in graphs 297 and 299 of FIG. 61, which displays that as volume increases, the impedance decreases monotonically. However, as volume increases, phase can be seen to first increase and start decreasing again after a certain amount of moisture has been added. Impedance 292 of interior region 296 of absorbent article 16 may be modeled as a resistor 378, and the entire system may be modeled as capacitors 302*a*, 302*b* in series with resistor 378, and in parallel with capacitance 377 between electrodes 290*a*, 290*b*, as shown in FIG. 62. When interior region 296 of absorbent article 16 is dry, the resistance of resistor 378 may be very large (>10 megaohms, as an example), and the system may reduce to a single capacitor 377. The result may be that the impedance may be very high, and the phase may be very close to 90 degrees, as shown in FIG. 61. As moisture is added, resistance 378 of impedance 292 of interior region 296 of absorbent article 16 may decrease (going, for example, to a value between 100 kiloohms and 5 megaohms), creating a resistive pathway, and decreasing the phase shift. As large volumes of moisture are added, the resistance 378 may be reduced drastically and may approach a closed circuit when compared to the impedance of capacitors 302*a*, 302*b*. For example, resistance 378 of impedance 292 may decrease to less than 25 kiloohms. Resistance 378 may be so low that it may be counted as a closed circuit. In this scenario, the system may be purely capacitive and driven by capacitances 302*a*, 302*b* from the outside of absorbent article 16 to interior region 296 of absorbent article 16. The phase may return to −90 degrees, as indicated by FIG. 61, because it can be approximated as purely capacitive.

It is also contemplated that sensing element 284 may be positioned on or in absorbent article 16 in the same way as the capacitive sensing elements, pressure sensing elements, and conductive sensing elements described in the paragraphs above. It is also contemplated that sensing element 284 may be connected to receiver 22, processor 24, and/or transmitter 26 in the same way as the capacitive sensing elements, pressure sensing elements, and conductive sensing elements. Processor 24 may estimate the impedance of absorbent article 16 and/or wearer 14 using any suitable method. For example, processor 24, and/or a local or remote controller or microprocessor, may make suitable measurements to determine an impedance value or characteristic 369 of absorbent article 16 and/or wearer 14 and/or impedance value 292 of the interior of absorbent article 16, and consequently evaluate moisture characteristics inside absorbent article 16, as described in greater detail below.

According to one aspect, impedance measurement of impedance 369 of absorbent article 16 and/or wearer 14 may be conducted by applying or injecting an alternating current to one of conductive plates 290*a*, 290*b*, and withdrawing and measuring the voltage between conductive plates 290*a*, 290*b*. The impedance can then be calculated by extracting the real component of the impedance and imaginary component of the impedance from the measured voltage signal.

According to one aspect, impedance measurement of impedance 369 of absorbent article 16 and/or wearer 14 may be conducted by delivering alternating voltage to one of conductive plates 290*a*, 290*b* and measuring the current at the other conductive plate 290*a*, 290*b*. The impedance can then be calculated by extracting the real component of the impedance and imaginary components of the impedance from the measured current signal.

According to one aspect, the alternating voltage may be created by a digital to analog converter (not shown). The digital to analog converter may accept digital signals from a direct digital synthesis component. The frequency of the direct digital synthesis component signal may be specified by an external signal, or may be pre-set. By employing a direct digital synthesis, the alternating voltage frequency can be selected and modified via software.

According to one aspect, the current at the input electrode of conductive plates 290*a*, 290*b* may be measured by measuring the voltage drop across a resistor. The measured voltage may then be used to determine the real and imaginary components of the impedance.

According to one aspect, the real and imaginary components of the impedance may be determined by applying a Discrete Fourier Transform to digital conversion of measured or derived voltage from the input electrode of conductive plates 290*a*, 290*b*. The digital conversion of the measured or derived voltage may be obtained by applying the measured or derived voltage to an Analog to Digital Converter.

According to one aspect, the real and imaginary components of the impedance may be determined by employing a synchronous detector with in-phase and quadrature detection.

According to one aspect, a dedicated component or components may be used to determine the impedance of absorbent article 16 and/or wearer 14. Communication (e.g., wired or wireless) may be made with this component or this set of components to determine the impedance.

Figure 37:
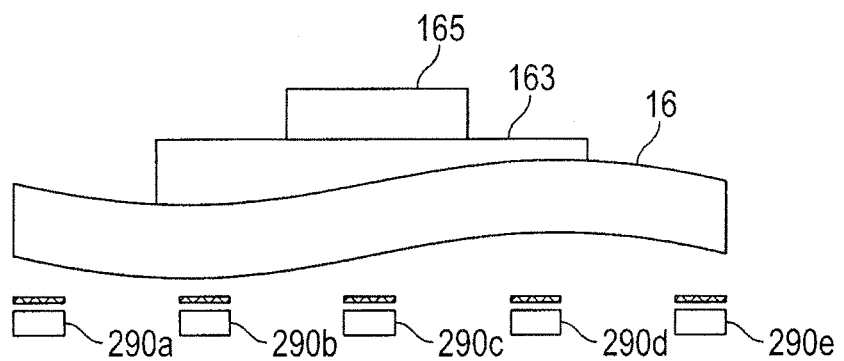
FIG. 37 is a diagram showing impedance sensing, in accordance with aspects of the present disclosure.

Changes in the impedance of absorbent article 16 and/or wearer 14 may be monitored to obtain an estimate of one or more characteristics of wetness events on or in the vicinity of absorbent article 16. According to one aspect, and as shown in FIG. 37, a plurality of electrodes 290*a*-290*e* may be monitored. For example, the impedance between any, some, or all pairs of electrodes 290*a*-290*e* can be measured and used to obtain an estimate of one or more characteristics of wetness events on or in the vicinity of absorbent article 16. The impedance between electrodes 290*a*-290*e* may be measured by applying an oscillating current to one electrode (source electrode), and then measuring the voltage between the source electrode and another electrode. An impedance map can be generated using the measured impedances. Using the impedance map, certain wetness characteristics can be extracted, including the volume of exudate in absorbent article 16, the distribution of exudate in absorbent article 16, and the likelihood of leakage of absorbent article 16.

Electrodes 290*a*-290*e* include, for example, conductive plates, electrocardiogram electrodes, conductive fabric strips, conductive rubber, embedded conductive materials (e.g., clips), conductive ink or paint, and/or conductive pouches. One or more of electrodes 290a-290e may be positioned at, on, or in the underside of absorbent article 16. For example, one or more of electrodes 290a-290e may be embedded in absorbent article 16 and/or secured to the interior surface of absorbent article 16. Alternatively, one or more of electrodes 290a-290e may be integrated with absorbent article 16. While five electrodes are shown, it should be understood that a different number of electrodes may be used. Moreover, the electrodes may be arranged in any suitable array to facilitate coverage of different regions of absorbent article 16.

Impedance measurements may be calibrated for improved detection/monitoring of wetness events. For example, impedance measurements may be calibrated based on one or more of the following: the size of absorbent article 16, the manufacturer of absorbent article 16, the age of wearer 14, the weight of wearer 14, the thickness of absorbent article 16, the distance between absorbent article 16 and one or more of the electrodes, and/or the sex of wearer 14. It is also contemplated that impedance measurements may be normalized based on inputs from other sensing elements, including sensing elements not configured to detect wetness events (e.g., a pressure sensing element or an accelerometer).

According to another aspect, an impedance sensing method may include feeding a multitude of frequencies to conductive plates or electrodes 290a-290e. Material response may change with frequency, and measuring the impedance on multiple frequencies may provide additional information that may be used when characterizing wetness events. The frequency generating and monitoring component may be, for example, a part of processor 24, and/or may be in the form of a microcontroller or other analog circuitry. The frequencies may be discrete frequencies. It is also contemplated that the impedance sensing method may measure the impedance with a sinusoid of a single frequency.

It is also contemplated that one or more of the above-described elements and steps used for reducing interference for capacitive sensing elements may be used to reduce interference with respect to the impedance sensing elements. For example, sources of interference may include motion and proximity of other human body parts such as the legs and/or arms. Reductions in interference may be achieved by using one or more pressure sensing elements in conjunction with one or more impedance sensing elements, using an accelerometer in conjunction with one or more impedance sensing elements, shielding one or more impedance sensing elements (and/or their wires) with interference shielding, and/or using shielding layers in the one or more impedance sensing elements (and/or their wires).

According to one aspect, device 17 may utilize both conductive sensing and impedance sensing to obtain conductivity measurements and impedance measurements, respectively. For example, one or more of electrodes 290a-290e (FIG. 37), used for measuring impedance, may also be used to measure conductivity. One or both of these sensing techniques may be used to obtain an estimate of one or more characteristics of wetness events on or in the vicinity of absorbent article 16 and/or the presence of wearer 14.

Figure 39:
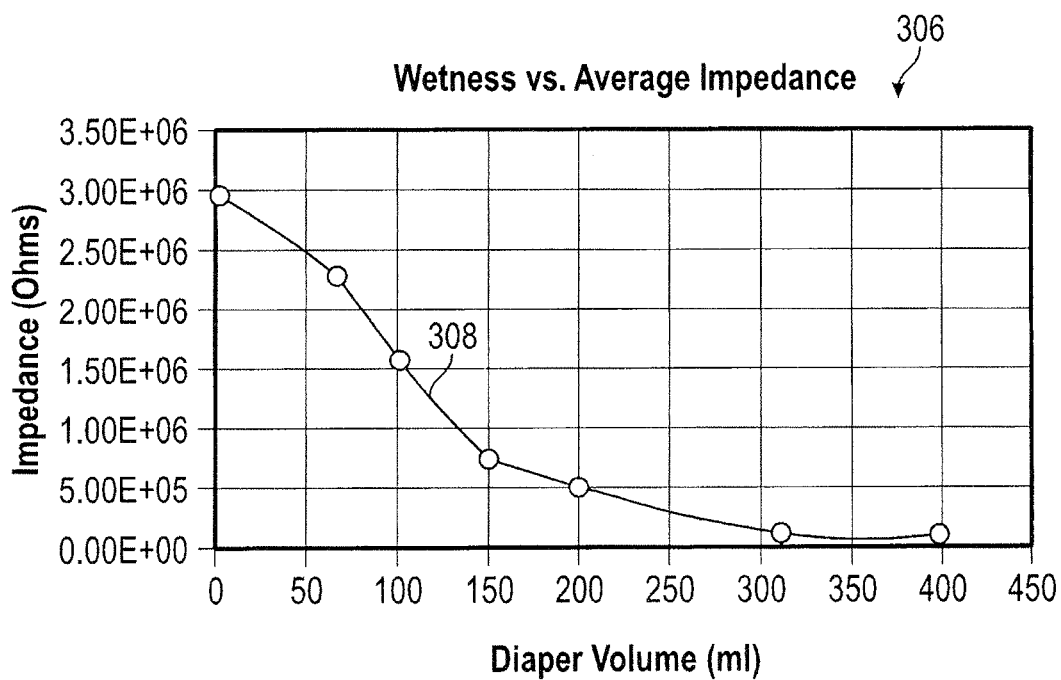
FIG. 39 is a graph showing a relationship between values of fluid volume versus impedance, in accordance with aspects of the present disclosure.

The saturation level of absorbent article 16, and/or the amount of liquid in absorbent article 16, may be estimated by observing changes in impedance 369 of absorbent article 16 and/or changes in the impedance of interior region 296 of absorbent article 16. As the amount of liquid inside absorbent article 16 increases, the measured impedance may decrease, and an algorithm may map the impedances to saturation levels and/or fluid volumes. Additionally or alternatively, as shown in FIG. 39, a graph 306 with impedance (e.g., average impedance) on the Y-axis, wetness (e.g., fluid volume) on the X-axis, and a curve 308 indicative of wetness versus impedance, may be generated.

Figure 40:
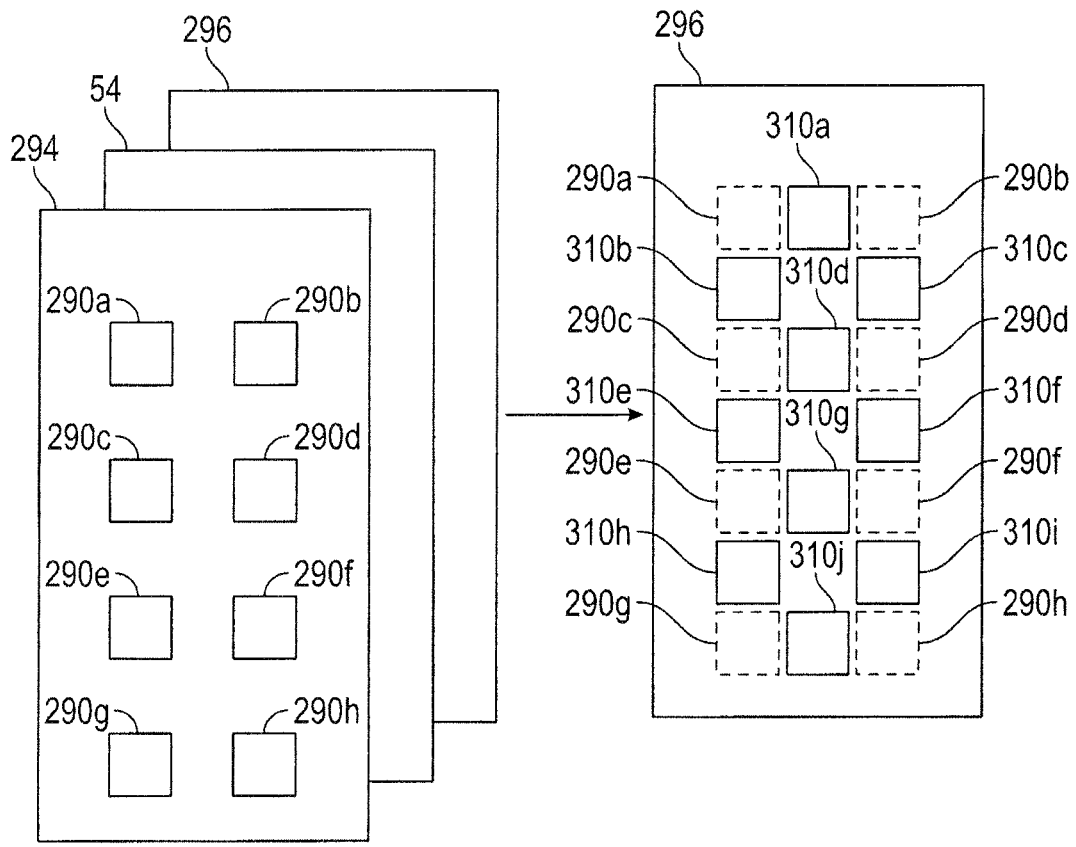
FIG. 40 is a schematic showing electrode placement and impedance measurement sites, in accordance with aspects of the present disclosure.
Figure 41:
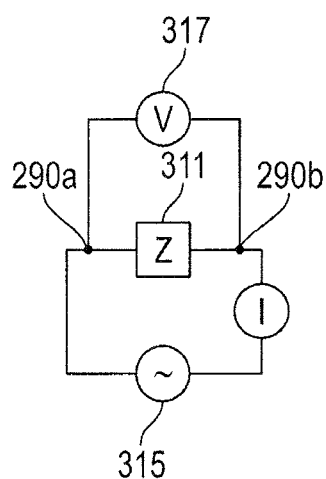
FIG. 41 is a circuit diagram for impedance sensing, in accordance with aspects of the present disclosure.

As shown in FIG. 40, electrodes 290a-290h are positioned at various locations in exterior region 294 near, at, or on the exterior of absorbent article 16. Impedances 310a-310j between adjacent electrodes may be determined to provide a map 316 of impedances and saturation levels at interior 296 of absorbent article 16. As shown in FIG. 41, an impedance 311 between a pair of electrodes or electrode wires 290a, 290b is measured by applying an oscillating current 315 to one electrode 290a (source electrode), and then measuring a voltage 317 between the source electrode 290a and the other electrode 290b. Map 316 of saturation levels is used to determine the saturation level of the entire absorbent article 16. The saturation level and saturation profile of absorbent article 16 is estimated by observing changes in impedances 310a-310j.

Figure 42:
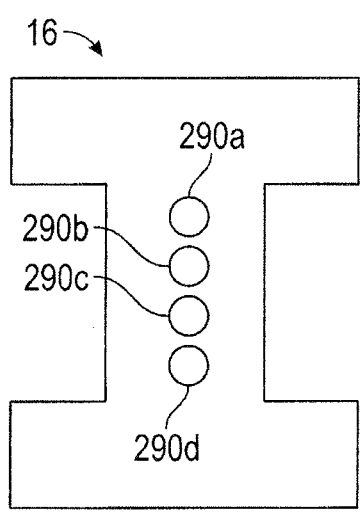
FIGS. 42-44 are top views of an absorbent article with electrode placement sites, in accordance with aspects of the present disclosure.
Figure 43:
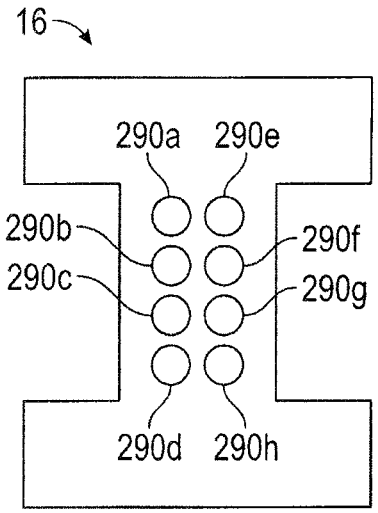

It should be understood that fewer or more electrodes and impedances may be used to generate a map, and/or electrodes may be positioned in different positions to form different patterns near, at, or on exterior 294 of absorbent article 16. For example, FIG. 42 shows a layout with electrodes 310a-310d arranged linearly along a length of absorbent article 16 (e.g., brief 32). FIG. 43 shows a layout with electrodes 290a-290h arranged linearly in four rows, two columns, along the length of absorbent article 16, in close proximity beside a centerline of absorbent article 16.

Figure 44:
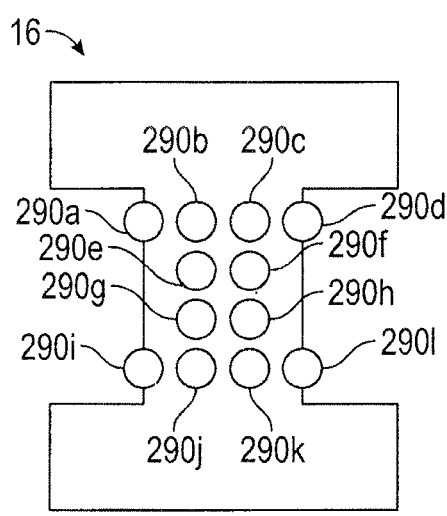

One circumstance that may arise in examples where wetness is sensed by measuring the impedance between pairs of electrodes is that certain regions of absorbent article 16 may not be covered by electrode pairs. As such, wetness may not be detected in those regions due to a lack of coverage. In order to minimize non-detection of wetness events, electrodes may be arranged to cover areas most prone to experiencing enuresis events. FIG. 44 shows an exemplary layout with electrodes 290a-290l arranged to cover areas that are most likely to experience enuresis events.

Figure 45:
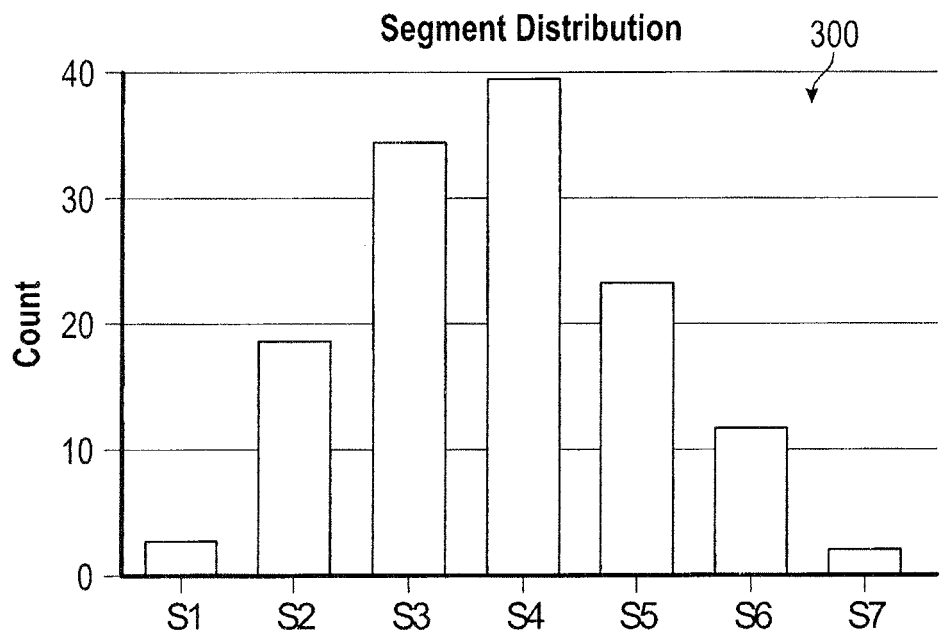
FIG. 45 is a bar chart indicative of distribution of the likelihood of enuresis events in several regions of an absorbent article, in accordance with aspects of the present disclosure.

FIG. 45 is a bar chart 300 showing a distribution of the likelihood of enuresis events being deposited in different regions or segments S1-S7 of absorbent article 16. Segments S1-S7 may be equally sized. To achieve 90% or higher enuresis event coverage, segments S2-S6 may be covered by electrodes. For example, if absorbent article 16 is 70 cm long, 90% or higher coverage may correspond with electrodes starting at 10 cm and covering absorbent article 16 up to 60 cm down the length of absorbent article 16.

Figure 58:
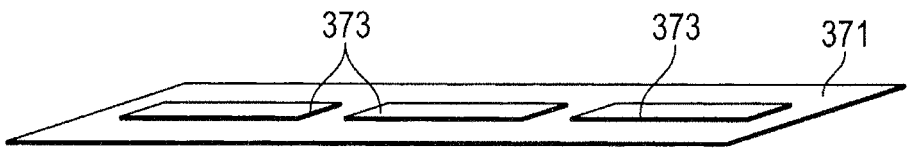
FIG. 58 is a perspective view of impedance sensing electrodes formed by conductive material deposited onto a flexible printed circuit board, in accordance with aspects of the present disclosure.

Impedance sensing electrodes, such as any of electrodes 290a-290e, may be formed by conductive material deposited onto a flexible printed circuit board (PCB), and capacitive coupling may be made via depositing of conductive material on the flexible PCB. One such example is illustrated by FIG. 58, which shows a flexible PCB 371 placed on the exterior of absorbent article 16 such that the electrodes and/or deposits of conductive material 373 are located in the vicinity of the exterior of absorbent article 16. For example, the electrodes and/or deposits of conductive material 373 may be adjacent to or against an underside of absorbent article 16. In one example, conductive material for the electrodes 373 are printed onto an exterior of device 17 to maintain a small gap between the electrodes 373 and absorbent article 16. In another example, the electrodes 373 are formed by a conductive adhesive applied to device 17. The conductive material that forms the electrode 373 may be in the form of a large area of conductor deposited onto device 17 and/or flex PCB 371. By depositing a conductor 373 that is co-planar to the exterior of absorbent article 16, the capacitance with the interior of absorbent article 16 may be increased, and therefore the sensitivity to detecting exudate inside absorbent article 16 may increase. Additionally, by reducing the distance between the conductor(s) that form(s) the electrode 373 and the exterior of absorbent article 16, the capacitance may be further increased.

Figure 60:
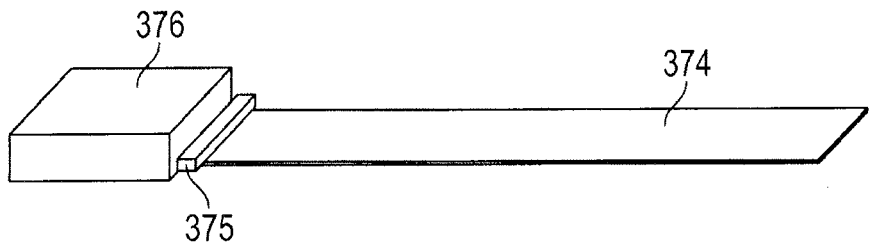
FIG. 60 shows a perspective view of an electrode and adhesion component connected to other components via a connector, in accordance with aspects of the present disclosure.

According to one aspect, and as shown in FIG. 60, a component 374 is indicative of the electrodes 373 and a solution to adhere and/or fasten the electrodes 373 to absorbent article 16. The electrode and adhesion component 374 are separate from a transmitter, battery, and/or processor component 376 via the presence of a connector 375. Due to anticipated wear on the adhesive solution, this arrangement may enable the adhesive solution to be swapped out for a new one without completely discarding the transmitter, battery, and/or processor component 376.

Figure 59A:
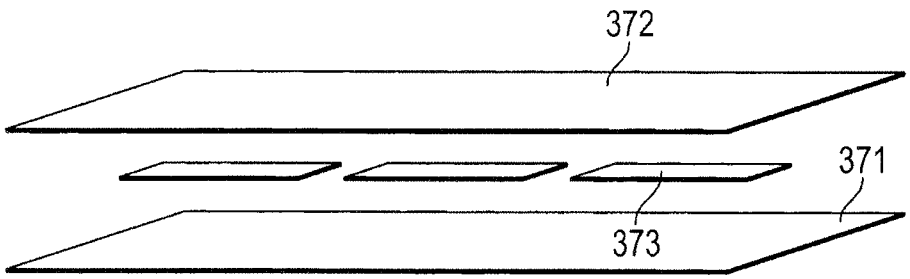
FIGS. 59A and 59B show perspective views of an adhesive and/or fastener material, electrodes, and a flexible printed circuit board, in accordance with aspects of the present disclosure.
Figure 59B:
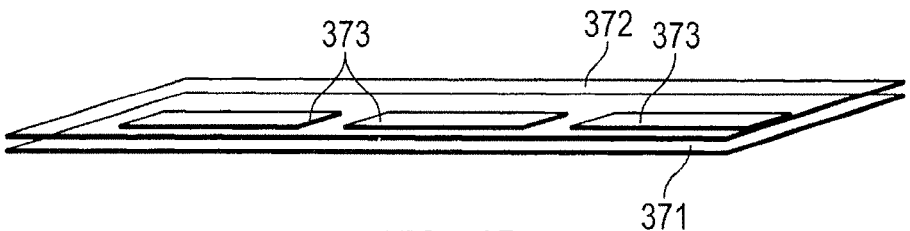

According to one aspect, the adhesive and/or fastener solution are in the form shown in FIGS. 59A and 59B. FIG. 59A displays an exploded view of the electrode 373 and an adhesion/fastening material 372. Adhesion/fastening material 372 goes on top of flex PCB 371. Adhesion/fastening material 372 that adheres the electrodes 373 may be in the form of one or more of adhesives, hooks to non-woven materials, and the like. Adhesion/fastening material 372 is deposited on top of flex PCB 371, as shown in FIG. 59B.

Figure 46:
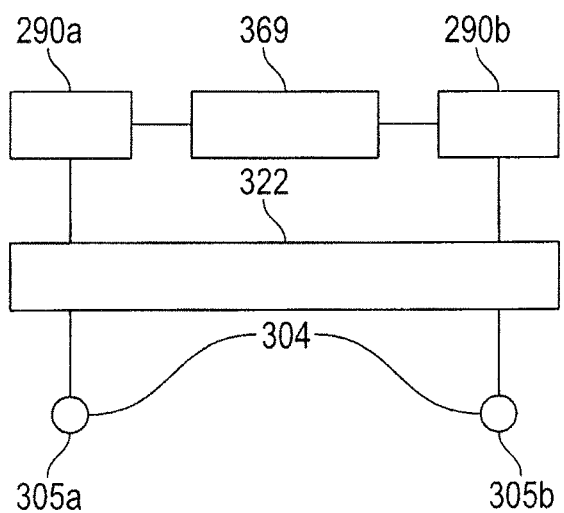
FIG. 46 is a circuit diagram showing the potential for interference when sensing impedance, in accordance with aspects of the present disclosure.

One circumstance that may arise with the use of an impedance measurement circuit that measures the impedance between electrodes is that the circuit may be subject to interference from other circuitry. As such, the circuit may actually be measuring not only the impedance of absorbent article 16, but also the impedance(s) of other circuitry including, for example, the impedance(s) of the PCB, electrode wires, a current generator, and/or other electrical components associated with measuring impedance. FIG. 46 shows a circuit diagram of such a circumstance, including a measured impedance 304 (between locations 305*a*, 305*b*), electrodes 290*a*, 290*b*, an absorbent article impedance 369, and impedance(s) of other circuitry 322. The additional impedance(s) 322 makes it difficult to accurately detect/monitor the impedance 369 of absorbent article 16, which in turn makes it difficult to determine impedance 292 of the interior of absorbent article 16. Additionally or alternatively, interference may be in the form of parasitic capacitance, series resistance, and shunt resistance.

Figure 47:
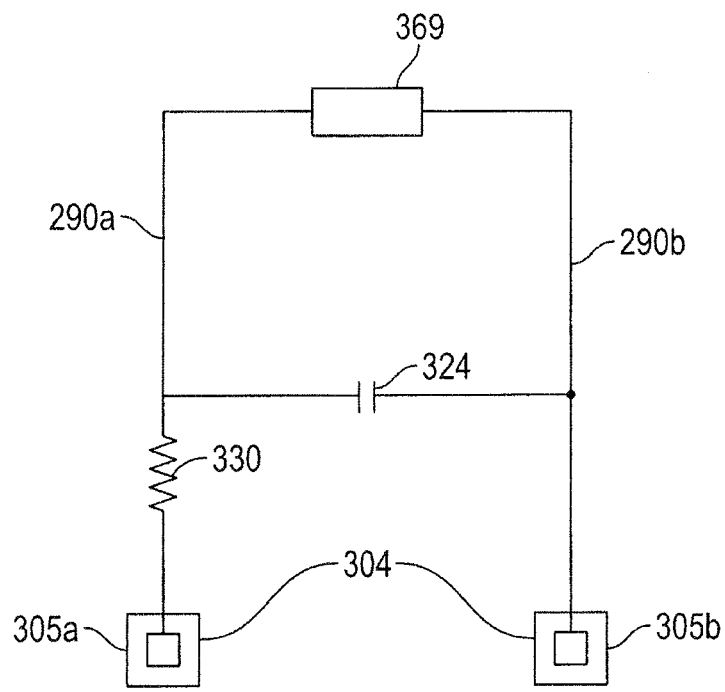
FIGS. 47-50 and 52 are impedance measurement models, in accordance with aspects of the present disclosure.

Impedance 369 of absorbent article 16 may be determined by applying a mathematical model to measured impedance 304 that may eliminate the impacts of impedance(s) of other circuitry 322. In one example, the impedance measurement model assumes that interference from other circuitry 322 may be of the form of a parasitic capacitance 324 between electrodes or electrode wires 290*a*, 290*b*, and a series resistor or resistance 330, as seen in FIG. 47. Static calibration factors may be used for parasitic capacitance 324 and series resistance 330 to determine absorbent article impedance 369 from measured impedance 304 between locations 305*a*, 305*b*. This model may receive, as inputs, measured impedance 304, the frequency of measured impedance 304, parasitic capacitance 324, and series resistance 330, to calculate absorbent article impedance 369 based, for example, on a formula derived from FIG. 47.

One circumstance that may arise is that parasitic capacitance 324 and/or one or more characteristics of series resistor 330 may change over time. This may be particularly prominent if other circuitry may be flexible enough to change shape with absorbent article 16. This may typically produce a high range of values for parasitic capacitance 324, causing errors in the calculation for absorbent article impedance 369. Accordingly, in one example, an impedance measurement model shown in FIG. 48 assumes that interference will take the same form referenced in FIG. 47, but the calibration factors (for parasitic capacitance 324 and series resistance 330) are determined dynamically (instead of statically) by measuring one or more known impedance(s) 340 located in the vicinity of electrode or electrode wire 290*a*. An impedance 304*a* between locations 305*a*, 305*c* is measured, and measured impedance 304 is compared to known impedance 340 to determine a series resistance 330*a* and a parasitic capacitance 324*a*. Then series resistance 330 and parasitic capacitance 324 is calculated by applying a fixed scaling factor to series resistance 330*a* and parasitic capacitance 324*a*. Next, measured impedance 304 is measured and the determined calibration factors is used as inputs to the impedance measurement model to calculate absorbent article impedance 369.

Figure 48:
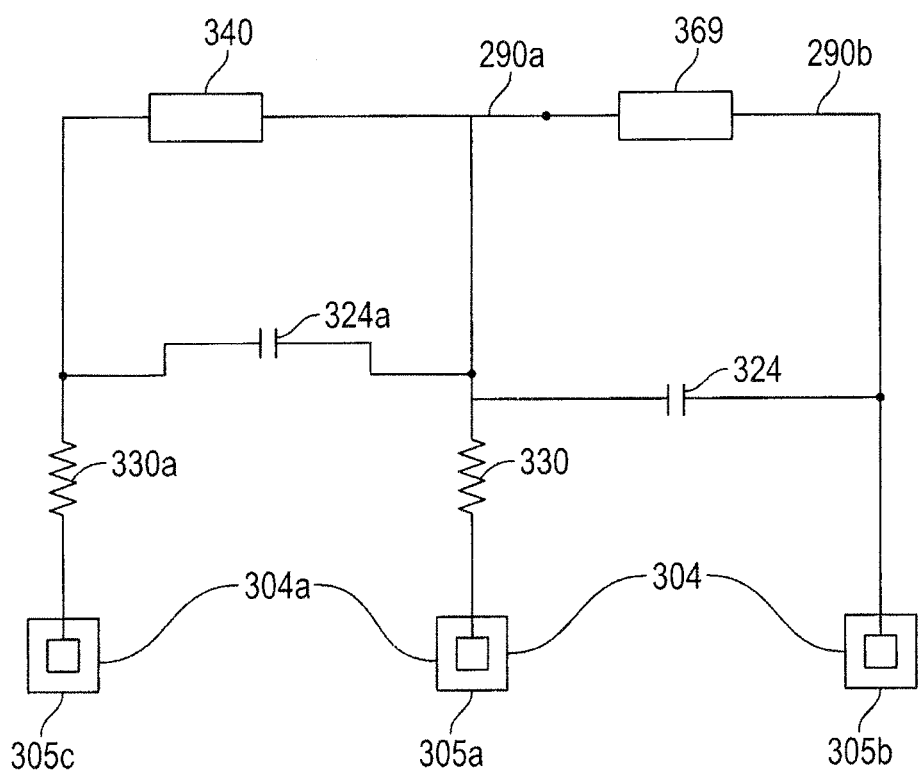
Figure 49:
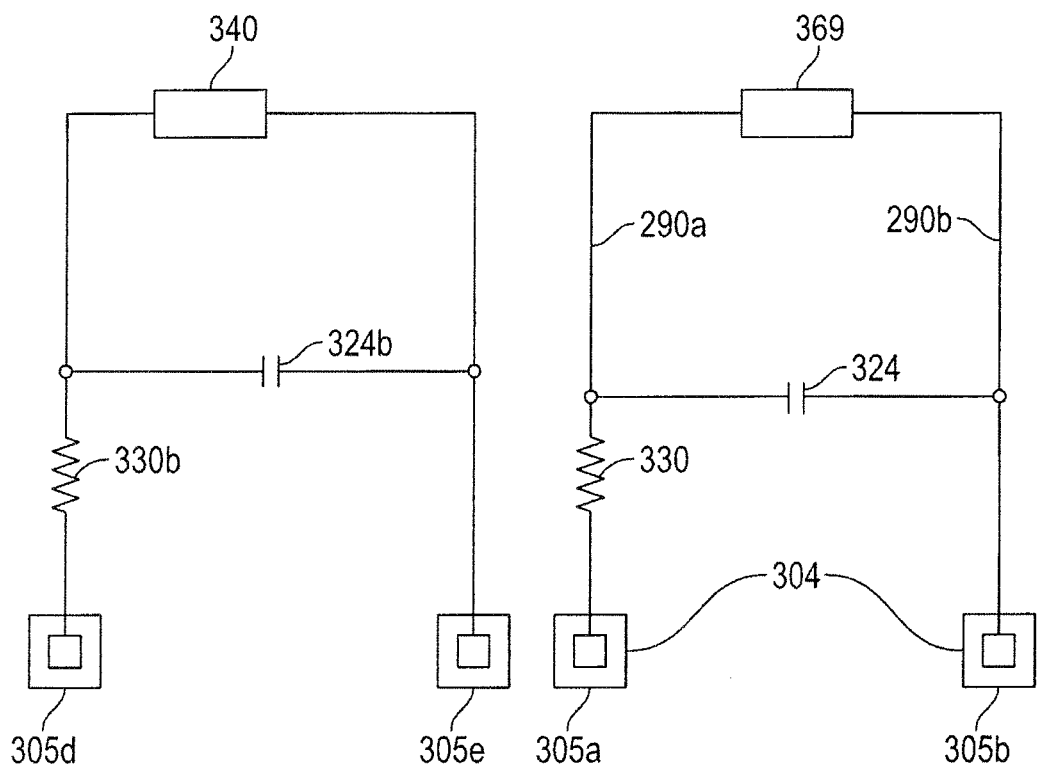

In another example, an impedance measurement model shown in FIG. 49 is similar to the model shown in FIG. 48 in its use of dynamic calibrations factors. In FIG. 49, calibration factors such as a parasitic capacitance 324*b* and series resistance 33*b* are determined by measuring known impedance 340 between locations 305*d*, 305*e*. The structure and positioning of known impedance 340 may be selected such that parasitic capacitance 324*b* and series resistance 330*b* are similar to parasitic capacitance 324 and series resistance 330 so that parasitic capacitance 324 and series resistance 330 can be calculated by applying a simple scaling factor or mapping from parasitic capacitance 324*b* and series resistance 330*b*. One such example is two parallel cables running in-line with the electrode wires that do not connect to electrodes and form an open circuit. The impedance between these two open circuit wires can be measured, and the parasitic capacitance between them can be determined. Once determined it can be assumed that the parasitic capacitance of wires with electrodes may be similar to the two wires without electrodes. By measuring the parasitic capacitance of open circuit wires, the parasitic capacitance estimate for wires with electrodes are able to reject minor deformations of absorbent article 16 and/or substrate 18, which are expected due to their flexible natures.

Figure 50:
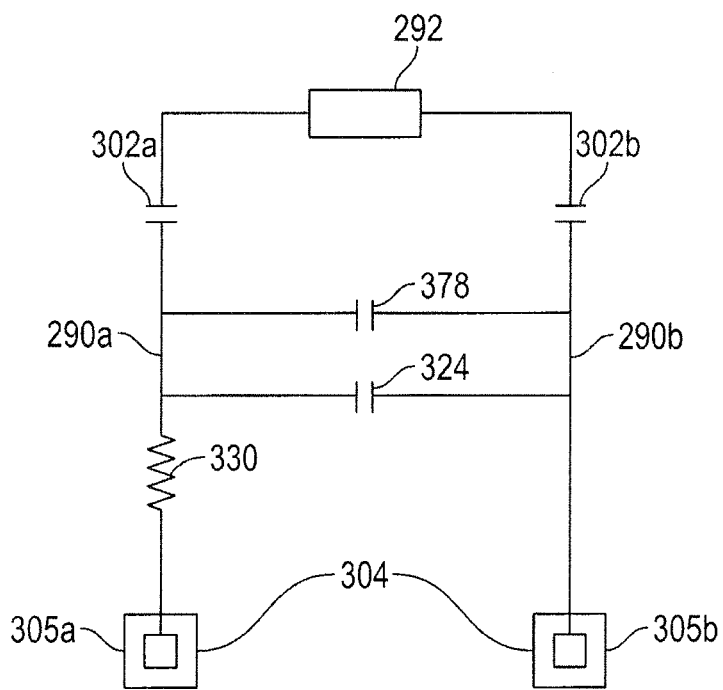

In some instances, where one or more electrodes are external to absorbent article 16, for example resting on or against the underside of absorbent article 16, the electrode may come slightly separated from the underside of absorbent article 16, causing absorbent article impedance 369 to increase because of decreases in capacitances 302*a* and/or 302*b*. Increases in absorbent article impedance 369 may cause absorbent article internal impedance 292 to be inaccurately measured. In view of this, it may be desirable to be able to measure absorbent article internal impedance 292, or a quantity pertaining to absorbent article internal impedance 292, that may be minimally impacted by such separation. In one example, impacts on measurements due to electrodes being slightly separated from the exterior of absorbent article 16 may be mitigated by modeling absorbent article impedance as a capacitor and resistor series. FIG. 50 shows an exemplary model of this type, where absorbent article capacitances 302*a*, 302*b* are coupled to absorbent article 16, for determining an impedance 292 of the interior of absorbent article 16. As electrodes separate from absorbent article 16, absorbent article capacitances 302*a*, 302*b* fluctuate. If it is assumed that the absorbent article interior impedance 292 is purely resistive, then the real component of absorbent article impedance 369 is equal to the resistance of the absorbent article interior impedance 292, and changes in capacitances 302a, 302b may not impact the measurement of absorbent article interior impedance 292 because capacitances 302a, 302b are purely imaginary impedances. This may be favorable because it allows the system to measure an internal resistance 378 of absorbent article 16, which decreases as moisture is applied, regardless of minor fluctuations in the position and proximity of electrodes 290a, 290b.

Once the impedance(s) between a pair or multiple pairs of electrodes have been measured, moisture in absorbent article 16 may be characterized using various algorithms to determine properties including, for example, saturation percentage, estimated fluid volume, and/or enuresis events. The algorithms receive the impedance value(s), calibration factors, and/or environmental factors, as inputs, and based thereon, calculate one of the aforementioned properties. In one example, saturation percentage and/or fluid volume is estimated by comparing each calculated impedance value to a threshold value. A score may be generated from the comparison, and may be incremented for each calculated impedance that is below the threshold value. Once the score has been determined, the saturation percentage and/or fluid volume can be estimated based on the score by using a scaling factor or lookup table. Additionally or alternatively, a determination that absorbent article 16 has exceeded a wetness threshold may be made by comparing the aforementioned score to a specified threshold that indicates to caregivers when the wetness threshold has been crossed. Wetness threshold scores may be tailored for use with certain absorbent articles 16, classes of absorbent articles 16, caregiver preferences, and/or wearer preferences.

In another example, the saturation percentage and/or fluid volume is estimated by comparing each calculated impedance value to multiple threshold values. Instead of generating a score by comparing the impedance values to a single threshold value, multiple thresholds may be used and the generated score may be calculated based on the results of the multiple comparisons.

In another example, the saturation percentage and/or fluid volume is estimated by calculating a score that is indicative of a sum of the outputs of functions of the calculated impedance values. Functions may include polynomials, sigmoid functions, and/or exponentials. The score may then be mapped to a saturation percentage and/or fluid volume using a lookup table. Equation 1 below describes how the score may be calculated where $Z_i$ is the calculated impedance and $f(Z_i)$ is the function.

$$\text{score} = \sum_{i=1}^{n} f(Z_i) \quad \text{(Equation 1)}$$

According to one aspect, the score is the generalized norm of the impedance values. Where exponent, n, ranges from 0 to infinity. The generalized norm offers flexibility in that n can be set such that n=0 to count impedances, n=1 to average impedances, and n=infinity to take the maximum impedance.

Figure 51:
FIG. 51 is a system block diagram outlining aspects for calibrating a system for use with a new brand and/or type of absorbent article, in accordance with aspects of the present disclosure.

One circumstance that may arise in exemplary arrangements that employ multiple impedance measurements across the exterior of absorbent article 16 to determine saturation percentage and/or fluid volume is that different regions of absorbent article 16 may be capable of containing different volumes of fluid. In such arrangements, it may be useful to differentiate between various areas of absorbent article 16. According to one aspect, scores are calculated in one or more of the ways described above, and different weighting is applied to the scores for different electrode pairs, in accordance with Equation 2 below. In the equation, the ith electrode pair may be weighted by factor $a_i$. Weightings may be selected so that in the event that different regions of absorbent article 16 contain different volumes of liquid, the score may more closely correlate with the particular volume.

$$\text{score} = \sum_{i=1}^{n} a f(Z_i) \quad \text{(Equation 2)}$$

Where device 17 includes multiple electrode pairs, wearer positioning (lying on back, side, front, sitting, or standing) may impact the amount of moisture in different regions of absorbent article 16. According to one aspect, an orientation sensing element (e.g., a gyroscope and/or accelerometer) is used to determine wearer orientation by determining the direction of the gravity vector and rotating the frame of reference to determine wearer orientation. Once wearer orientation is known, sections of absorbent article 16 may be dynamically weighted to increase/decrease their contribution to volume and/or saturation estimation based on the orientation.

Where electrodes are exterior to absorbent article 16, and can be used on different types of absorbent articles 16, properties of different brands/types of absorbent articles 16 may influence results. As such, calibration factors may be applied to different brands/types of absorbent articles 16. The calibration factors may be determined by mapping between algorithm scores and saturation level, notification threshold, and/or measured impedances of absorbent articles 16. Additionally or alternatively, specific calibration factors may be determined by measuring values of absorbent article 16 with a series of known moisture conditions applied, and then selecting the calibration factors that produce the most accurate results. FIG. 51 shows a flow diagram of how calibration and an algorithm modification process may be performed. The calibration system may acquire impedance data from benchtop testing on a new absorbent article type and/or brand with known moisture conditions applied to the absorbent article. The measurements from the calibration system may be used by the algorithm and calibration system to determine relevant calibration and/or algorithm factors for the new absorbent article. Once calibration and/or algorithm factors have been determined and verified they may then be passed on to the wetness detection system which is the system ultimately used in production. Each of the calibration system, algorithm system, and wetness detection system may share or have exclusive components. For example the calibration system and algorithm system may share a processor but the wetness detection system may have its own processor that implements the algorithm devised by the algorithm system. In one example, absorbent article specific weighting parameters are calculated by applying known moisture conditions to specific electrode pair regions. The pairwise weighting factors used in Eqn. 2 can then be determined by selecting the pairwise weighting factor that process the most accurate volume and/or saturation percentage estimates across the testing period.

Figure 52:
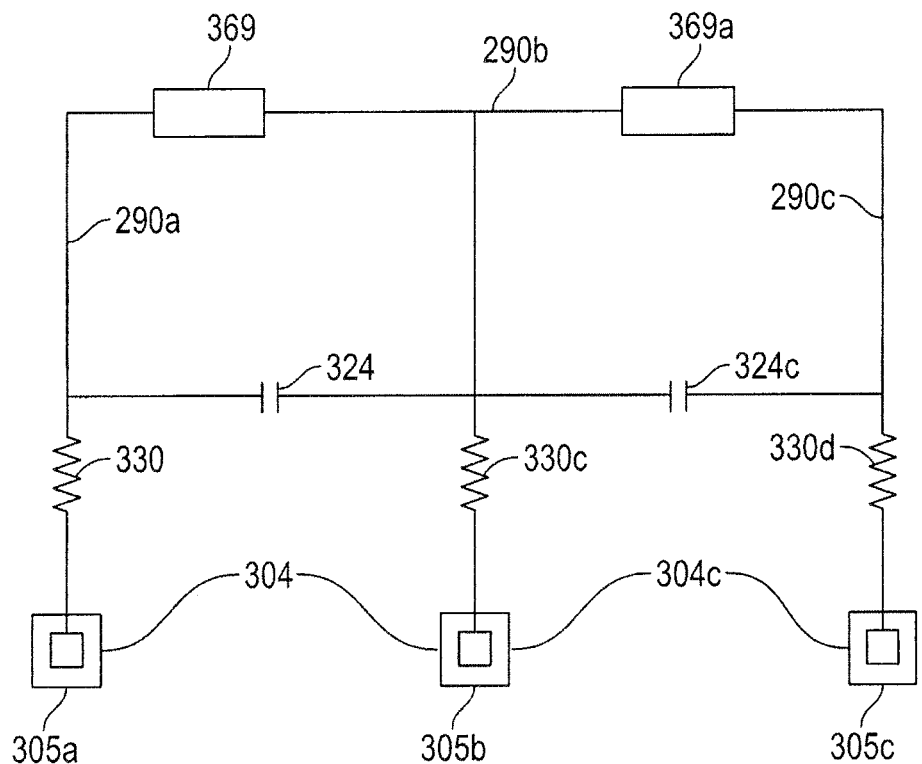
Figure 53A:
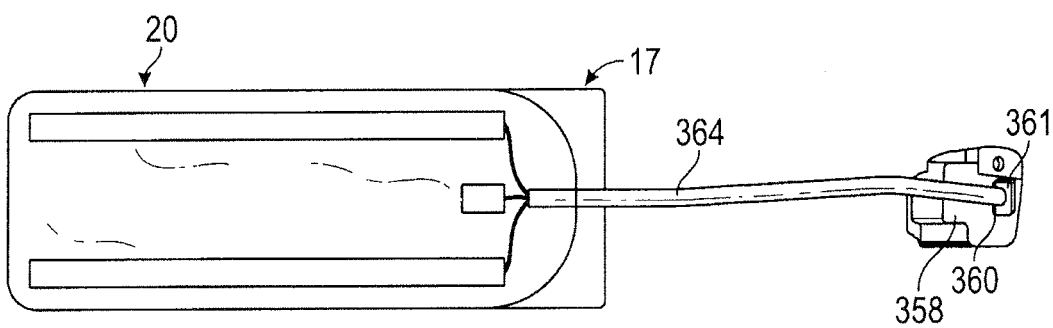
FIGS. 53A-53D are views of a housing for a receiver, a processor, and/or a transmitter, in accordance with aspects of the present disclosure.
Figure 53B:
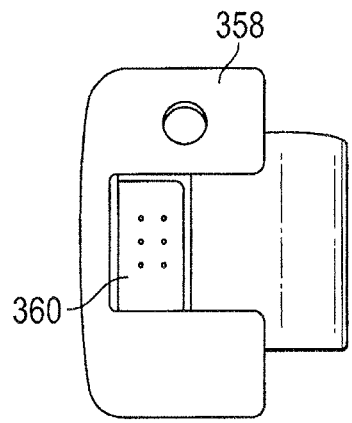
Figure 53C:
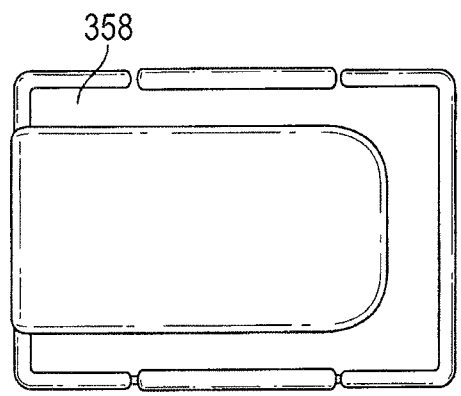
Figure 53D:
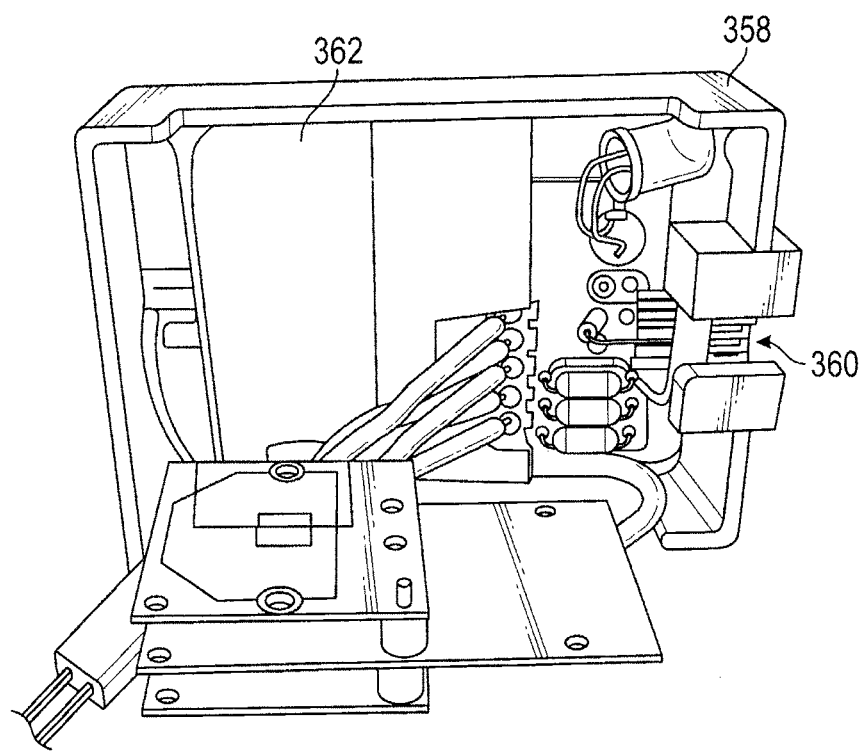

Additionally or alternatively, where device 17 includes multiple electrodes, parasitic capacitances between the electrodes (and/or their associated wires or traces) may cause fluctuations in the impedance of one pair, which may in turn impact the impedance measured between another electrode pair, leading to inaccuracy. This may occur because nearby electrodes and electrode wires may create a shunt capacitance (parasitic capacitance). When the impedance between a pair of electrodes is measured, the measurement may include the parasitic capacitance in the form of a parallel capacitor. When the electrodes and wires are moved or bent, the parasitic capacitance value may change, and therefore the measured impedance may also change. The ability to calculate the impedance and eliminate the interference caused by parasitics may be useful for improving accuracy. FIG. 52 shows an impedance model configured to take measured impedance values and convert them into impedance values of absorbent article 16. The model may achieve this by modeling system 10 as a network of electrodes 290*a*, 290*b*, 290*c*, each with a lattice of parasitic capacitances to each other electrode. Known impedance may be applied to each pair of electrodes. Measurements may then be taken and parasitic capacitances 324, 324*c* may be calculated. After determining the calibration of an impedance model, those inputs can be used to determine the impedance of absorbent article 16 by applying a more complicated version of the system described in FIG. 49. Given a measurement of impedance, the impedances of the absorbent article 369 and 369*a* can be solved for by solving the equivalent circuit provided in FIG. 52. One aspect is that the solution may be non-linear, and multiple approaches can be taken to solve for absorbent article impedances 369 and 369*a*. One such approach is to iterate on the solution, where the initial value of impedance 369 is calculated by assuming that impedance 369*a* is the measured value. The same process may be followed for impedance 369*a*. Once new values for impedances 369, 369*a* are determined, the process may be repeated with new impedances. The process may then be repeated until deviations between iterations are reduced below a certain threshold.

Leak Detection

In some instances, an enuresis event may miss absorbent article 16, the volume of fluid from the enuresis event may exceed the capacity of absorbent article 16, and/or absorbent article 16 may otherwise leak. Leakages typically require a changing of sheets on the wearer's bed, or additional cleaning. The ability to detect leakages may be helpful. In one example, one or more of sensing elements 20 is a conductive wetness sensing element configured for coupling on an exterior of absorbent article 16 to detect, by direct contact, moisture from a leak. The conductive wetness sensing element may be similar to conductive sensing elements shown in FIGS. 33A-33C, 34A-34D, 35A-35D.

Position Monitoring

According to one aspect, one or more of sensing elements 20 is configured such that system 10 may be used to monitor wearer positioning. Wearer positioning data can be communicated from sensing elements 20 to user interface 32 (via, e.g., receiver 22, processor 24, transmitter 26, and/or server 30) to provide relevant information to caregiver 12. For example, in one aspect, system 10 leverages position monitoring to reduce or prevent the onset of pressure sores. Typically wearers, such as facility residents or seniors, may be rotated to prevent pressure sore development. System 10 may aid in the management and optimization of rotating subjects by, for example, providing appropriate notifications to caregiver 12.

As part of its sensing elements 20, system 10 may utilize any combination of one or more of accelerometers, gyroscopes, magnetometers, and other suitable sensing elements, to monitor the position of wearer 14. Such sensing elements may, for example, be provided in any of the locations occupied by the above-described capacitive, conductive, and impedance sensing elements. Alternatively, the sensing elements may be provided separately and secured on absorbent article 16, wearer 14, or equipment in the vicinity of wearer 14. Additionally or alternatively, imaging techniques may be employed to monitor the position of wearer 14. Some exemplary imaging techniques include the use of cameras, infrared cameras, and ultrasound.

By monitoring the position of wearer 14, caregiver 12 may identify the need for repositioning wearer 14 to prevent the onset of pressure ulcers. The ability to detect wearer positioning and/or repositioning may play a role in optimizing the delivery of care to wearer 14. In one example, one or more of an accelerometer, gyroscope, magnetometer, and/or other suitable sensing element may be used to monitor the position of wearer 14 by, for example, detecting resident position and movement, and may be able to communicate this information to caregivers 12 via, for example, user interface 32. Using this information, caregiver 12 may be able to identify when wearer 14 should be repositioned or when wearer 14 should be left alone. As such, situations where caregiver 12 may unnecessarily wake wearer for repositioning may be avoided, thus reducing the occurrence of unnecessary sleep interruptions. Additionally or alternatively, caregiver 12 may be reminded to reposition wearer 14. As such, situations where caregiver 12 may forget to reposition wearer 14, increasing the wearer's risk of developing pressure ulcers, may be avoided, thus reducing the probability of wearer 14 spending excess periods of time in the same position.

Where an accelerometer is used to detect wearer orientation, in some instances transient motion of wearer 14 may interrupt or interfere with the detection of wearer orientation. An orientation detection algorithm that rejects transient motions may be used to mitigate such interruption/interference. In one example, an orientation detection algorithm detects wearer orientation after a period of signal stillness. For example after 5 seconds where a magnitude of a vector sum of acceleration is +/−10% of 9.8 m/s/s (subject to the error of the accelerometer in use), the acceleration vector can be taken as downward and the wearer orientation can be calculated based on that frame of reference. This technique assumes that when still, the accelerator will measure gravitational acceleration.

The orientation information may be communicated to caregiver 12 so that he or she can improve their workflow when changing wearer 14 or otherwise providing care to wearer 14. Orientation information can be presented to caregiver 12 in the form of the time wearer 14 has spent in his or her current orientation, and/or a history of wearer orientation over time.

Fall Detection

According to another aspect, one or more of the above-described sensing elements 20 for monitoring wearer positioning may be used to monitor if and when a fall has occurred. For example, if any of the sensing element signals falls outside of a predetermined range of values, and/or if a rate of change of any of the sensing element signals falls outside of a predetermined range of values, such occurrences may be indicative of a fall. Additionally or alternatively, one or more of the above-described imaging techniques can be employed to monitor the status of the individual and determine when a fall has occurred. A notification may be sent to user interface 32 upon detection of a fall, so that caregiver 12 may take the appropriate action.

Location Monitoring

According to another aspect, system 10 is used to monitor wearer location. Monitoring wearer location may be useful for planning caregiver workflow, and/or to prevent wearer 14 from wandering off or into restricted areas. In one example, device 17 includes one or more components, such as transmitter 26, that is worn by wearer 14, and utilizes Wi-Fi and/or Bluetooth networks to determine the location of wearer 14 relative to known and/or fixed Wi-Fi and/or Bluetooth transmitters. For example, the location of wearer 14 can be determined based on characteristics of one or more communications between device 17 and the known/fixed transmitters. Additionally or alternatively, imaging techniques may be employed to monitor the status of wearer 14 and determine his or her location. Some exemplary imaging techniques include the use of cameras, infrared cameras, and ultrasound to locate and/or track wearer 14. The location may be communicated to caregiver 12 via user interface 32.

Bowel Movement Detection

In some instances, even where caregiver 12 may be notified of a wetness event, caregiver 12 may still need to check absorbent article 16 for a bowel movement. It may be useful in such instances for system 10 to detect bowel movements. One or more of sensing elements 20 may be configured to detect bowel movements. It is also contemplated that such sensing elements may detect bowel movements in addition to moisture. Alternatively, separate sensing elements for detecting bowel movements and detecting moisture may be provided. One type of sensing element for detecting bowel movements is a methane sensing element. The methane sensing element may detect the presence of methane, and infer the presence of a bowel movement in, at, or near absorbent article 16 by comparing the methane level to a threshold indicative of the presence of a bowel movement. Depending on the sensitivity of the methane sensing element, a small bowel movement or other bodily function may trigger the methane sensing element without significant faeces being present in absorbent article 16. In order to distinguish significant bowel movements from insignificant ones, or to avoid false positives, system 10 may run a bowel movement detection algorithm that can differentiate between significant bowel movements and insignificant bowel movements/false positives. For example, the algorithm may utilize both a detection threshold on the presence of methane as well as a time threshold. Bowel movement detection may occur after the presence of methane exceeds a certain threshold for a certain amount of time.

Downstream System Features

As shown in FIG. 1, system 10 may include one or more receivers 22. Receiver 22 may include any suitable electronic device coupled to sensing element 20 via one or more wires or other conductors. Receiver 22 may be configured to communicate with sensing element 20. For example, receiver 22 may receive and/or collect sensing element data from sensing element 20. Receiver 22 may be positioned on absorbent article 16 (e.g., as part of device 17), near wearer 14, or on wearer 14.

System 10 may also include one or more processors 24 and transmitters 26. Processor 24 may be configured to receive sensing element data from receiver 22, or directly from sensing element 20, via one or more wires or other conductors. Processor 24 may perform at least some initial processing of the received sensing element data, and may send one or more signals based thereon to server 30. It is contemplated that the same receiver 22, processor 24, and transmitter 26 may be used for capacitive, conductive, and/or impedance sensing arrangements.

In one example, receiver 22, processor 24, and transmitter 26 are integrated in, or contained within, a housing 358, shown in FIGS. 53A-53D. Housing 358 includes a port 360 configured to receive a plug 361 of a connector 364, wherein connector 364 may be connected to one or more of sensing elements 20. Housing 358 may be secured to any of substrates 18. For example, housing 358 may be positioned within a pocket of any of substrates 18. Housing 358 may also contain a power source (e.g., a battery) 362 for powering device 17. Battery 362 may include, for example, a rechargeable 100 mAH LiPo battery.

Processor 24 may include any suitable board or microcontroller platform, such as an Arduino board. Transmitter 26 may include a WiFi chip, or any other suitable electronic transmitter. Transmitter 26 may send signals to server 30 over the Internet via any suitable form of wireless communication, such as Bluetooth, 3G, 4G, and/or WiFi.

Processor 24 may check the activity of circuitry in device 17 at predetermined intervals, such as ten times per second. Using a conductive sensing arrangement as an example, when a wetness event occurs, a resistance across two pieces of conductive fabric may be reduced, leading to a change in the voltage across an analog to digital conversion (ADS) in processor 24. The voltage change (signal) may be converted to a number (n1) between 0-1023. Processor 24 may add n1, n2, n3, . . . , n600 (ten times per second by sixty seconds per minute) to create a running sum for each one minute block and store this value (N). Processor 24 may store running sums for fifteen one-minute blocks. Processor 24 may store changes in plug status and active plug status over a fifteen-minute period (which may be determined through the connection of a separate circuit). Processor 24 may activate transmitter 26 to push sensing element data and plug status data to server 30 every fifteen minutes via WiFi. If WiFi is down, processor 24 may continue to store data for an additional fifteen-minute interval. The ADC conversion, LED and sensing element connection circuitry that processor 24 may monitor may rely on an external printed circuit board (PCB).

Processor 24 may run one or more of the above-described models and algorithms using the sensing element data as inputs, to characterize wetness events. Processor 24 may send output signals, via transmitter 26, to server 30 and/or user interface 32, to notify caregivers 12 based on one or more criteria. For example, notifications may be sent when absorbent article 16 reaches a certain threshold, or caregivers 12 may be notified when the chance of a leakage occurring in absorbent article 16 is high (e.g., above a predetermined threshold). Alternatively, the models and/or algorithms, or portions thereof, may be implemented on server 30. In other words, processor functions may be distributed between processor 24 on wearer 14 and server 30.

Figure 54A:
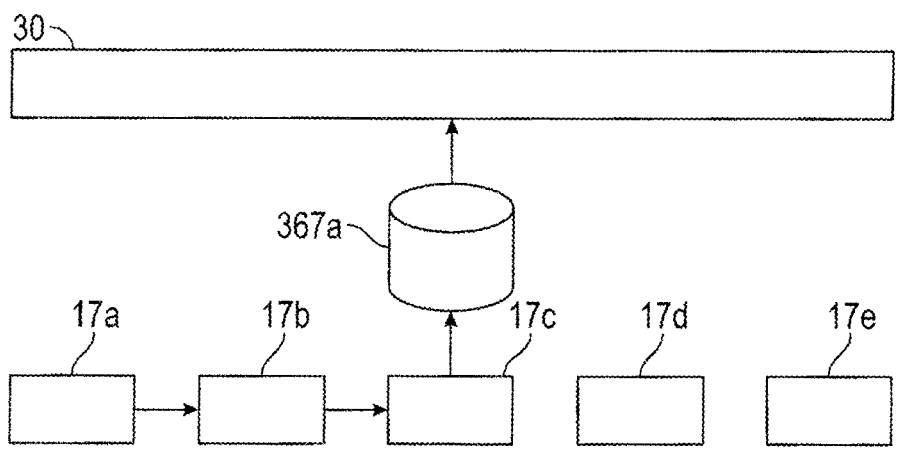
FIGS. 54A-54C are schematics of communication pathways between devices and a server, in accordance with aspects of the present disclosure.
Figure 54B:
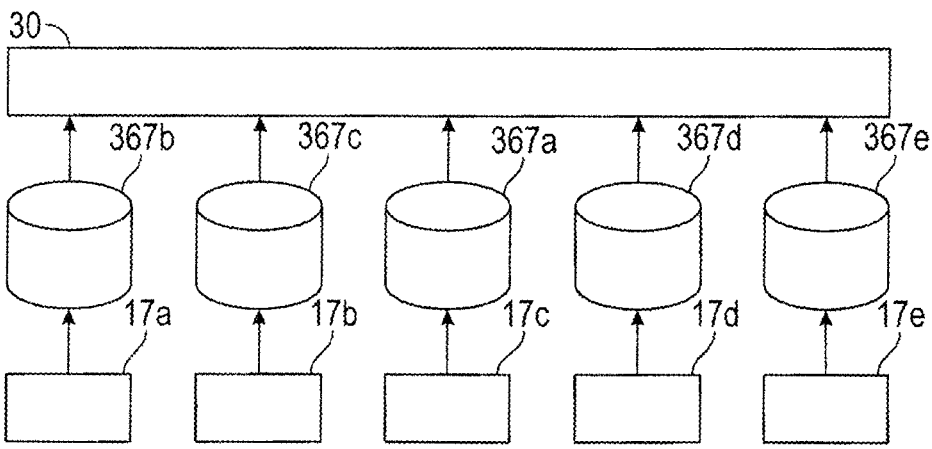
Figure 54C:
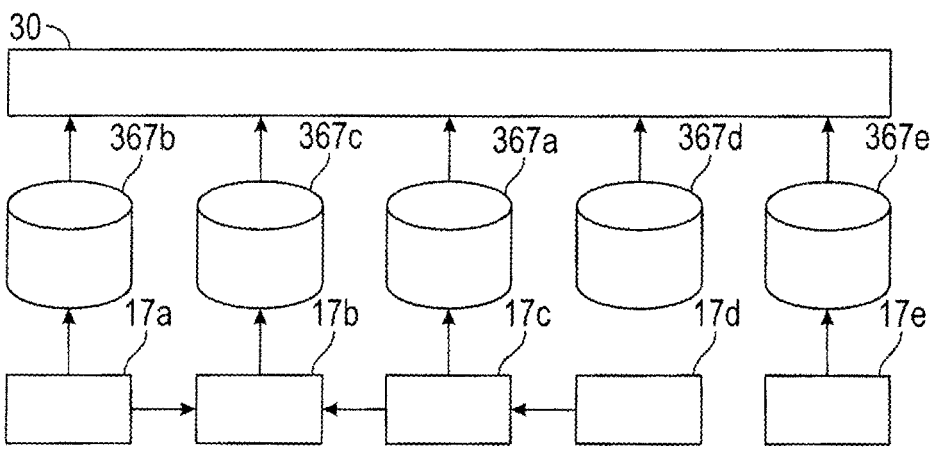

In examples shown in FIGS. 54A-54C, communication between devices 17a-17e and server 30 take place through one or more bridges 367a-367e. Devices 17a-17e communicate with each other and/or with one or more of bridges 367a-367e using Bluetooth. For example, receivers 22 of one or more of devices 17a-17e receive data from transmitters 26 of one or more of the other devices 17a-17e via Bluetooth. Transmitters 26 of one or more of devices 17a-17e may transmit data to one or more of bridges 367a-367e via Bluetooth. One or more of bridges 367a-367e may then communicate with server 30 using WiFi, 3G, 4G, and/or another suitable network communication protocol. Each of bridges 367a-367e may, for example, include a Bluetooth dongle to communicate with devices 17a-17e, and a WiFi dongle to link to the Internet. Bridges 367a-367e may be placed in locations around a facility in which wearers 14 reside in fixed locations or mobile locations (i.e., attached to wearers 14 or equipment used by wearers 14). Devices 17a-17e may execute a Bluetooth scan to search for bridges 367a-367e, and may initiate a connection to an available bridge. Once the connection is initiated, devices 17a-17e may transmit/free data after an acknowledgement from the available bridge.

As shown in FIG. 54A, devices 17a-17c communicate with each other until messages reach device 17c, which is in range of bridge 367a. Bridge 367a may serve as the conduit for the messages from devices 17a-17c to reach server 30. Alternatively, as shown in FIG. 54B, each of devices 17 may communicate with server 30 through its own bridge 367a-367e. Alternatively, as shown in FIG. 54C, devices 17 communicate with each other over Bluetooth until a message or signal reaches one or more of devices 17 in range of sparse bridges 367a-367e. The message may then be passed to the bridge (any of bridges 367a-367c) and to server 30. It is also contemplated that mobile Bluetooth to WiFi bridges may be provided in the form of battery-powered bridges placed in a pocket on a wheelchair or other equipment.

Server 30 may receive one or more signals from transmitter 26 directly, or via bridges 367a-367e. Server 30 may also run part of the above-described algorithms and/or models. Additionally or alternatively, server 30 may process one-minute averages recorded by receiver 22, processor 24, and/or transmitter 26, and may display the data and notify caregivers 12, when appropriate, via text message or other suitable alert.

Server 30 may include one or more components, such as, for example, a proxy server hosted, for example, on Amazon AWS, a MeteorJS server for data storage, visualization, monitoring signals, and/or notifying caregivers when action may be desired. It is also contemplated that data storage, visualization, monitoring signals, and/or notifying may be separated across multiple MeteorJS servers. Requests made to the proxy server may be forwarded to the MeteorJS server. Device 17 may make requests to the proxy server (from transmitter 26) and they may be forwarded to the MeteorJS server.

Figure 55:
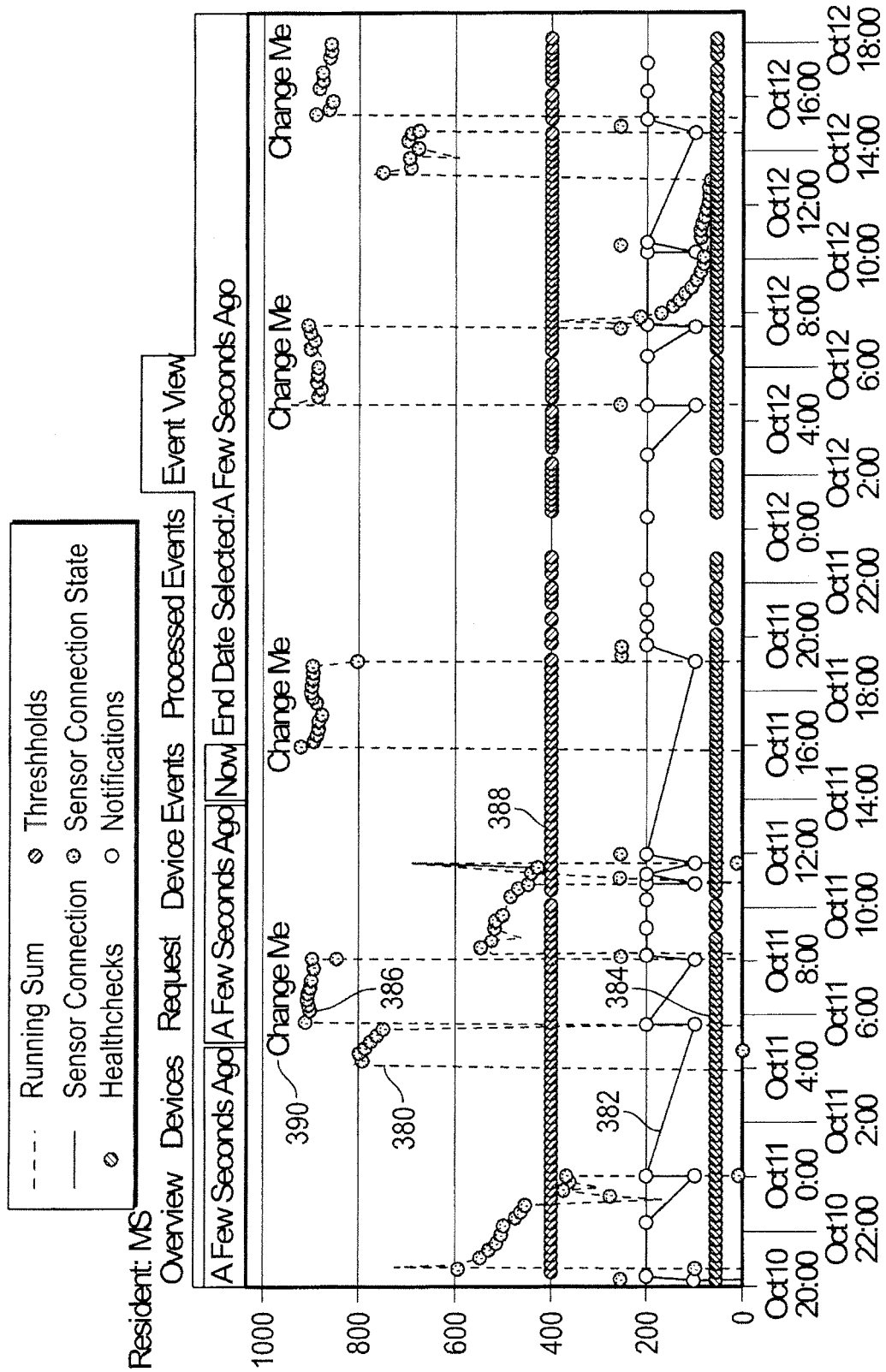
FIG. 55 is a graphical representation of server data, in accordance with aspects of the present disclosure.

When server 30 receives requests from device 17, it may follow the steps outlined below. Server 30 may receive raw and/or processed sensing element data. Server 30 may process the data into events. The events may be plotted on a graph as a function of time. The newly plotted values may be compared with each other and the values from the last fifteen minutes of data to determine whether equilibrium exists (e.g., when, over a four-minute interval, the values within a predetermined range of one another). FIG. 55 shows a visualization of the data on server 30, wherein a running sum line 380 is indicative of running averages calculated by processor 24, a sensor connection line 382 is indicative of a status of a sensing element connection, healthcheck dots 384 are indicative of points at which device 17 made a request to server 30, threshold dots are indicative of changes of state regarding a sensing element being plugged in or unplugged, sensor connection state dots 386 are indicative of whether a sensing element was plugged or unplugged at the time a request was made, and "change me" is an example of notifications to caregiver 14 requesting, for example, changing of absorbent article 16.

Additionally or alternatively, server 30 may take the processed series of events and perform tasks, such as searching for equilibria or regions where sensing element signals may be stable. Equilibrium regions may be determined by looking for regions of the sensing element signals that experience limited deviation over several minutes. Volumes may only be calculated from equilibrium values due to the peak in signal values that occurs when the user urinates on absorbent article 16. The peak values produced shortly after urination may typically be high and not related to the size of the urination event. By calculating volumes from equilibrium values, these peaks may be filtered out.

Figure 56:
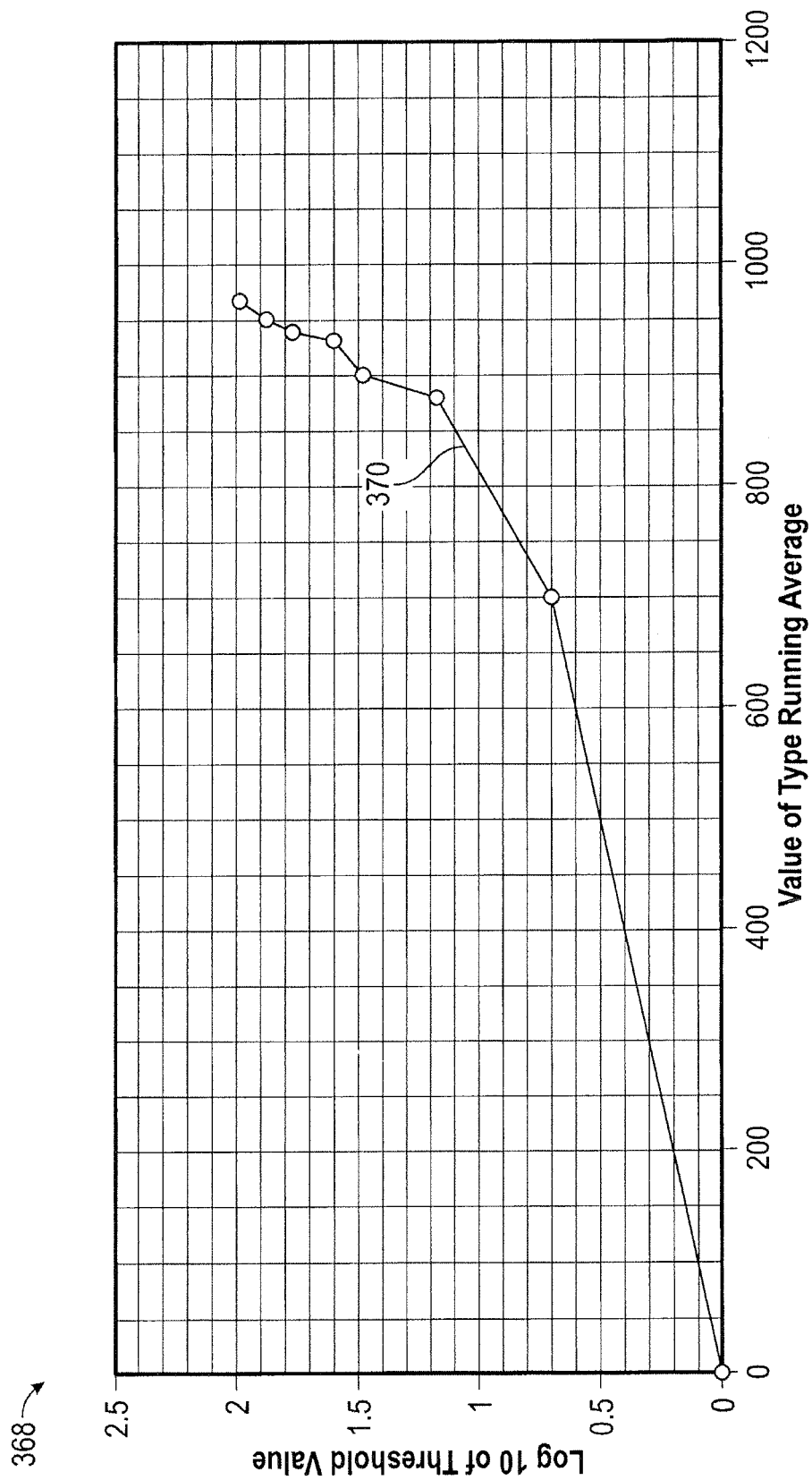
FIG. 56 is a graph indicative of running average values versus threshold values, in accordance with aspects of the present disclosure.
Figure 57A:
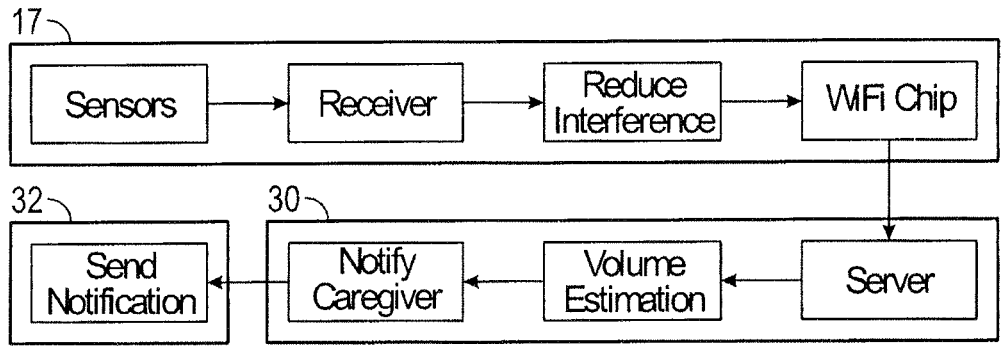
FIGS. 57A-57D are schematics of various system flows, in accordance with aspects of the present disclosure.
Figure 57B:
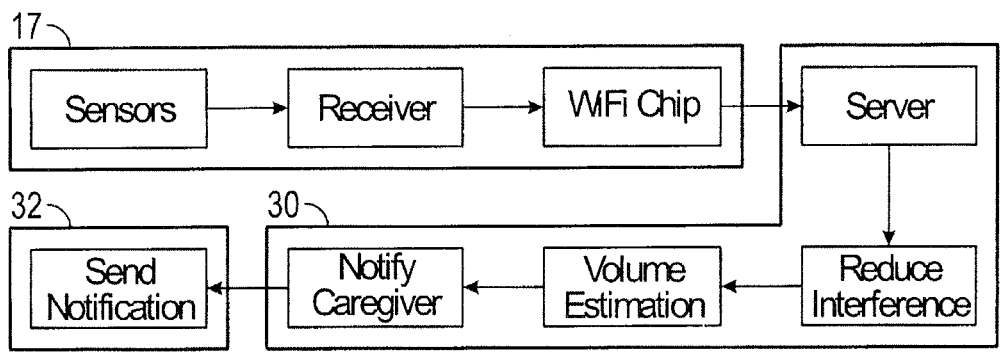
Figure 57C:
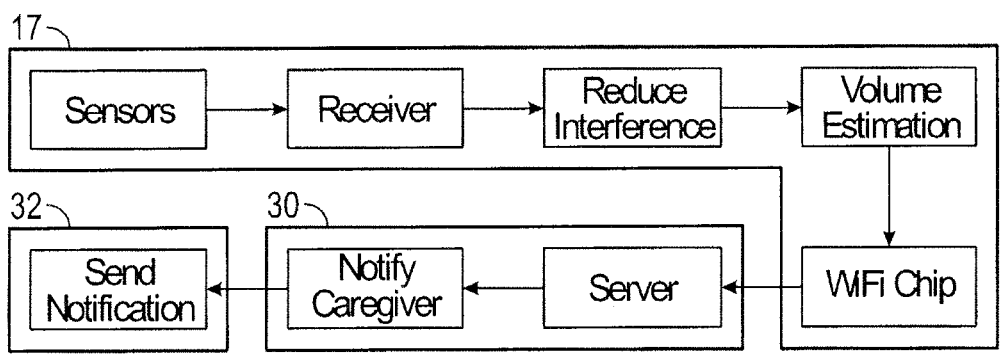
Figure 57D:
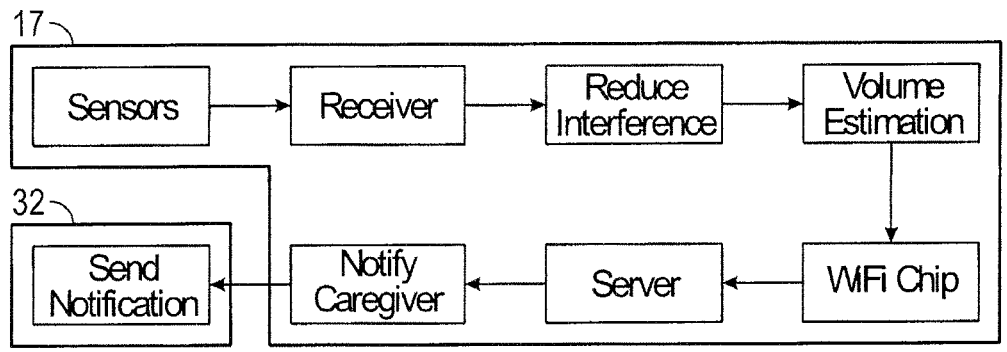

If an equilibrium exists between a certain number of events, the first event of the time interval for which equilibrium exists may be used to lookup a corresponding threshold value for absorbent article 16 (the mapping between the value of events of type running average and the absorbent article's threshold values may be determined empirically, with an exemplary look up table, generated using linear interpolation, in the form of an exemplary graph 368 and curve 370 shown in FIG. 56. Data points used to generate graph 368 may be collected by urinating in a series of absorbent articles 16 and weighing them after each urination. The data collected may be across several brands and types of absorbent articles 16. Once sensing element signals have been converted into volumes, server 30 may send text messages, or other notifications, to caregivers 12, if the converted volume exceeds a predetermined and/or preset threshold.

User interface 32 may be used for communicating with caregivers 12. User interface 32 may include any suitable display for communicating information to caregivers 12, including a display on a smartphone, laptop computer, desktop computer, and/or other electronic equipment. User interface 32 may also include speakers, or any other suitable sound generating devices, to communicate information to caregivers 12. The information user interface 32 may convey may include wetness status of wearers 14, alerts to perform tasks, and/or general data about wearers 14 and/or system 10. In one example, the information user interface 32 conveys one or more indications of whether wearer 14 should be changed, whether a leakage from absorbent article 16 has occurred, whether a leakage from absorbent article 16 is likely to occur, and/or whether wearer 14 should be toileted.

User interface 32 may be controlled by electronic applications or other software to perform the above-described functions. For example, notifications may be prepared by server 30 to appear on user interface 32 based on predetermined criteria identified, for example, in the data received by server 30 from devices 17. In one example, a Twilio application program interface (API) is used to send notifications in the form of text messages to user interface 32. Notifications can also be in the form of push notifications, integrated notifications with a call bell system, phone calls, and/or integration notifications with a point of care systems. Notifications may be sent for a variety of reasons and in a variety of forms. For example, notifications may be sent when absorbent article 16 is close to capacity. That is, when the estimated volume is above some determined maximum volume for that absorbent article 16 and/or wearer 14. The notifications may include visual, auditory, or tactile alerts sent, for example, to an electronic device, of which user interface 32 is a part, carried by caregiver 14. Additionally or alternatively, alerts may be sent to equipment in a wearer's vicinity. Additionally or alternatively, device 17 may include one or more alerting components, such as a light source and/or a sound generator, for communicating alerts.

FIGS. 57A-57D show exemplary system flows culminating in a notification being sent to user interface 32 using, for example, an API. The system flow shown in FIG. 57A has sensors 20 sensing a wetness event and sending signals to receiver 22, receiver 22 sending signals to processor 24 for processing to reduce interference, processor 24 sending signals to transmitter 26 (e.g., a WiFi chip), and transmitter 26 sending signals to server 30 (e.g., over the Internet). Server 30 may receive the signals, run one or more algorithms/models on the signals for volume estimation (and/or for identifying other characteristics of a wetness event), and send a notification to caregiver 12 via user interface 32. The system flow shown in FIG. 57B differs from the system flow shown in FIG. 57A in that processing for reducing interference takes place on server 30, rather than on device 17. The system flow shown in FIG. 57C differs from the system flow shown in FIG. 57A in that processing for volume estimation and the like takes place on device 17, rather than on server 30. The system flow shown in FIG. 57D differs from the system flow shown in FIG. 57A in that server 30 is omitted.

Workflow Enhancement

System 10 may enhance the ability of caregivers 12 to provide care to wearers 14. For example, caregiver 14 may utilize user interface 32 to access data in system 10, to check a wearer's wetness status during the night, before waking up wearer 14. Caregiver 12 may be prompted to check by a receiving a notification, or on his or her own volition.

System 10 also may be used to enhance caregiver workflow in a care facility setting. Workflow enhancements may include, for example, asynchronously checking and/or changing wearers 14, prioritizing wearer care, determining care activity required for certain wearers 14, determining when caregivers 12 should conduct a round of checks, determining which wearers 14 should be included on a round of checks, and other enhancements. For example, system 10 may notify caregivers 12 when a wearer's absorbent article 16 is approaching capacity and requires changing. The notification may be sent to caregivers 12 upon values from sensing elements 20 and/or processor 24 reaching a saturation percentage threshold, volume threshold, capacitance threshold, and/or impedance threshold. Notifications may be postponed immediately following a change to allow for caregivers 12 to continue with their activities. For example, automatic notifications may be delayed by a set number of minutes after the most recent change.

In order to enhance caregiver workflow, system 10 may present caregivers 12 with information that may be helpful for deciding what type of care should be administered. Types of care may include, but are not limited, to checking a wearer's absorbent article 16, changing a wearer's absorbent article 16, applying barrier cream to wearer 14, visually checking wearer 14, and toileting wearer 14. System 10 may present information pertaining to wearer location, most recent change, saturation percentage, volume of liquid, duration of time spent in a wet absorbent article 16, absorbent article capacity, integral of volume of liquid over time, and/or wearer skin integrity, to assist caregivers 12 with making determinations on the administering of care. For example, system 10 may recommend the type of care caregiver 12 should administer to wearer 14. This automatic care type determination may be based on developing a weighted cost function that calculates a cost for each wearer 14 by adding up a weighted sum of wearer distance to caregiver 12, amount of time since most recent change, saturation percentage, volume of liquid, duration of time spent in a wet absorbent article 16, absorbent article capacity, and/or integral of volume of liquid over time. In one example, checking a wearer's absorbent article 16 may be suggested when the cost function exceeds a given threshold. Changing a wearer's absorbent article 16 may be suggested when the cost function exceeds another given threshold.

System 10, and/or a caregiver 12 using system 10, also may use data in system 10 to attempt to optimize caregiver workflow. Optimization of caregiver workflow may include changing the order of caregiver tasks and/or degree of care provided to wearers 14. Steps for optimizing may include monitoring the wetness state and/or wetness events of one or more absorbent articles 16 with sensing elements 20, processing the wetness states and/or wetness events with processor 24 and/or server 30, communicating said processed wetness states and/or wetness events to one or more caregivers 14 via user interface 32. User interface 32 may communicate that certain wearers 14 of absorbent articles 16 may be at a higher priority of receiving care than others. The priority of wearers 14 may be determined by ranking wearers 14 by a score that may be generated by any of the above-described predetermined mathematical models/algorithms. The priority of wearers 14 may, for example, be a function of one or more characteristics of wearers 14 and/or absorbent articles 16 as identified by one or more of sensing elements 20.

As part of the optimization, system 10 may present caregiver 12 with information caregiver 12 may use to prioritize providing care to wearers 14. The information presented may pertain to wearer location, most recent change, saturation percentage, volume of liquid, duration of time spent in a wet absorbent article 16, absorbent article capacity, integral of volume of liquid over time, and/or wearer skin integrity. In one example, system 10 may prioritize wearers 14 who are in need of changes and/or checks. Automatic prioritization may be conducted by developing a weighted cost function that calculates a cost for each wearer 14 by adding up a weighted sum of wearer distance to caregiver 12, amount of time since most recent change, saturation percentage, volume of liquid, duration of time spent in a wet absorbent article 16, absorbent article capacity, and/or integral of volume of liquid over time.

Additionally or alternatively, user interface 32 may communicate that wearers 14 associated with certain absorbent articles 16 may require certain types of care. The types of care communicated may include, but are not limited to, checking on the status of absorbent article 16 or changing absorbent article 16. The types of care communicated may be determined by applying a threshold to a score that may be generated by any of the above-described predetermined mathematical models/algorithms. For example, the types of care communicated may be a function of one or more characteristics of one or more of sensing elements 20.

Using conventional methods, caregivers 12 may generate toileting plans for wearers 14 based on enuresis event histories. The process for doing so may include creating a voiding diary, and suggesting times throughout the day when wearers 14 should be brought to the toilet before they have an incontinent episode. Commonly, such toileting plans may be generated across a 72-hour assessment period. One circumstance that may arise is that a toileting plan may become inefficient as voiding patterns change over time. According to one aspect, system 10 may present a voiding diary to caregivers 12 (e.g., nurses, directors of nursing, and/or administrators) so that they may manually generate toileting plans. Moreover, the voiding diary may be updated in real-time as system 10 gathers data, thus ensuring their accuracy, and the accuracy of toileting plans based thereon.

Additionally or alternatively, system 10 may attempt to autonomously predict enuresis events so that caregiver 12 may bring wearer 14 to the toilet and prevent an enuresis event into absorbent article 16. To achieve this, system 10 may apply one or more algorithms to a series of inputs including, for example, enuresis event history, time since the last enuresis event, size of the last enuresis event, and/or fluid intake history. It is also contemplated that enuresis events may be predicted by applying a machine learning algorithm to a time series of enuresis event data. For each enuresis event, features may include an array of previous enuresis events (time and size), an array of previous fluid intakes (time and volume), and demographic information. It is also contemplated that enuresis events may be predicted by looking at historic enuresis events. Given data collected from previous days and weeks, unsupervised machine learning may be applied to determine the most likely times of urinations.

User Interface Flow Diagrams

Figure 63:
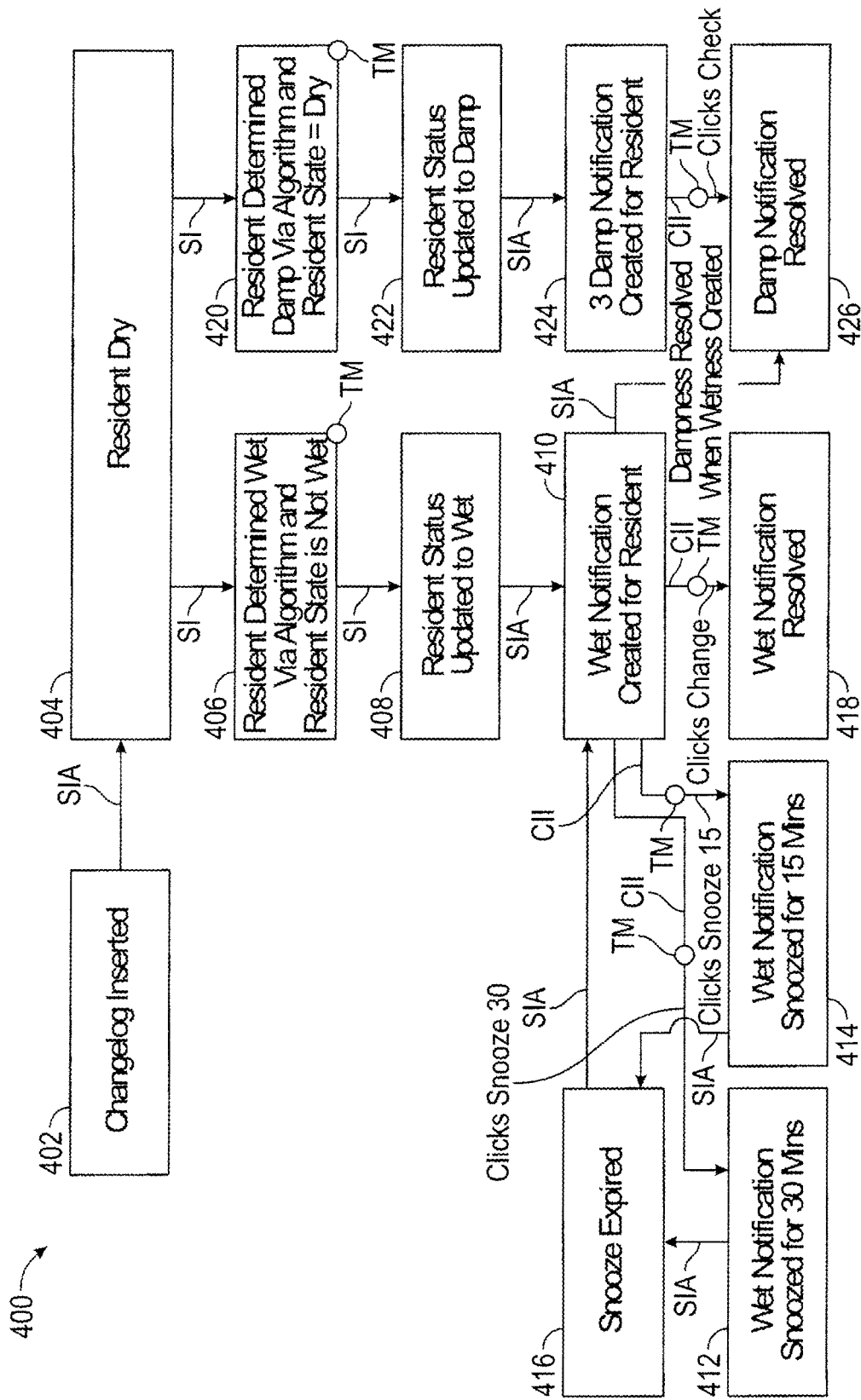
FIG. 63 is an exemplary process diagram, in accordance with aspects of the present disclosure.

FIG. 63 shows an exemplary process diagram 400 with steps that may be performed via system 10 for wearers (residents) 14. In diagram 400, "SI" is shorthand for "sensor initiated," "CII" is shorthand for "caregiver iPad initiated," "SIA" is shorthand for "server initiated (autonomous)," and "TM" is shorthand for "text message sent to system staff," the system staff referring to personnel with responsibility for operating system 10. With step 402, server 30 logs a change of absorbent article 16 worn by wearer 14. With step 404, system 10 sets a status of wearer 14 as being dry, at the initiation of server 30.

With step 406, system 10 determines that wearer 14 is wet (after being in a non-wet state) using any of the above-described sensors 20, models, and algorithms, at the initiation of sensors 20. A text message is sent by system 10 to the system staff regarding this determination. With step 408, system 10 updates/sets the status of wearer 14 as wet, also at the initiation of sensors 20. With step 410, a notification that wearer 14 is wet is created, at the initiation of server 30. With step 412, system 10 recognizes that caregiver 12 has hit snooze on the wet/wetness notification, thereby resetting or putting off the notification for 30 minutes, by manipulating (e.g., by touching, clicking, etc.) user interface 32 on a caregiver iPad or other suitable computing device. Step 414 is similar to step 412, but the time period may be 15 minutes instead of 30 minutes. Text messages may be sent by system 10 to the system staff regarding the caregiver's use of the snooze function. With step 416, the time period associated with the snooze function has expired, and the process returns to step 410 for another wet notification to be created. With step, 418, system 10 recognizes that caregiver 12 has changed wearer 14, thereby resolving the wet notification, via caregiver 12 manipulating the iPad accordingly. With the wet notification resolved, the process ends, or returns to step 402.

With step 420, system 10 determines that wearer 14 is damp (after being in a dry state) using any of the above-described sensors 20, models, and algorithms, at the initiation of sensors 20. A text message is sent by system 10 to the system staff regarding this determination. With step 422, system 10 updates/sets the status of wearer 14 as damp, also at the initiation of sensors 20. With step 424, at least one damp/dampness notification for wearer 14 is created, at the initiation of server 30. With step 426, system 10 recognizes that caregiver 12 has checked wearer 14 for dampness, thereby resolving the dampness notification, via caregiver 12 manipulating the iPad accordingly. With the dampness notification resolved, the process may end, or may return to step 402. The creation of a wetness notification at step 410 may also resolve the dampness notification.

Figure 64:
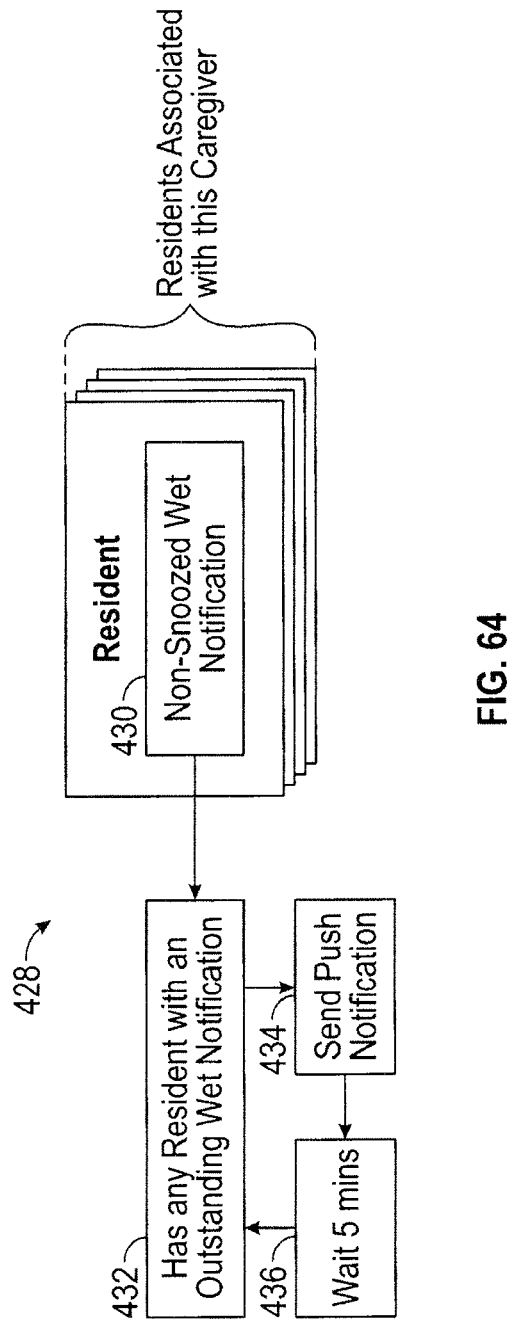
FIG. 64 is an exemplary process diagram, in accordance with aspects of the present disclosure.

FIG. 64 shows an exemplary process diagram 428 with steps that may be performed via system 10 for caregivers 12. Each caregiver 12 may be tasked with handling the needs of a plurality of wearers 14 (residents). With respect to step 430, system 10 generates a non-snoozed wet/wetness notification (see, e.g., step 410 in FIG. 63) for one or more of wearers 14. System 10 determines, at step 432, whether caregiver 12 has any wearer 14 with an outstanding wet/wetness notification. If so, system 10 generates/sends a push notification to caregiver 12 at step 434. The push notification may appear on user interface 32 of the caregiver's iPad. With step 436, system 10 waits for a period of time (e.g., five minutes), for caregiver 12 to resolve the wetness notification (see, e.g., step 418 in FIG. 63). After the time period has elapsed, system 10 returns to step 432, effectively running a loop of checking for wetness notifications, sending push notifications, and waiting for caregiver action, until the wetness notifications have been resolved.

User Interface Usage Instructions

Figure 65:
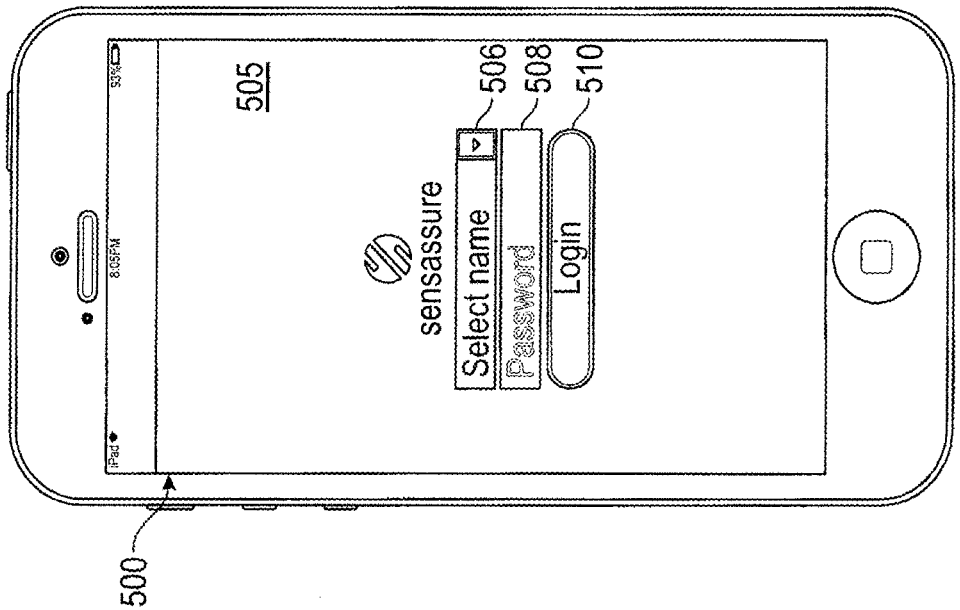
Figure 66:
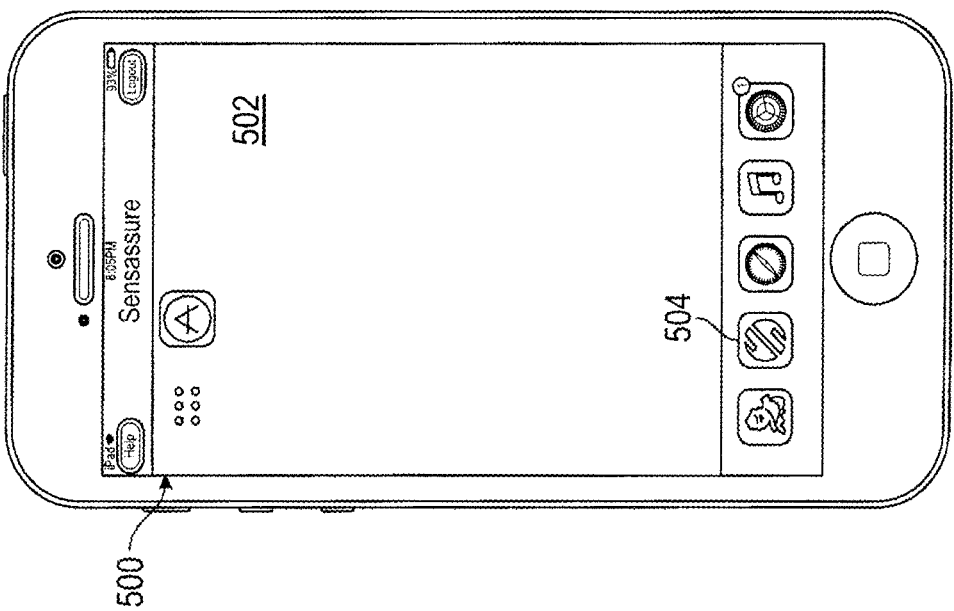
Figure 68:
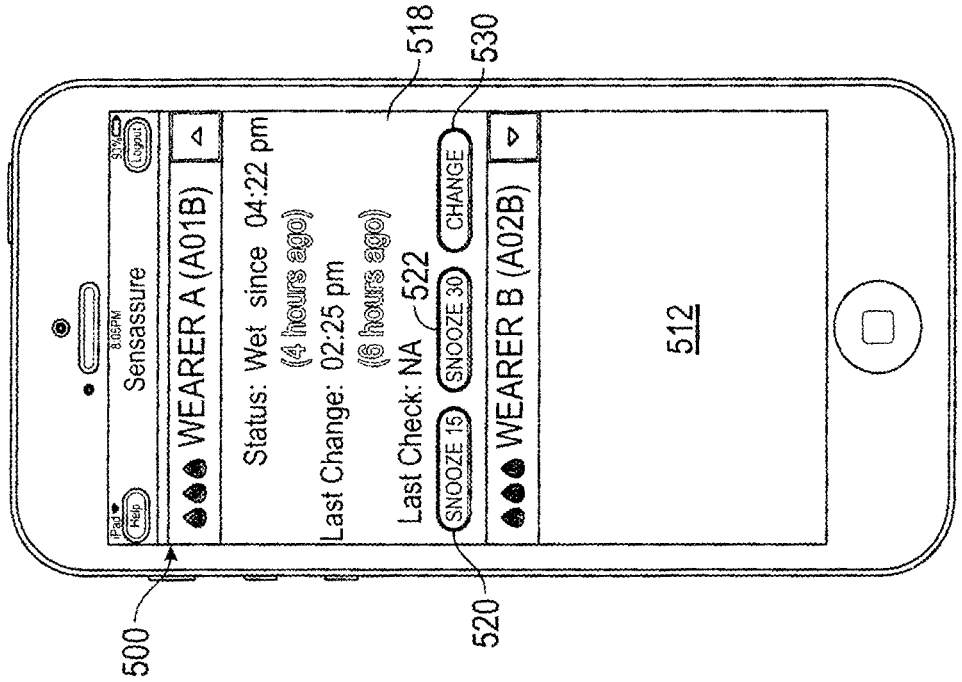
Figure 67:
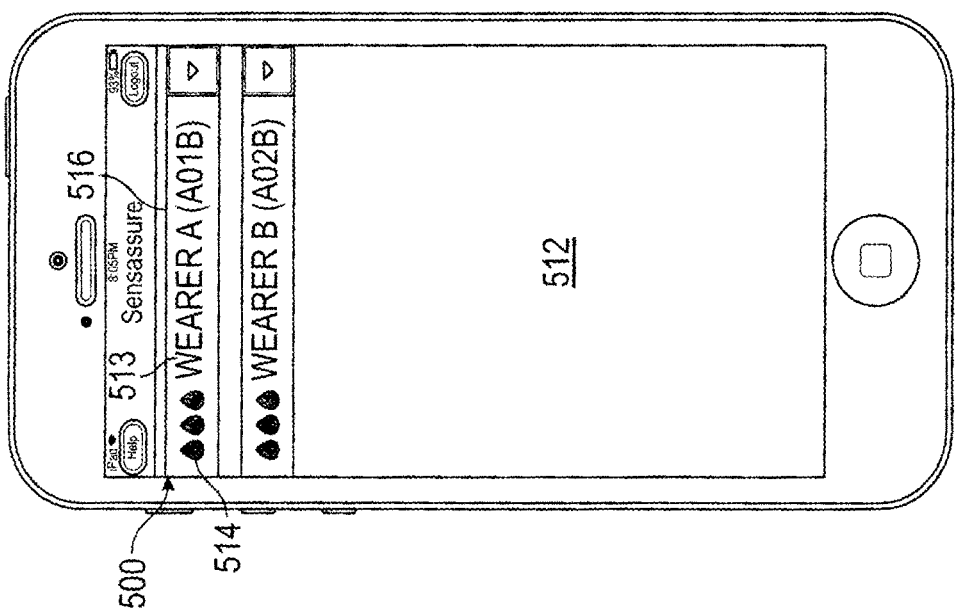
Figure 72:
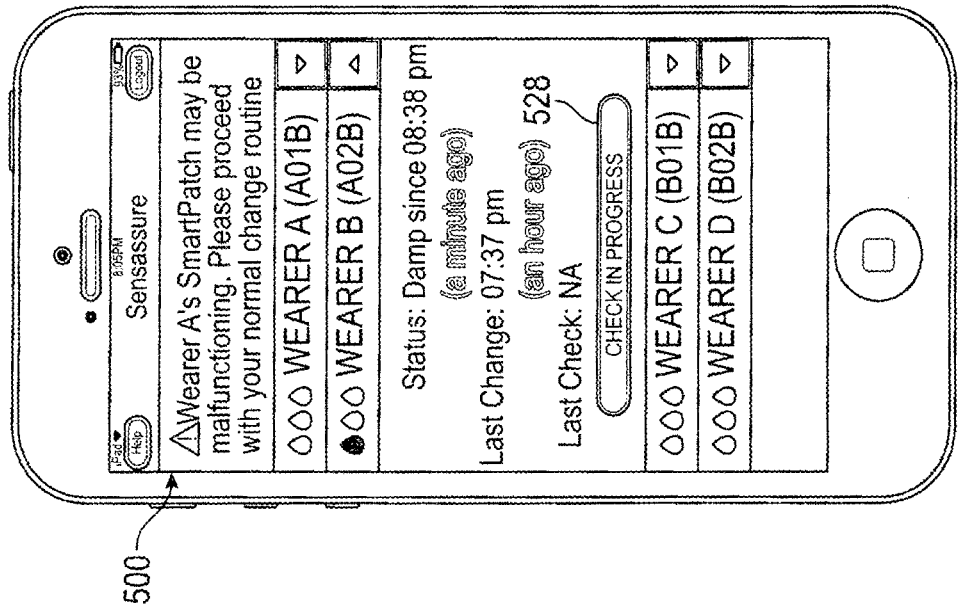

FIGS. 65-78 show screenshots from an iPad screen 500. FIG. 65 shows the home screen 502, with an icon 504 for an application in operative communication with system 10. Caregiver 12 may click on icon 504 to launch the application. When the application launches, a login screen 505 appears, as shown in FIG. 66. Caregiver 12 may select his or her name using a dropdown menu 506, and enter his or her password in a password field 508. Caregiver 12 may then login by clicking button 510. This will bring them to the application's home screen 512, shown in FIG. 67. Once logged in GNA's will be brought to the home screen where they will be able to see the names and/or locations 513 of wearers 14 (residents), and the status of the wearers 14. Information about wearers 14 may be conveyed to caregiver 12. For example, one or more indicators 514 may tell caregiver 12 whether a wearer 14 is dry, damp, or wet (0 blue water droplets means the resident is "dry," 1 blue water droplets means the resident is "damp," 3 blue water droplets means the resident is "wet"). A box 516 around the resident means a change notification exists for that resident which has not yet been snoozed (FIGS. 63, 64).

To view more information on their wearers 14, caregivers may click on wearers 14, which may reveal a drop down window or menu 518 with additional information, such as wearer status (e.g., if they are "wet," "damp," or "dry", when their status last changed and how long ago it was, the last change time and how long ago it was, and the last check time and how long ago it was. The check time may only be displayed if it occurs after a change. Checks which may be further back in time than the last change may not be displayed.

To snooze a change notification, caregiver 12 presses or clicks on buttons 520, 522 labeled "Snooze 15" or "Snooze 30" which will snooze the application from sending notifications for 15 or 30 minutes, respectively. Once a snooze button is pushed, snooze buttons 520, 522 disappear, as shown in FIG. 69. Snooze buttons 520, 522 reappear after 15 or 30 minutes has elapsed.

Figure 71:
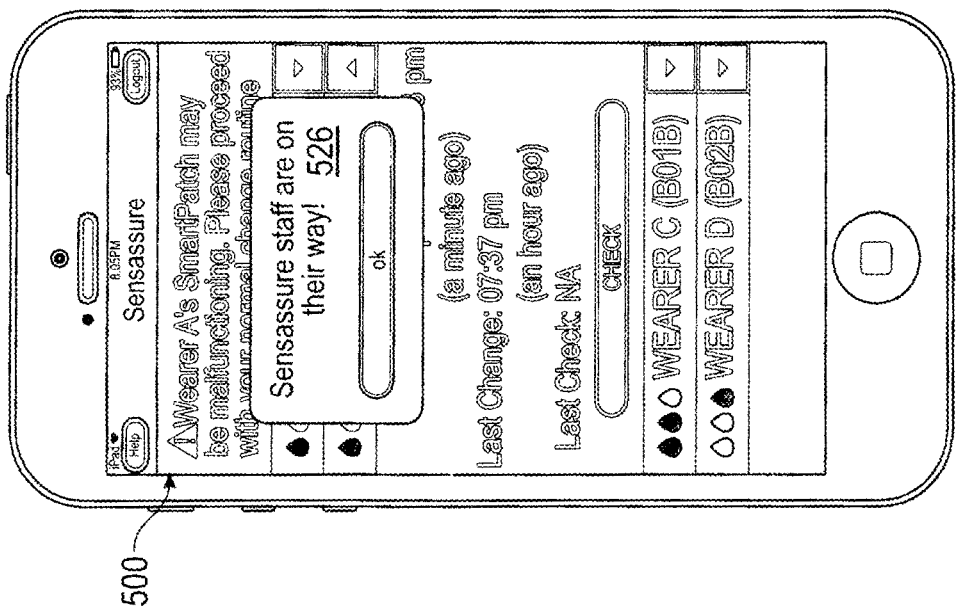

When wearer 14 is damp, caregiver 12 may not receive a push notification. However, if caregiver 12 checks home screen 512, he or she will see the damp wearer 14 with one blue droplet. If caregiver 12 clicks on that wearer 14, he or she is presented with the option of clicking a "check" button 524, as shown in FIG. 70. If caregiver 12 clicks check button 524, a pop-up 526 notifies them that system staff are on their way, as shown in FIG. 71. After caregiver 12 acknowledges this, he or she is brought back to the resident specific screen, shown in FIG. 72, and it displays a "check in progress" bar 528 until system staff manually enter(s) a check on an online change log.

Figure 74:
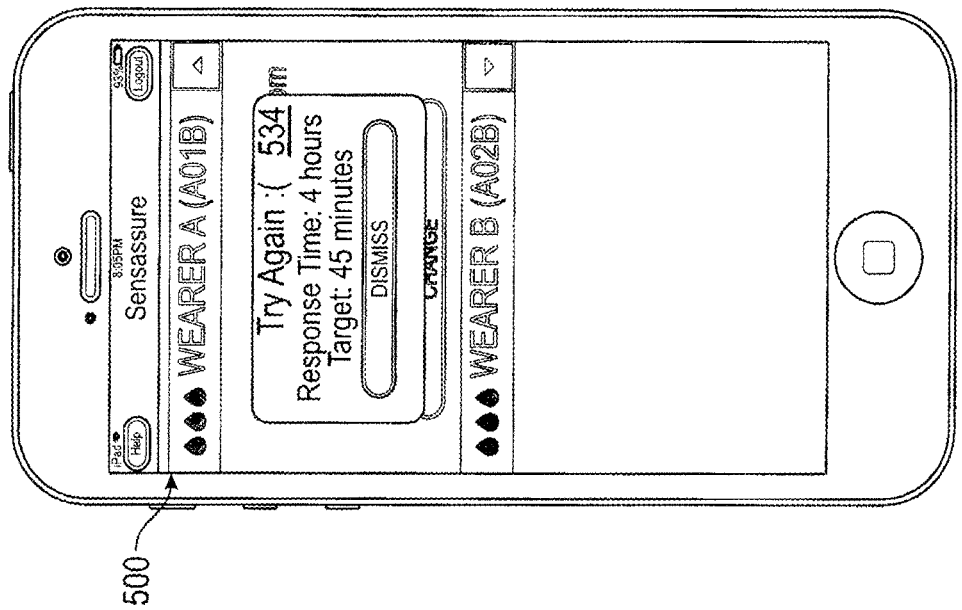
Figure 73:
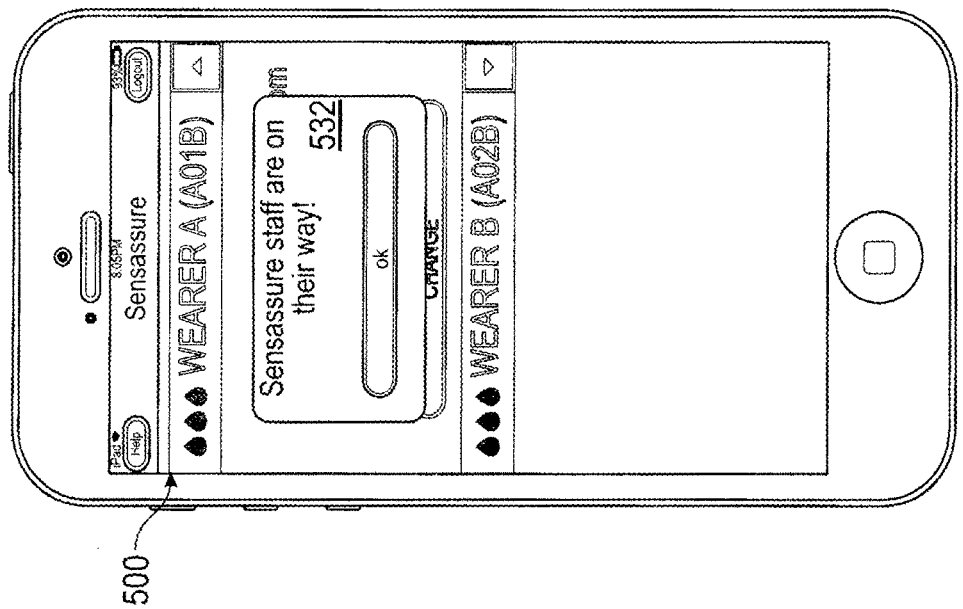
Figure 76:
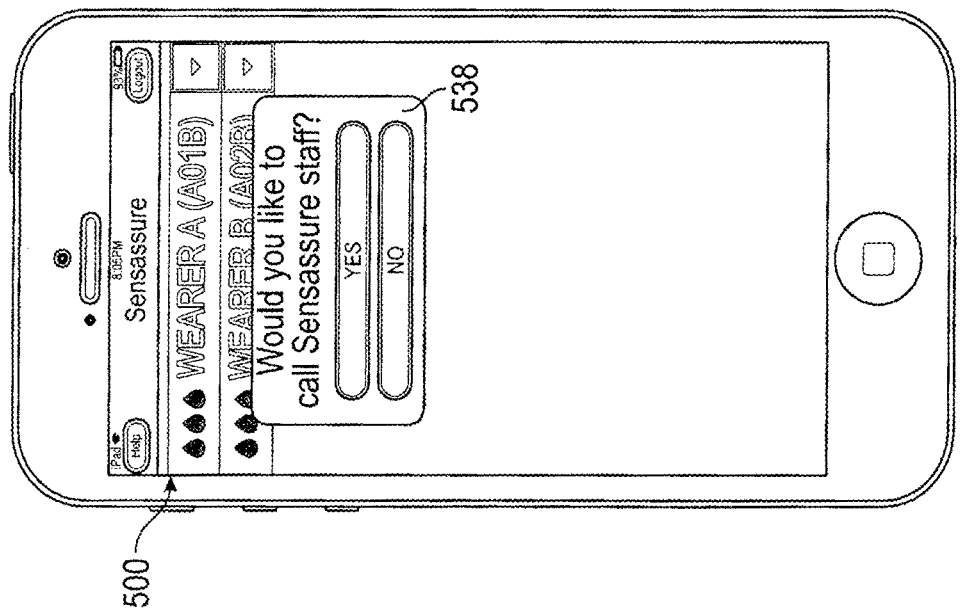
Figure 75:
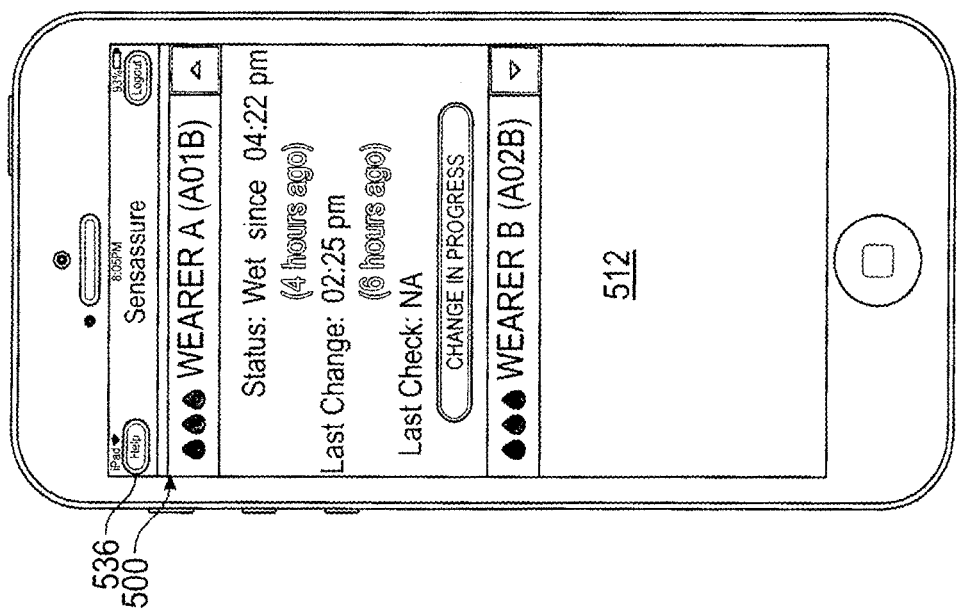

When a wearer 14 is wet, caregivers 12 receive an audible push notification immediately upon system 10 detecting the wearer 14 as wet, and every 5 minutes thereafter, unless the notification is snoozed. Wet wearers 14 appear with 3 blue water droplets beside their name on home screen 512. If caregiver 12 presses a change button 530 (FIG. 68), a pop up window 532 notifies caregiver 12 that system staff are on their way, as shown in FIG. 73. A second pop up window 534 then appears, indicating how well caregiver 12 performed relative to a predefined target, as shown in FIG. 74. If caregiver 12 responds within a predetermined amount of time (e.g., in <1 hour), pop up 534 displays highly positive remarks. If caregiver 12 responds slightly outside the predetermined amount of time (e.g., in <2 hour), pop up 534 displays less positive/more negative remarks. If caregiver 12 responds far outside the predetermined amount of time (e.g., in >2 hours), pop up 534 displays even less positive/more negative remarks.

After caregiver 12 acknowledges a second push notification, they are brought back to the resident specific screen, and it displays "change in progress" (FIG. 75) until a change on the online change log is manually entered.

Figure 78:
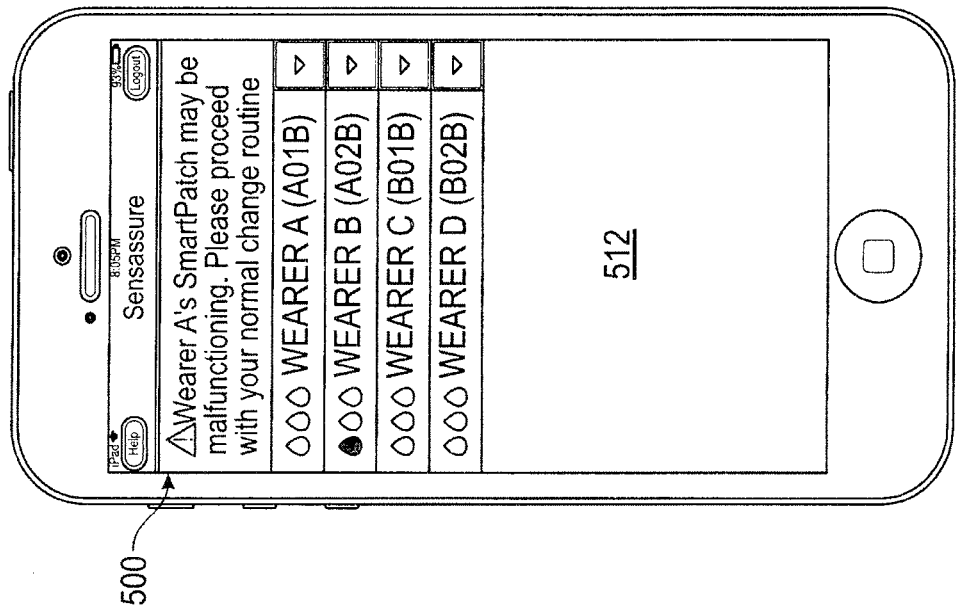
Figure 77:
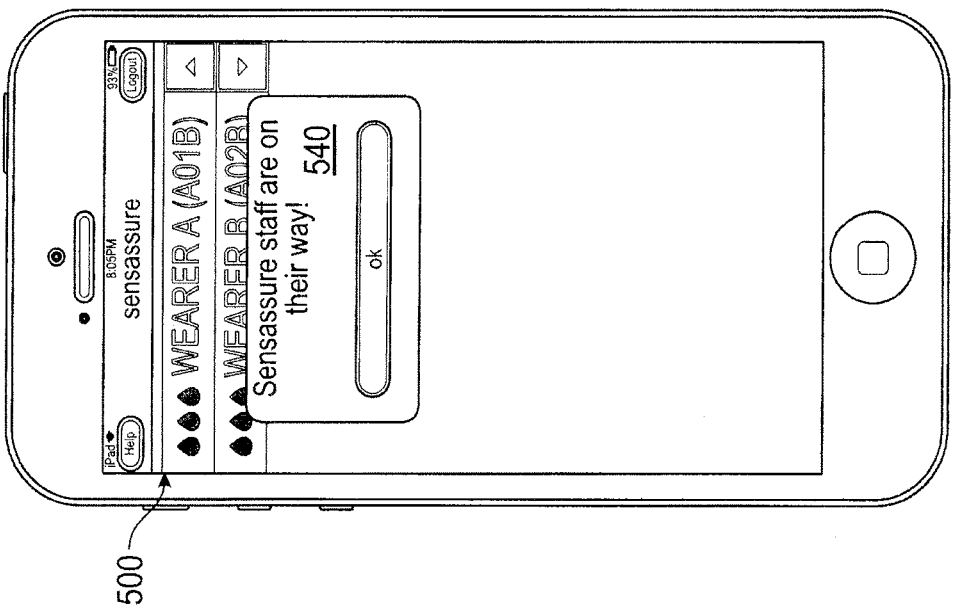
Figure 79:
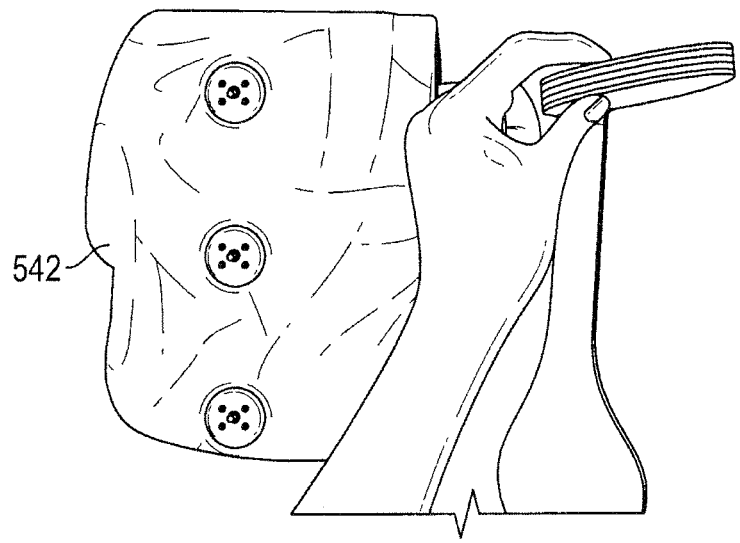
FIGS. 79-83 are depictions of steps for applying a device to an absorbent article, in accordance with aspects of the present disclosure.
Figure 80:
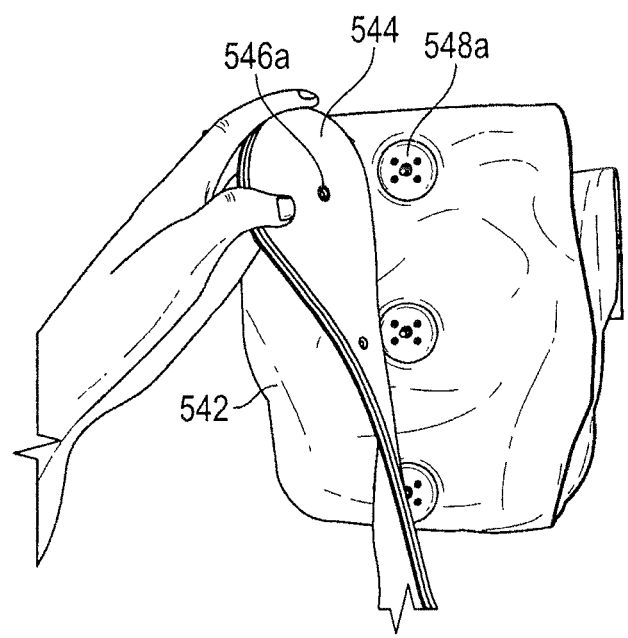
Figure 81:
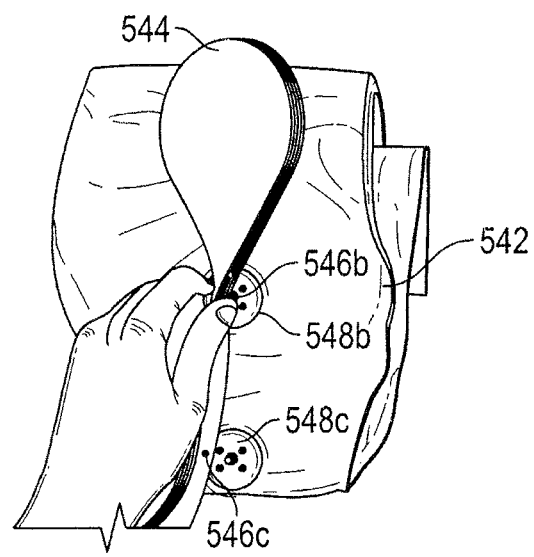

If caregiver 12 would like to notify system staff at any point, they can press a "help" button 536 at the top left hand corner of home screen 512. Doing so will display a pop up window 538 asking caregiver 12 if they would like to call system staff. If so, system staff is notified via text message, and a pop up window 540 appears indicating that system staff is on its way. FIG. 78 shows home screen 512 with multiple wearers 14 listed.

Additional functionality may be built into the application, using the components, devices, models, and/or algorithms of system 10 described above. For example, the application may automatically reorder wearers 14 based on their wetness status and/or room number to provide a more seamless workflow to caregivers 12. Additionally or alternatively, the application may provide caregivers 12 with information from other sensor modalities to allow them to determine if a resident needs to be turned/repositioned, etc. Additionally or alternatively, the application may provide caregivers 12 with an indication of when a wearer 14 may have an episode of urinary and/or faecal incontinence.

Figure 82:
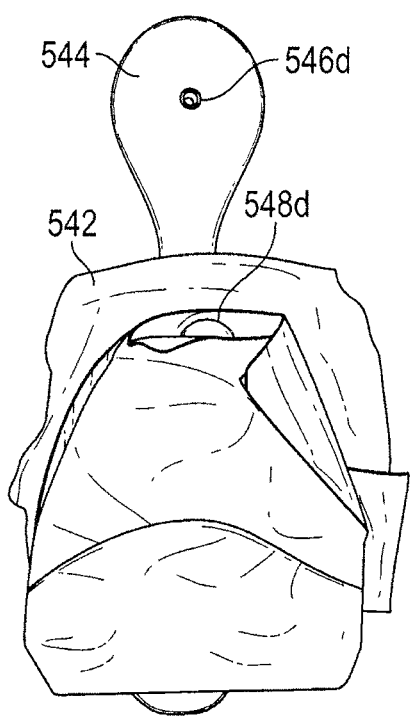
Figure 83:
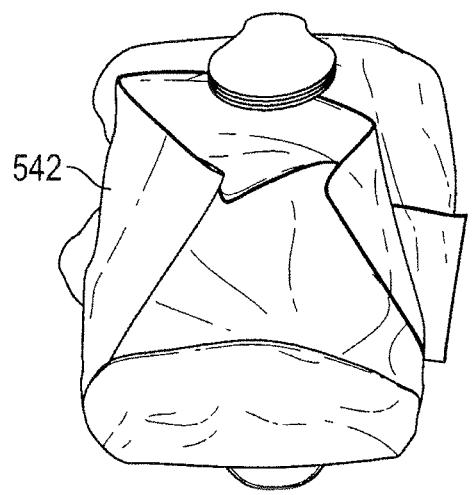

FIGS. 79-83 depict application of one type of device 17 to absorbent article 16 (e.g., a brief 542). A first step, shown in FIG. 79, includes retrieving absorbent article 16, and ensuring a battery (not shown) of device 17 (e.g., a garment or patch 544), for powering one or more sensors and/or other electronic components (not shown) in patch 544, may be in position at a front (anterior side) of absorbent article 16. In the next step, shown in FIG. 80, while brief 542 remains folded, a front/anterior button 546a of patch 544 is clipped or buttoned to a front/anterior electrocardiogram (ECG) electrode 548a (pre-mounted on an exterior surface of brief 542) by pressing button 546a against electrode 548a until a "click" is heard. In the next step, shown in FIG. 81, while brief 542 remains folded, middle buttons 546b, 546c of patch 544 may be buttoned to ECG electrodes 548b, 548c on brief 542. As shown in FIG. 82, brief 542 may then be flipped over. As shown in FIG. 83, a back/posterior button 546d of patch 544 may be buttoned to an ECG electrode 548d at the back/posterior of brief 542.

It will be apparent to those skilled in the art that various modifications and variations can be made in the disclosed systems and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A system for detecting moisture in an absorbent article worn by a wearer, comprising:
   an impedance sensing element including electrodes;
   an attachment member configured to secure the impedance sensing element at a location on an exterior surface of the absorbent article such that the electrodes are positioned exterior to the absorbent article, capacitively coupled to an interior region of the absorbent article, and positioned to measure an impedance of the absorbent article from the location exterior to the absorbent article; and
   an impedance measurement subsystem for measuring the impedance of the absorbent article, and extracting a real component of the impedance, which includes a resistive component, and an imaginary component of the impedance, which includes a reactive component, wherein the impedance measurement subsystem is configured to determine a relationship between the resistive and reactive components of the impedance and a characteristic of the moisture in the absorbent article.

2. The system of claim 1, wherein the characteristic includes a presence of the moisture in the absorbent article.

3. The system of claim 1, wherein the characteristic includes an amount of the moisture in the absorbent article.

4. The system of claim 1, wherein the impedance measurement subsystem is configured to measure the impedance between the electrodes.

5. The system of claim 1, wherein the impedance is a complex impedance having a magnitude and a phase.

6. The system of claim 5, wherein the magnitude is indicative of the characteristic of the moisture.

7. The system of claim 5, wherein the phase is indicative of the characteristic of the moisture.

8. The system of claim 5, wherein a reduction in the phase and the magnitude is indicative of a state wherein the absorbent article is wet but not filled to capacity.

9. The system of claim 5, wherein a reduction in the magnitude but not the phase is indicative of a state where the absorbent article is filled to capacity.

10. The system of claim 1, wherein the impedance measurement subsystem is configured to perform an optimization technique using a linear regression, a neural network, and/or a support vector machine, to determine the relationship between the resistive and reactive components of the impedance and the characteristic of the moisture.

11. The system of claim 1, wherein the impedance measurement subsystem is configured to perform a simulation to determine the relationship between the resistive and reactive components of the impedance and the characteristic of the moisture.

12. The system of claim 1, wherein the impedance measurement subsystem is configured to acquire data from another system that is distinct from the system, to determine the relationship between the resistive and reactive components of the impedance and the characteristic of the moisture.

13. The system of claim 1, wherein the impedance measurement subsystem is configured to measure the impedance with a sinusoid of a single frequency.

14. The system of claim 1, wherein the impedance measurement subsystem is configured to measure the impedance by applying a voltage to one of the electrodes and measuring current at another of the electrodes.

15. The system of claim 1, wherein the impedance measurement subsystem is configured to measure the impedance by applying a current to one of the electrodes and measuring a voltage between that electrode and another of the electrodes.

16. The system of claim 1, wherein the impedance measurement subsystem is configured to determine the characteristic of the moisture using the real component.

17. The system of claim 16, wherein the characteristic of the moisture includes a degree of wetness of the absorbent article.

18. The system of claim 1, wherein the impedance measurement subsystem is configured to measure the impedance at discrete frequencies.

19. The system of claim 1, wherein the impedance measurement subsystem is configured to acquire the resistive and reactive components at discrete frequencies, to determine the relationship between the resistive and reactive components and the characteristic of the moisture.

20. The system of claim 1, wherein the impedance measurement subsystem is further configured to determine whether the impedance sensing element is attached to the absorbent article based on a characteristic of the reactive component.

21. An incontinence management system, comprising:
an absorbent article for wearing by a wearer, wherein the absorbent article includes:
an interior,
an exterior, and
a water resistant barrier layer between the interior and the exterior;
an impedance sensing element including electrodes;
an attachment member for securing the impedance sensing element to the exterior, wherein the electrodes are separated from the interior by the barrier layer, are capacitively coupled to the interior through the barrier layer, and are positioned to measure an impedance of the absorbent article from the exterior; and
an impedance measurement subsystem for measuring the impedance of the absorbent article, and extracting a real component of the impedance, which includes a resistive component, and an imaginary component of the impedance, which includes a reactive component, wherein the impedance measurement subsystem is configured to determine a relationship between the resistive and reactive components of the impedance and a characteristic of the moisture in the absorbent article.

22. A method for detecting moisture in an absorbent article worn by a wearer using an impedance sensing element, comprising:
securing the impedance sensing element to an exterior of the absorbent article such that electrodes of the impedance sensing element are exterior to the absorbent article, capacitively coupled to an interior of the absorbent article, and positioned to measure an impedance of the absorbent article from the exterior;
measuring the impedance of the absorbent article; and
extracting a real component of the impedance, which includes a resistive component, and an imaginary component of the impedance, which includes a reactive component, wherein the impedance measurement subsystem is configured to determine a relationship between the resistive and reactive components of the impedance and a characteristic of the moisture in the absorbent article.

* * * * *